(12) United States Patent      (10) Patent No.: US 8,901,110 B2
Kim et al.      (45) Date of Patent: Dec. 2, 2014

(54) USE OF BIOMARKERS IN METHODS FOR THE TREATMENT OF HEPATOCELLULAR CARCINOMA

(71) Applicant: Celgene Corporation, Summit, NJ (US)

(72) Inventors: Miran Kim, North Providence, RI (US); Jack R. Wands, East Greenwich, RI (US); Sarah Beseme, Providence, RI (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 13/740,012

(22) Filed: Jan. 11, 2013

(65) Prior Publication Data

US 2013/0183675 A1     Jul. 18, 2013

Related U.S. Application Data

(66) Substitute for application No. 61/586,672, filed on Jan. 13, 2012.

(51) Int. Cl.
*A01N 43/00* (2006.01)
*A61K 31/33* (2006.01)

(52) U.S. Cl.
USPC ............................................. 514/183; 514/1

(58) Field of Classification Search
USPC ...................................... 514/1, 183
See application file for complete search history.

(56) References Cited

U.S. PATENT DOCUMENTS

2005/0014801 A1 * 1/2005 Zeng .............................. 514/359
2013/0045203 A1 * 2/2013 Joshi et al. ................. 424/133.1

OTHER PUBLICATIONS

Cui et al., "Alterations of β-catenin and Tcf-4 instead of GSK-3β contribute to activation of Wnt pathway in hepatocellular carcinoma," *Chinese Med. J.*, 116(12):1885-1892 (2003).
Nambotin et al., "Points of therapeutic intervention along the Wnt signaling pathway in hepatocellular carcinoma," *Anti-Cancer Agents in Medicinal Chem.*, 11(6):549-559 (2011).
Tsedensodnom et al., "Identification of T-cell factor-4 isoforms that contribute to the malignant phenotype of hepatocellular carcinoma cells," *Exp. Cell Res.*, 317(7):920-931 (2011).
Tsedensodnom, "Identification and characterization of T cell factor-4 (TCF-4) isoforms of Wnt signalling in hepatocellular carcinoma," Chapters 3-5, Dissertation submitted in partial fulfillment of the requirement for the degree of doctor of philosophy in the department of molecular biology, cell biology, and biochemistry at Brown University, May 2010.
Wei et al., "Small molecule antagonists of Tcf4/β-catenin complex inhibits the growth of HCC cells in vitro and in vivo," *Int. J. Cancer*, 126:2426-2436 (2010).
Yuzugullu et al., "Canonical Wnt signaling is antagonized by noncanonical Wnt5a in hepatocellular carcinoma cells," *Molecular Cancer*, 8(1):90 (2009).
Zhang et al., "Phosphorylated ERK is a potentional predictor of sensitivity to sorafenib when treating hepatocellular carcinoma: evidence from an in vitro study," *BMC Medicine*, 7(1):41 (2009).
Zhao et al., "Aberrant expression and function of TCF4 in the proliferation of hepatocellular carcinoma cell line BEL-7402," *Cell Res.*, 14(1):74-80 (2004).
Zhu et al., "Predicting the response to sorafenib in hepatocellular carcinoma: where is the evidence for phosyporylated extracellular signaling-regulated kinase (pERK)?", *BMC Medicine*7(1):42 (2009).

* cited by examiner

*Primary Examiner* — Ardin Marschel
(74) *Attorney, Agent, or Firm* — Jones Day

(57) ABSTRACT

Provided herein are biomarkers for hepatocellular carcinoma and uses thereof.

27 Claims, 22 Drawing Sheets

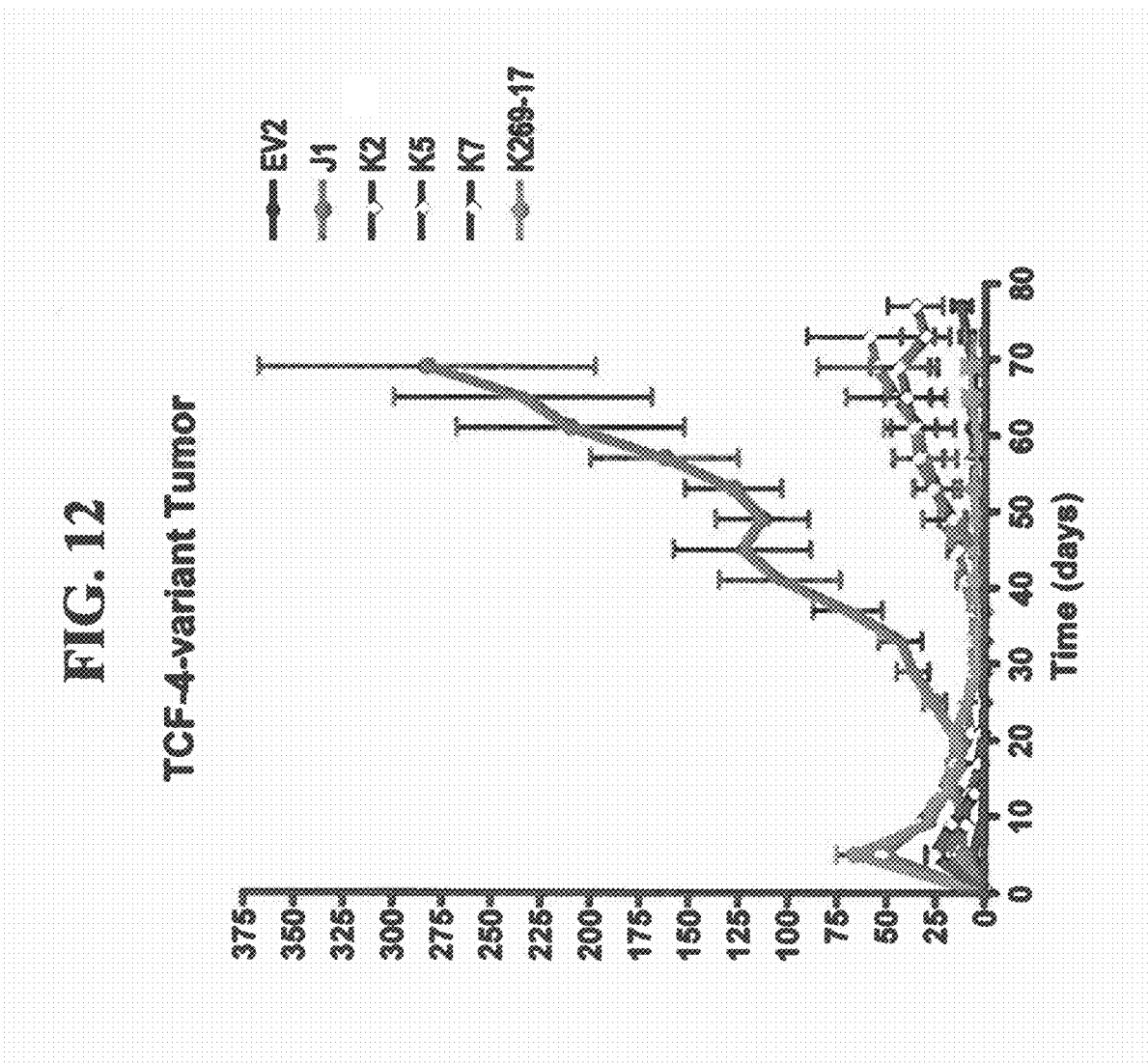

FIG. 13

| ProbeID | Gene symbol | Gene name | Fold change (TCF-4J/TCF-4K) | Biological activity/Pathway |
|---|---|---|---|---|
| A_33_P3249046 | CLDN2 | claudin 2 | 89.356 | cell-cell adhesion, tight junction |
| A_33_P3371650 | STK17B | serine/threonine kinase 17b | 51.204 | serine/threonine kinase activity, apoptosis |
| A_23_P7313 | SPP1 | secreted phosphoprotein 1 | 32.925 | cell-cell adhesion, osteoblast differentiation |
| A_23_P148015 | AXIN2 | axin 2 | 29.801 | Wnt/β-catenin signaling |
| A_23_P102611 | WISP2 | WNT1 inducible signaling pathway protein 2 | 9.394 | Wnt/β-catenin signaling, cell growth |
| A_23_P52761 | MMP7 | matrix metallopeptidase 7 (matrilysin, uterine) | 8.742 | collagen catabolic process, cell proliferation |
| A_33_P3421913 | CADM1 | cell adhesion molecule 1 | 4.318 | cell-cell adhesion |
| A_24_P225679 | IRS1 | insulin receptor substrate 1 | 3.418 | IGF signaling |
| A_23_P94501 | ANXA1 | annexin A1 | 3.108 | calcium-dependent phospholipid binding, apoptosis and cell proliferation |
| A_23_P1800 | CAMK2N1 | calcium/calmodulin-dependent protein kinase II inhibitor 1 | 2.691 | calcium-dependent protein kinase inhibitor activity |
| A_23_P85105 | PLCD4 | phospholipase C, delta 4 | 2.561 | phosphatidylinositol phospholipase C activity |
| A_24_P1810S | ASPH | aspartate beta-hydroxylase | 2.395 | peptidyl-aspartic acid hydroxylation, cell proliferation |
| A_23_P206280 | GPR56 | G protein-coupled receptor 56 | 2.278 | GPCR signaling |
| A_33_P3369844 | CD24 | CD24 molecule | 2.105 | cell-cell adhesion, apoptosis and migration |
| A_23_P210763 | JAG1 | jagged 1 (Alagille syndrome) | 2.038 | Notch signaling |

*List of TCF-4J isoform-dependent upregulated target genes in HAK1A HCC cell line. These genes are related to three pathways, i.e. Wnt/β-catenin, IRS-1, and Notch signaling, which are important in HCC pathogenesis.*

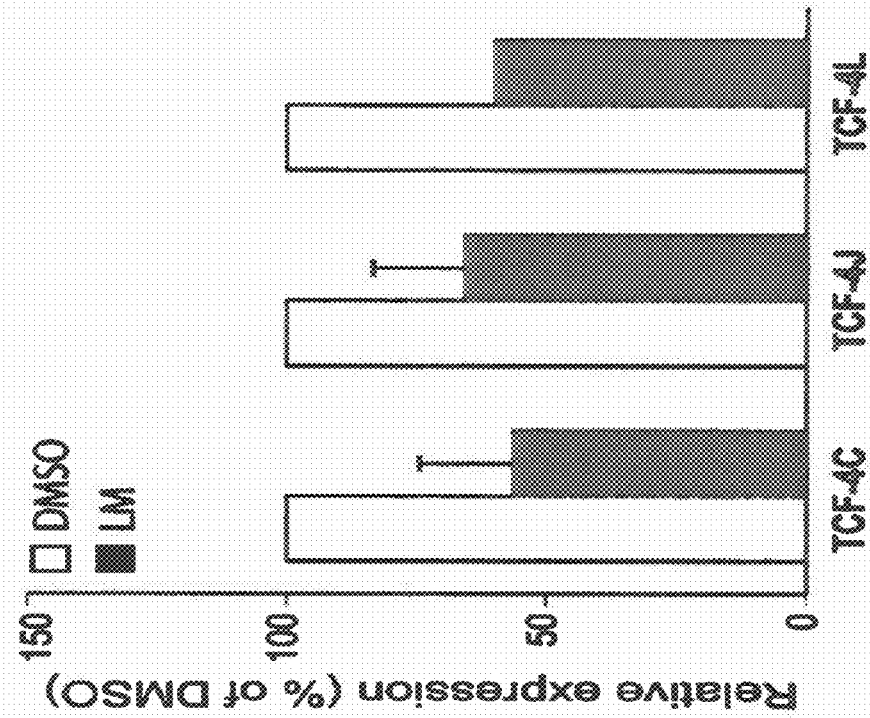
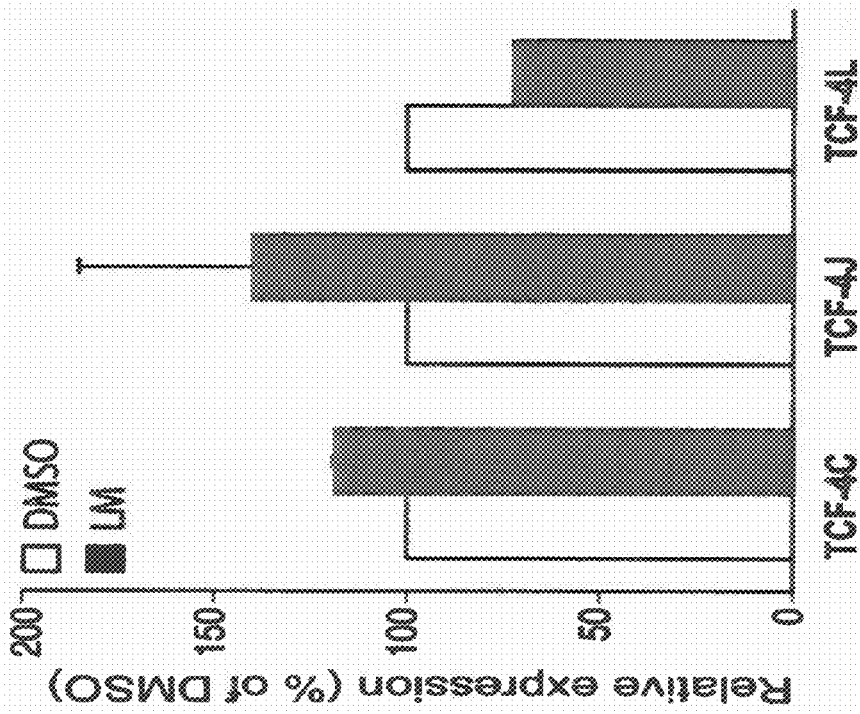
FIG. 16

a single biomarker may not always provide the full picture …

USE OF BIOMARKERS IN METHODS FOR THE TREATMENT OF HEPATOCELLULAR CARCINOMA

This application claims priority to U.S. Provisional Application No. 61/586,672, filed Jan. 13, 2012, the entirety of which is incorporated herein by reference.

1. FIELD

Provided herein are biomarkers for hepatocellular carcinoma and uses thereof.

2. BACKGROUND

Hepatocellular carcinoma (HCC), also known as malignant hepatoma, is the most common primary malignancy of the liver and accounts for 80-90% of primary liver tumors. HCC is one of the most common and devastating malignant diseases worldwide, responsible for more than 1 million deaths annually in the world (Parkin et al., *CA Cancer J. Clin.* 1999, 49, 33-64; Bruix et al., *Cancer Cell* 2004, 5, 215-219).

The major risk factors for the development of HCC include hepatitis B or C viral infection, and alcoholic liver disease (Rustgi, *Gastroenterol. Clin. North Am.* 1987, 16, 545-551; Bosch et al., *Semin. Liver Dis.* 1999, 19, 271-285; Bosch et al., *Gastroenterology* 2004, 127, S5-S16; Moradpour et al., *Eur. J. Gastro & Hepatol.* 2005, 17, 477-483; Koike et al., *J. Gastroenterol. Hepatol.* 2008, 23, S87-S91; de Oliveria Andrade, *J. Glob. Infect. Dis.* 2009, 1, 33-37). HCC arises most commonly in cirrhotic livers following infection with hepatitis B virus (HBV) or hepatitis C virus (HCV) (Liaw, *Semin. Liver Dis.* 2005, 25, 40-47; Koike *Clin. Gastroenterol. Hepatol.* 2005, 3, 132-135). HCC is associated with HBV infection in about 50% of cases (Liaw, *Semin. Liver Dis.* 2005, 25, 40-47). HCV infection is the cause of 70% of the cases of HCC in Japan (Hasan, et al., *Hepatology*, 1990, 12:589-591; El-Serag et al., *N. Engl. J. Med.* 1999, 340, 745-750). The HCC incidence has been increasing in Western countries in recent years due to the spread of hepatitis C virus (HCV) infection (El-Serag, *Hepatology* 2002, 36, S74-83; Trevisani et al., *Carcinogenesis* 2008, 29, 1299-1305).

Hepatocellular carcinoma is a disease of worldwide significance, of which there is no truly effective therapy, particularly for advanced disease. Therefore, there is a need for biomarkers to aid a HCC treatment and a method of predicting the responsiveness of a HCC patient to a HCC treatment, e.g., chemotherapy.

3. SUMMARY

Provided herein is a method of identifying a subject having hepatocellular carcinoma who is likely to be responsive to a treatment compound, comprising:

a) determining the level of a biomarker in a hepatocellular carcinoma cell-containing sample from the subject, wherein the biomarker is selected from the group consisting of TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, and combinations thereof; and b) comparing the level of the biomarker in the sample to a reference level of the biomarker; wherein the subject is likely to be responsive to the treatment if the level of the biomarker in the sample of the subject is higher than the reference level of the biomarker.

Also provided herein is a method of identifying a subject having poorly differentiated hepatocellular carcinoma who is likely to be responsive to a treatment compound, comprising:

a) determining the level of a biomarker in a hepatocellular carcinoma cell-containing sample from the subject, wherein the biomarker is selected from the group consisting of TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, and combinations thereof; and b) comparing the level of the biomarker in the sample to a reference level of the biomarker; wherein the subject is likely to be responsive to the treatment if the level of the biomarker in the sample of the subject is higher than the reference level of the biomarker.

Additionally provided herein is a method of identifying a subject having hepatocellular carcinoma who is likely to be responsive to a treatment compound, comprising:

a) determining the level of a biomarker in a hepatocellular carcinoma cell-containing sample from the subject, wherein the biomarker is selected from the group consisting of TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, and combinations thereof; and b) determining the level of the biomarker in a control sample; wherein the subject is likely to be responsive to the treatment if the level of the biomarker in the sample of the subject is higher than the level of the biomarker in the control sample.

Further provided herein is a method of identifying a subject having poorly differentiated hepatocellular carcinoma who is likely to be responsive to a treatment compound, comprising:

a) determining the level of a biomarker in a hepatocellular carcinoma cell-containing sample from the subject, wherein the biomarker is selected from the group consisting of TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, and combinations thereof; and b) determining the level of the biomarker in a control sample; wherein the subject is likely to be responsive to the treatment if the level of the biomarker in the sample of the subject is higher than the level of the biomarker in the control sample Provided herein is a method of identifying a subject having hepatocellular carcinoma who is likely to be responsive to a treatment compound, comprising:

a) obtaining a biological sample from the subject;

b) determining the level of a biomarker in the sample, wherein the biomarker is selected from the group consisting of TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, and combinations thereof; and c) comparing the level of the biomarker in the sample to a reference level of the biomarker; wherein the subject is likely to be responsive to the treatment if the level of the biomarker in the sample of the subject is higher than the reference level of the biomarker.

Provided herein is a method of identifying a subject having poorly differentiated hepatocellular carcinoma who is likely to be responsive to a treatment compound, comprising:

a) obtaining a biological sample from the subject;

b) determining the level of a biomarker in the sample, wherein the biomarker is selected from the group consisting of TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, and combinations thereof; and c) comparing the level of the biomarker in the sample to a reference level of the biomarker; wherein the subject is likely to be responsive to the treatment if the level of the biomarker in the sample of the subject is higher than the reference level of the biomarker.

Provided herein is a method of identifying a subject having hepatocellular carcinoma who is likely to be responsive to a treatment compound, comprising:

a) obtaining a biological sample from the subject;

b) determining the level of a biomarker in the sample, wherein the biomarker is selected from the group consisting of TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, and combinations thereof; and c) determining the level of the biomarker in a control sample; wherein the subject is likely to be responsive to the treatment if the level of the biomarker in the sample of the subject is higher than the level of the biomarker in the control sample.

Provided herein is a method of identifying a subject having poorly differentiated hepatocellular carcinoma who is likely to be responsive to a treatment compound, comprising:

a) obtaining a biological sample from the subject;

b) determining the level of a biomarker in the sample, wherein the biomarker is selected from the group consisting of TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, and combinations thereof; and c) determining the level of the biomarker in a control sample; wherein the subject is likely to be responsive to the treatment if the level of the biomarker in the sample of the subject is higher than the level of the biomarker in the control sample.

Provided herein is a method of predicting the responsiveness of a subject having or suspected of having hepatocellular carcinoma to a treatment compound, comprising:

a) determining the level of a biomarker in a hepatocellular carcinoma cell-containing sample from the subject, wherein the biomarker is selected from the group consisting of TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, and combinations thereof; and b) comparing the level of the biomarker in the sample to a reference level of the biomarker, wherein an increased level of the biomarker in the sample correlates with an increased responsiveness of the subject to the compound treatment.

Provided herein is a method of predicting the responsiveness of a subject having or suspected of having poorly differentiated hepatocellular carcinoma to a treatment compound, comprising:

a) determining the level of a biomarker in a hepatocellular carcinoma cell-containing sample from the subject, wherein the biomarker is selected from the group consisting of TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, and combinations thereof; and b) comparing the level of the biomarker in the sample to a reference level of the biomarker, wherein an increased level of the biomarker in the sample correlates with an increased responsiveness of the subject to the compound treatment.

Provided herein is a method of predicting the responsiveness of a subject having or suspected of having hepatocellular carcinoma to a treatment compound, comprising:

a) determining the level of a biomarker in a hepatocellular carcinoma cell-containing sample from the subject, wherein the biomarker is selected from the group consisting of TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, and combinations thereof;

b) determining the level of the biomarker in a control sample; and c) comparing the level of the biomarker in the sample from the subject to the level of the biomarker in the control sample, wherein an increased level of the biomarker in the sample correlates with an increased responsiveness of the subject to the compound treatment.

Provided herein is a method of predicting the responsiveness of a subject having or suspected of having poorly differentiated hepatocellular carcinoma to a treatment compound, comprising:

a) determining the level of a biomarker in a hepatocellular carcinoma cell-containing sample from the subject, wherein the biomarker is selected from the group consisting of TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, and combinations thereof;

b) determining the level of the biomarker in a control sample; and c) comparing the level of the biomarker in the sample from the subject to the level of the biomarker in the control sample, wherein an increased level of the biomarker in the sample correlates with an increased responsiveness of the subject to the compound treatment.

Provided herein is a method of predicting the responsiveness of a subject having or suspected of having hepatocellular carcinoma to a treatment compound, comprising:

a) obtaining a biological sample from the subject;

b) determining the level of a biomarker in the sample, wherein the biomarker is selected from the group consisting of TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, and combinations thereof; and c) comparing the level of the biomarker in the sample to a reference level of the biomarker, wherein an increased level of the biomarker in the sample correlates with an increased responsiveness of the subject to the compound treatment.

Provided herein is a method of predicting the responsiveness of a subject having or suspected of having poorly differentiated hepatocellular carcinoma to a treatment compound, comprising:

a) obtaining a biological sample from the subject;

b) determining the level of a biomarker in the sample, wherein the biomarker is selected from the group consisting of TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, and combinations thereof; and c) comparing the level of the biomarker in the sample to a reference level of the biomarker, wherein an increased level of the biomarker in the sample correlates with an increased responsiveness of the subject to the compound treatment.

Provided herein is a method of predicting the responsiveness of a subject having or suspected of having hepatocellular carcinoma to a treatment compound, comprising:

a) obtaining a biological sample from the subject;

b) determining the level of a biomarker in the sample, wherein the biomarker is selected from the group consisting of TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, and combinations thereof;

c) determining the level of the biomarker in a control sample; and d) comparing the level of the biomarker in the sample from the subject to the level of the biomarker in the control sample, wherein an increased level of the biomarker in the sample correlates with an increased responsiveness of the subject to the compound treatment.

Provided herein is a method of predicting the responsiveness of a subject having or suspected of having poorly differentiated hepatocellular carcinoma to a treatment compound, comprising:

a) obtaining a biological sample from the subject;

b) determining the level of a biomarker in the sample, wherein the biomarker is selected from the group consisting of TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, and combinations thereof;

c) determining the level of the biomarker in a control sample; and d) comparing the level of the biomarker in the sample from the subject to the level of the biomarker in the control sample, wherein an increased level of the biomarker in the sample correlates with an increased responsiveness of the subject to the compound treatment.

Provided herein is a method of monitoring the responsiveness of a subject having or suspected of having hepatocellular carcinoma to a treatment compound, comprising:

a) obtaining a first biological sample from the subject;

b) determining the level of a biomarker in the first sample, wherein the biomarker is selected from the group consisting of TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, and combinations thereof;

c) administering the compound to the subject;

d) thereafter obtaining a second biological sample from the subject;

e) determining the level of the biomarker in the second sample, and f) comparing the levels of the biomarker in the first and second biological samples; wherein a decreased level of the biomarker in the second biological sample indicates an effective response.

Provided herein is a method of monitoring the responsiveness of a subject having or suspected of having poorly differentiated hepatocellular carcinoma to a treatment compound, comprising:

a) obtaining a first biological sample from the subject;

b) determining the level of a biomarker in the first sample, wherein the biomarker is selected from the group consisting of TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, and combinations thereof;

c) administering the compound to the subject;

d) thereafter obtaining a second biological sample from the subject;

e) determining the level of the biomarker in the second sample, and f) comparing the levels of the biomarker in the first and second biological samples; wherein a decreased level of the biomarker in the second biological sample indicates an effective response.

Provided herein is a method of monitoring the compliance of a subject having or suspected of having hepatocellular carcinoma with a treatment compound, comprising:

a) obtaining a biological sample from the subject;

b) determining the level of a biomarker in the sample, wherein the biomarker is selected from the group consisting of TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, and combinations thereof;

c) comparing the level of the biomarker with the level in a control untreated sample from the subject; wherein a decreased level of the biomarker in the biological sample in comparison with the level in the control indicates the compliance of the subject with the treatment.

Provided herein is a method of monitoring the compliance of a subject having or suspected of having poorly differentiated hepatocellular carcinoma with a treatment compound, comprising:

a) obtaining a biological sample from the subject;

b) determining the level of a biomarker in the sample, wherein the biomarker is selected from the group consisting of TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, and combinations thereof;

c) comparing the level of the biomarker with the level in a control untreated sample from the subject; wherein a decreased level of the biomarker in the biological sample in comparison with the level in the control indicates the compliance of the subject with the treatment.

Provided herein is an array of probes for determining the levels of two or more biomarkers in a sample by hybridizing with one or more of the polynucleotides of the biomarkers under stringent condition, wherein the biomarkers are each independently selected from TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, wherein the levels of the biomarkers are used to select a subject for treatment of hepatocellular carcinoma (e.g., poorly differentiated hepatocellular carcinoma) with a treatment compound; to predict or monitor the responsiveness of a subject to the treatment; or monitoring the compliance of a subject with the treatment.

Provided herein is an array of probes for determining the levels of two or more biomarkers in a sample by hybridizing with one or more of mRNAs of the biomarkers under stringent condition, wherein the biomarkers are each independently selected from TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, wherein the levels of the biomarkers are used to select a subject for treatment of hepatocellular carcinoma (e.g., poorly differentiated hepatocellular carcinoma) with a treatment compound; to predict or monitor the responsiveness of a subject to the treatment; or monitoring the compliance of a subject with the treatment.

Provided herein is an array of antibodies for determining the levels of two or more biomarkers in a sample, wherein the biomarkers are each independently selected from TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, wherein the levels of the biomarkers are used to select a subject for treatment of hepatocellular carcinoma (e.g., poorly differentiated hepatocellular carcinoma) with a treatment compound; to predict or monitor the responsiveness of a subject to the treatment; or monitoring the compliance of a subject with the treatment.

Provided herein is a panel of isolated biomarkers comprising two or more biomarkers, each of which is independently selected from TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24.

Provided herein is a panel of isolated biomarkers comprising two or more biomarkers, each of which is independently selected from TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24.

Provided herein is a panel of isolated biomarkers comprising TCF-4C, TCF-4J, and TCF-4L.

Provided herein is a kit for determining the level of a biomarker in a biological sample from a subject, wherein the biomarker is selected from the group consisting of TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, and combinations thereof.

4. DETAILED DESCRIPTION

The methods, arrays, probes, and kits provided herein are based, in part, on the discovery that an increased level of certain molecules (e.g., mRNAs, cDNA, or proteins) in a biological sample can be utilized as biomarkers to predict responsiveness of a subject having or suspected to have hepatocellular carcinoma to a treatment compound, e.g., thalidomide, lenalidomide, pomalidomide, or 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

In certain embodiments, the methods provided herein are based on comparison of the level of one or more biomarkers in a biological sample from a subject having or suspected to have hepatocellular carcinoma to a reference level of the biomarkers or the level of a control. The biomarker level is used to determine or to predict, for example, the likelihood of the subject's responsiveness to a treatment compound, such as thalidomide, lenalidomide, pomalidomide, or 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

4.1 BRIEF DESCRIPTION OF FIGURES

FIG. 12 shows growth of xenografted tumors in nude mice.

FIG. 13 shows a list of TCF-4J dependent target genes in HCC cell line that are upregulated.

FIG. 16 shows the change in the expression of TCF-4 isoforms in HCC cell lines, Focus and Hub7, upon treatment with LM.

4.2 DEFINITIONS

Figure 1:
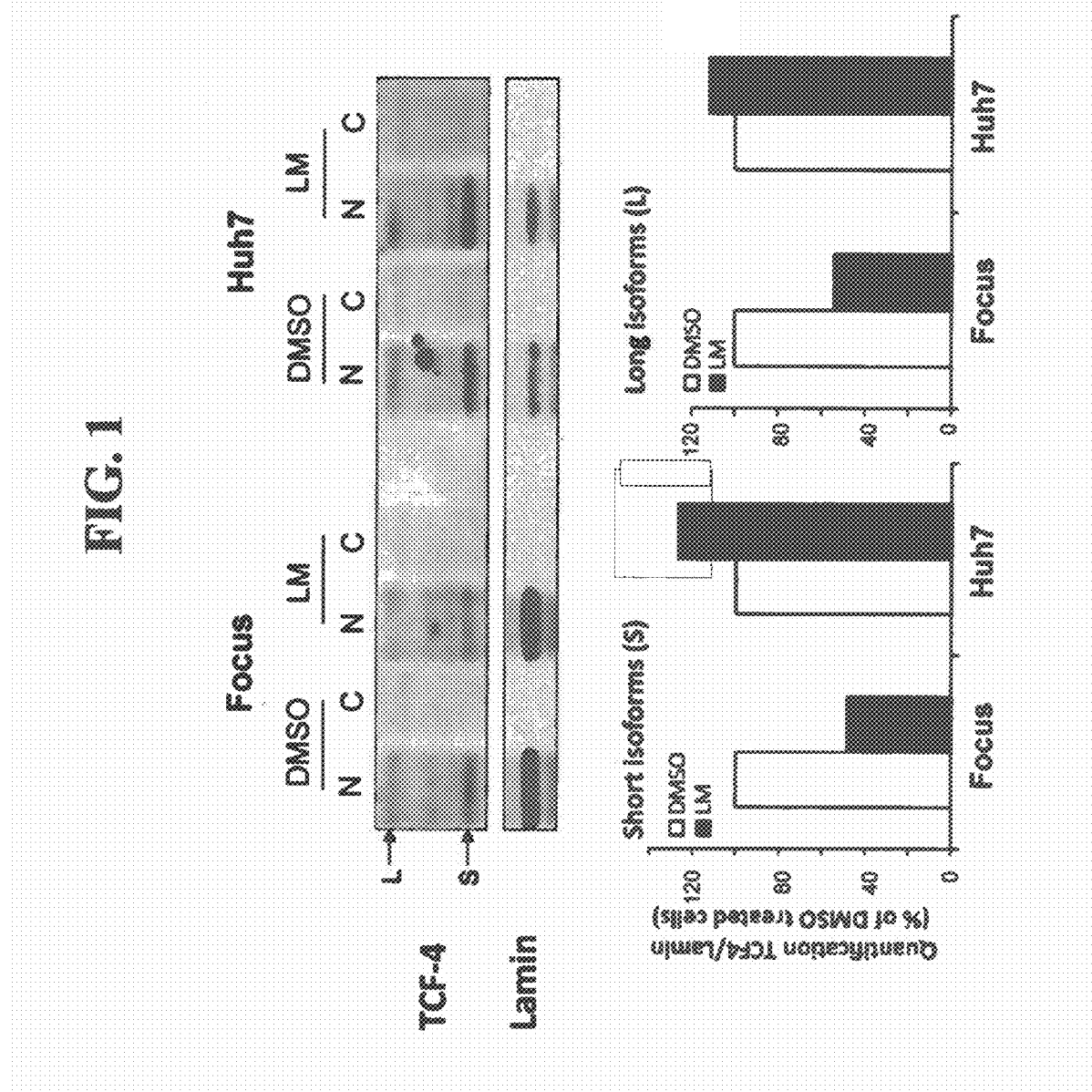
FIG. 1 shows the change in TCF-4 transcription factor levels in HCC cell lines, Focus and Hub7, upon treatment with lenalidomide ("LM").

The term "treat," "treating," or "treatment" refers to alleviating or abrogating a disease, e.g., hepatocellular carcinoma, or one or more of the symptoms associated with the disease; or alleviating or eradicating the cause(s) of the disease itself.

The term "therapeutically effective amount" of a compound refers to the amount of a compound that, when administered, is sufficient to prevent development of, or alleviate to some extent, one or more of the symptoms of a disease, e.g., hepatocellular carcinoma, being treated. The term also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician. Furthermore, a therapeutically effective amount of a compound means an amount of a therapeutic agent, alone or in combination with other therapies, which provides a therapeutic benefit in the treatment or management of a disease, e.g., hepatocellular carcinoma. The term encompasses an amount that improves overall therapy, reduces, or avoids symptoms or causes of a disease, e.g., hepatocellular carcinoma, or enhances the therapeutic efficacy of another therapeutic agent.

The term "level" refers to the amount, accumulation, or rate of a biomarker molecule. A level can be represented, for example, by the amount or the rate of synthesis of a massager RNA (mRNA) encoded by a gene, the amount or the rate of synthesis of a polypeptide or protein encoded by a gene, or the amount or the rate of synthesis of a biological molecule accumulated in a cell or biological fluid. The term "level" refers to an absolute amount of a molecule in a sample or to a relative amount of the molecule, determined under steady-state or non-steady-state conditions.

The term "responsiveness" or "responsive" when used in reference to a treatment refer to the degree of effectiveness of the treatment in lessening or decreasing the symptoms of a disease, e.g., hepatocellular carcinoma, being treated. For example, the term "increased responsiveness" when used in reference to a treatment of a cell or a subject refers to an increase in the effectiveness in lessening or decreasing the symptoms of the disease when measured using any methods known in the art. In certain embodiments, the increase in the effectiveness is at least about 5%, at least about 10%, at least about 20%, at least about 30%, at least about 40%, or at least about 50%.

The term "effective patient response" refers to an increase in the therapeutic benefit to a patient in treating a disease, e.g., hepatocellular carcinoma. In certain embodiments, the increase is at least about 5%, at least about 10%, at least about 20%, at least about 30%, at least about 40%, or at least about 50%. An "effective patient tumor response" can be, for example, an about 5%, about 10%, about 25%, about 50%, or about 100% decrease in one or more physical symptoms of the disease or the tumor size.

The term "likelihood" refers to an increase in the probability of an event. The term "likelihood" when used in reference to the effectiveness of a patient response to a treatment of a disease, e.g., hepatocellular carcinoma, contemplates an increased probability that the symptoms of the disease will be lessened or decreased.

The term "predict" generally means to determine or tell in advance. When used to "predict" the effectiveness of the treatment of a disease (e.g., hepatocellular carcinoma), for example, the term "predict" can mean that the likelihood of the outcome of the treatment can be determined at the outset, before the treatment has begun, or before the treatment period has progressed substantially.

The term "polypeptide," "protein," or "peptide," as used herein interchangeably, refers to a polymer of two or more amino acids in a serial array, linked through one or more peptide bond(s). The term encompasses proteins, protein fragments, protein analogues, oligopeptides, and peptides. The amino acids of the polypeptide, protein, or peptide can be naturally occurring amino acids or synthetic amino acids (e.g., mimics of naturally occurring amino acids). The polypeptide, protein, or peptide can be made synthetically or purified from a biological sample. The polypeptide, protein, or peptide also encompasses modified polypeptides, proteins, and peptides, e.g., a glycopolypeptide, glycoprotein, or glycopeptide; or a lipopolypeptide, lipoprotein, or lipopeptide.

The term "antibody" refers to a polypeptide that specifically binds an epitope (e.g., an antigen). The term "antibody" is used herein in the broadest sense and covers fully assembled antibodies, antibody fragments which retain the ability to specifically bind to an antigen (e.g., Fab, F(ab')$_2$, Fv, and other fragments), single chain antibodies, diabodies, antibody chimeras, hybrid antibodies, bispecific antibodies, and humanized antibodies. The term "antibody" also covers both polyclonal and monoclonal antibodies.

The term "expressed" or "expression" refers to the transcription from a gene to give an RNA nucleic acid molecule, e.g., mRNA, at least complementary in part to a region of one of the two nucleic acid strands of the gene. The term "expressed" or "expression" as used herein also refers to the translation from an RNA molecule to give a protein, a polypeptide or a portion thereof.

An mRNA that is "unregulated" generally refers to an increase in the level of express of the mRNA in response to a given treatment or condition. An mRNA that is "downregulated" generally refers to a "decrease" in the level of expression of the mRNA in response to a given treatment or condition. In some situations, the mRNA level can remain unchanged upon a given treatment or condition. An mRNA from a patient sample can be "unregulated," i.e., the level of mRNA can be increased, for example, by about 5%, about 10%, about 20%, about 30%, about 40%, about 50%, about 60%, about 70%, about 90%, about 100%, about 200%, about 300%, about 500%, about 1,000%, about 5,000% or more of the comparative control mRNA level or a reference level. Alternatively, an mRNA can be "downregulated," i.e., the level of mRNA level can be decreased, for example, by about 99%, about 95%, about 90%, about 80%, about 70%, about 60%, about 50%, about 40%, about 30%, about 20%, about 10%, about 5%, about 2%, about 1% or less of the comparative control mRNA level or a reference level.

Similarly, the level of a polypeptide, protein, or peptide from a patient sample can be increased as compared to a control or a reference level. This increase can be about 5%, about 10%, about 20%, about 30%, about 40%, about 50%, about 60%, about 70%, about 90%, about 100%, about 200%, about 300%, about 500%, about 1,000%, about 5,000% or more of the comparative control protein level or a reference level. Alternatively, the level of a protein biomarker can be decreased. This decrease can be, for example, present at a level of about 99%, about 95%, about 90%, about 80%, about 70%, about 60%, about 50%, about 40%, about 30%, about 20%, about 10%, about 5%, about 2%, about 1% or less of the comparative control protein level or a reference level.

The terms "determining", "measuring", "evaluating", "assessing" and "assaying" are used interchangeably herein to refer to a form of measurement, including determining if an element is present or not. The measurement can be quantitative and/or qualitative determinations. "Assessing the presence of" can include determining the amount of something present, as well as determining whether it is present or absent.

The terms "nucleic acid" and "polynucleotide" are used interchangeably herein to refer to a polymer of nucleotides, e.g., deoxyribonucleotides or ribonucleotides, or compounds, which can hybridize with a naturally occurring nucleic acid in a sequence specific manner analogous to that of two naturally occurring nucleic acids, e.g., participating in Watson-Crick base pairing interactions. As used herein in the context of a polynucleotide sequence, the term "bases" (or "base") is synonymous with "nucleotides" (or "nucleotide"), i.e., the monomer subunit of a polynucleotide. The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. The term "analogue" of a "nucleic acid" or "polynucleotide" refers to a molecule having a structural feature that is recognized in the literature as being a mimetic, derivative, having an analogous structure, or other like terms, and includes, for example, a polynucleotide incorporating a non-natural nucleotide, a nucleotide mimetic such as a 2'-modified nucleoside, peptide nucleic acid, oligomeric nucleoside phosphonate, and any polynucleotide that has added substituent groups, such as protecting groups or linking moieties.

The term "complementary" refers to specific binding between polynucleotides based on the sequences of the polynucleotides. As used herein, a first polynucleotide and a second polynucleotide are complementary if they bind to each other in a hybridization assay under stringent conditions, e.g., if they produce a given or detectable level of signal in a hybridization assay. Portions of polynucleotides are complementary to each other if they follow conventional base-pairing rules, e.g., A pairs with T (or U) and G pairs with C, although small regions (e.g. less than about 3 bases) of mismatch, insertion, or deleted sequence may be present.

The term "sequence identity" or "identity" in the context of two nucleic acid sequences refers to the residues in the two sequences which are the same when aligned for maximum correspondence over a specified comparison window, and can take into consideration additions, deletions and substitutions.

The term "substantial identity" or "homologous" in their various grammatical forms in the context of polynucleotides generally means that a polynucleotide comprises a sequence that has a desired identity, for example, at least 60%, at least 70%, at least 80%, at least 90% and at least 95% sequence identity, compared to a reference sequence. Another indication that nucleotide sequences are substantially identical is if two molecules hybridize to each other under stringent conditions.

As used herein, the term "bound" can be used herein to indicate direct or indirect attachment. In the context of chemical structures, "bound" (or "bonded") may refer to the existence of a chemical bond directly joining two moieties or indirectly joining two moieties (e.g., via a linking group or any other intervening portion of the molecule). The chemical bond may be a covalent bond, an ionic bond, a coordination complex, hydrogen bonding, van der Waals interactions, or hydrophobic stacking, or may exhibit characteristics of multiple types of chemical bonds. In certain instances, "bound" includes embodiments where the attachment is direct and also embodiments where the attachment is indirect.

The terms "isolated" and "purified" refer to isolation of a substance (such as mRNA or protein) such that the substance comprises a substantial portion of the sample in which it resides, i.e., greater than the substance is typically found in its natural or un-isolated state. Typically, a substantial portion of the sample comprises, e.g., greater than about 1%, greater than about 2%, greater than about 5%, greater than about 10%, greater than about 20%, greater than about 50%, or more, usually up to about 90% to 100% of the sample. For example, a sample of isolated mRNA can typically comprise at least about 1% total mRNA. Techniques for purifying polynucleotides are well known in the art and include, for example, gel electrophoresis, ion-exchange chromatography, affinity chromatography, flow sorting, and sedimentation according to density.

The term "biological sample" as used herein refers to a sample obtained from a biological subject, including a sample of biological tissue or fluid origin, obtained, reached, or collected in vivo or in situ. A biological sample also includes samples from a region of a biological subject containing precancerous or cancer cells or tissues. Such samples can be, but are not limited to, organs, tissues, fractions and cells isolated from a mammal. Exemplary biological samples include, but are not limited to, cell lysate, a cell culture, a cell line, a tissue, oral tissue, gastrointestinal tissue, an organ, an organelle, a biological fluid, a blood sample, a urine sample, a skin sample, and the like. In certain embodiments, biological samples include, but are not limited to, whole blood, partially purified blood, PBMCs, tissue biopsies, and the like.

The term "analyte" as used herein, refers to a known or unknown component of a sample.

The term "capture agent," as used herein, refers to an agent that binds an mRNA or protein through an interaction that is sufficient to permit the agent to bind and concentrate the mRNA or protein from a homogeneous mixture.

The term "probe" as used herein, refers to a capture agent that is directed to a specific target mRNA biomarker sequence. Accordingly, each probe of a probe set has a respective target mRNA biomarker. A probe/target mRNA duplex is a structure formed by hybridizing a probe to its target mRNA biomarker.

The term "nucleic acid probe" or "oligonucleotide probe" refers to a nucleic acid capable of binding to a target nucleic acid of complementary sequence, such as the mRNA biomarkers provided herein, through one or more types of chemical bonds, usually through complementary base pairing, usually through hydrogen bond formation. As used herein, a probe may include natural (e.g., A, G, C, or T) or modified bases (7-deazaguanosine, inosine, etc.). In addition, the bases in a probe may be joined by a linkage other than a phosphodiester bond, so long as it does not interfere with hybridization. It will be understood by one of skill in the art that probes may bind target sequences lacking complete complementarity with the probe sequence depending upon the stringency of the hybridization conditions. The probes are preferably directly labeled with isotopes, for example, chromophores, lumiphores, chromogens, or indirectly labeled with biotin to which a streptavidin complex may later bind. By assaying for the presence or absence of the probe, one can detect the presence or absence of a target mRNA biomarker of interest.

The term "stringent assay conditions" refers to conditions that are compatible to produce binding pairs of nucleic acids, e.g., probes and target mRNAs, of sufficient complementarity to provide for the desired level of specificity in the assay while being generally incompatible to the formation of binding pairs between binding members of insufficient complementarity to provide for the desired specificity. The term "stringent assay conditions" generally refers to the combination of hybridization and wash conditions.

A "label" or a "detectable moiety" in reference to a nucleic acid, refers to a composition that, when linked with a nucleic acid, renders the nucleic acid detectable, for example, by spectroscopic, photochemical, biochemical, immunochemical, or chemical means. Exemplary labels include, but are not limited to, radioactive isotopes, magnetic beads, metallic beads, colloidal particles, fluorescent dyes, enzymes, biotin, digoxigenin, haptens, and the like. A "labeled nucleic acid or oligonucleotide probe" is generally one that is bound, either covalently, through a linker or a chemical bond, or noncovalently, through ionic bonds, van der Waals forces, electrostatic attractions, hydrophobic interactions, or hydrogen bonds, to a label such that the presence of the nucleic acid or probe can be detected by detecting the presence of the label bound to the nucleic acid or probe.

The terms "polymerase chain reaction" or "PCR," as used herein generally refers to a procedure wherein small amounts of a nucleic acid, RNA and/or DNA, are amplified as described, for example, in U.S. Pat. No. 4,683,195 to Mullis. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.,* 51: 263 (1987); Erlich, ed., PCR Technology, (Stockton Press, NY, 1989).

The term "cycle number" or "CT" when used herein in reference to PCR methods, refers to the PCR cycle number at which the fluorescence level passes a given set threshold level. The CT measurement can be used, for example, to approximate levels of mRNA in an original sample. The CT measurement is often used in terms of "dCT" or the "difference in the CT" score, when the CT of one nucleic acid is subtracted from the CT of another nucleic acid.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The term "TCF" or "T-cell factor" refers to a member of TCF/LEF family proteins, or a variant thereof. The term "TCF variant" is intended to include proteins substantially homologous to a native TCF, i.e., proteins having one or more naturally or non-naturally occurring amino acid deletions, insertions, or substitutions (e.g., TCF derivatives, homologs, and fragments), as compared to the amino acid sequence of a native TCF. The amino acid sequence of a TCF variant is at least about 80% identical, at least about 90% identical, or at least about 95% identical to a native TCF. Examples of TCF/LEF family proteins include, but are not limited to, TCF-1 (TCF7), LEF-1, TCF-3 (TCF7L1), and TCF-4 (TCF7L2). Human TCF-4 includes hTCF-4A, hTCF-4B, hTCF-4C, hTCF-4D, hTCF-4E, hTCF-4F, hTCF-4G, hTCF-4H, hTCF-4I, hTCF-4J, hTCF-4K, hTCF-4L, hTCF-4M, and hTCF-4X. TCF-4 also refers to a protein encoded by TCF7L2 gene or Gene 6934 in humans (Castrop et al., *Nucleic Acids Res.* 1992, 20, 611, the disclosure of which is incorporated by reference in its entirety).

The term "WISP2" or "WNT1-inducible-signaling pathway protein 2" refers to a protein encoded by the WISP2 gene in humans, or a variant thereof. See, Pennica et al., *Proc. Natl. Acad. Sci. USA* 1999, 95, 14717-14722, the disclosure of which is incorporated by reference in its entirety. The term "WISP2 variant" is intended to include proteins substantially homologous to a native WISP2, i.e., proteins having one or more naturally or non-naturally occurring amino acid deletions, insertions, or substitutions (e.g., WISP2 derivatives, homologs, and fragments), as compared to the amino acid sequence of a native WISP2. The amino acid sequence of a WISP2 variant is at least about 80% identical, at least about 90% identical, or at least about 95% identical to a native WISP2.

The term "ASPH" or "aspartyl/asparaginyl beta-hydroxylase" refers to an enzyme that is encoded in humans by the ASPH gene, or a variant thereof. See, Korioth et al., *Gene* 1995, 150, 295-299; and Lim et al., *Gene* 2000, 255, 35-42; the disclosure of each of which is incorporated by reference in its entirety. The term "ASPH variant" is intended to include proteins substantially homologous to a native ASPH, i.e., proteins having one or more naturally or non-naturally occurring amino acid deletions, insertions, or substitutions (e.g., ASPH derivatives, homologs, and fragments), as compared to the amino acid sequence of a native ASPH. The amino acid sequence of a ASPH variant is at least about 80% identical, at least about 90% identical, or at least about 95% identical to a native ASPH.

The term "IRS1" or "insulin receptor substrate 1" refers to a protein that is encoded in humans by the ISR-1 gene, or a variant thereof. See, Sun et al., *Nature* 1991, 352, 73-77; the disclosure of which is incorporated by reference in its entirety. The term "IRS1 variant" is intended to include proteins substantially homologous to a native IRS1, i.e., proteins having one or more naturally or non-naturally occurring amino acid deletions, insertions, or substitutions (e.g., IRS1 derivatives, homologs, and fragments), as compared to the amino acid sequence of a native IRS1. The amino acid sequence of an IRS1 variant is at least about 80% identical, at least about 90% identical, or at least about 95% identical to a native IRS1.

The term "MAPK12" or "mitogen-activated protein kinase 12," also known as extracellular signal-regulated kinase 6 (ERK6) or stress-activated protein kinase 3 (SAPK3), refers to an enzyme that is encoded in humans by the MAPK12 gene, or a variant thereof. The term "MAPK12 variant" is intended to include proteins substantially homologous to a native MAPK12, i.e., proteins having one or more naturally or non-naturally occurring amino acid deletions, insertions, or substitutions (e.g., MAPK12 derivatives, homologs, and fragments), as compared to the amino acid sequence of a native MAPK12. The amino acid sequence of a MAPK12 variant is at least about 80% identical, at least about 90% identical, or at least about 95% identical to a native MAPK12.

The term "JAG1" refers to a Jagged-1 protein or a variant thereof. The term "JAG1 variant" is intended to include proteins substantially homologous to a native JAG1, i.e., proteins having one or more naturally or non-naturally occurring amino acid deletions, insertions, or substitutions (e.g., JAG1 derivatives, homologs, and fragments), as compared to the amino acid sequence of a native JAG1. The amino acid sequence of an JAG1 variant is at least about 80% identical, at least about 90% identical, or at least about 95% identical to a native JAG1.

The term "CLDN2" or "claudin 2" refers to a protein that is encoded in humans by the CLDN2 gene, or a variant thereof. CLDN2 is known to decrease the tightness of the epithelial barrier. LEF-1 and TCF-4 bind to CLDN2 promoter and increase CLDN2 expression in mouse mammary epithelial C57 cells expressing Wnt-1. (Mankertz et al., *Biochem Biophys Res Commun* 2004; 314: 1001-7). CLDN2 overexpresses in colorectal cancer (Kinugasa et al., *Anticancer Res* 2007; 27: 3729-34), and increases tumorigenicity of colon cancer cells. The term "CLDN2 variant" is intended to include proteins substantially homologous to a native CLDN2, i.e., proteins having one or more naturally or non-naturally occurring amino acid deletions, insertions, or substitutions (e.g., CLDN2 derivatives, homologs, and fragments), as compared to the amino acid sequence of a native CLDN2. The amino acid sequence of a CLDN2 variant is at least about 80% identical, at least about 90% identical, or at least about 95% identical to a native CLDN2.

The term "STK17B" or "serine/threonine kinase 17b" refers to an enzyme that is encoded in humans by the STK17B gene, or a variant thereof. DAP kinase-related apoptosis-inducing kinase 2 and STK17B have been reported to induce apoptosis. (Sanjo et al., *J Biol Chem* 1998; 273: 29066-71). The term "STK17B variant" is intended to include proteins substantially homologous to a native STK17B, i.e., proteins having one or more naturally or non-naturally occurring amino acid deletions, insertions, or substitutions (e.g., STK17B derivatives, homologs, and fragments), as compared to the amino acid sequence of a native STK17B. The amino acid sequence of a STK17B variant is at least about 80% identical, at least about 90% identical, or at least about 95% identical to a native STK17B.

The term "SPP1" or "secreted phosphoprotein 1" refers to a protein that is encoded in humans by the SPP1 gene, or a variant thereof. SPP1 codes osteopontin (OPN). SPP1 is known to play a role in bone remodeling, anti-apoptosis, cell adhesion, and cell migration. SPP1 is a downstream target gene of TCF-4 in a rat breast epithelial cell line (El-Tanani et al., *Cancer Res* 2001; 61: 5619-29) and in breast cancer cell lines. OPN is overexpressed in colon cancer, gastric cancer, lung cancer, breast carcinoma, HCC, bladder cancer, prostate cancer, ovarian cancer, thyroid cancer, and melanoma. OPN overexpression is significantly associated with the metastatic potential of HCC cell lines, and with a poor prognosis for patients with HCC. OPN plasma level is reported to get elevated in HCC patients. Especially, sensitivity of OPN is regarded to be higher than that of other markers. The term "SPP1 variant" is intended to include proteins substantially homologous to a native SPP1, i.e., proteins having one or more naturally or non-naturally occurring amino acid deletions, insertions, or substitutions (e.g., SPP1 derivatives, homologs, and fragments), as compared to the amino acid sequence of a native SPP1. The amino acid sequence of a SPP1 variant is at least about 80% identical, at least about 90% identical, or at least about 95% identical to a native SPP1.

The term "AXIN2" refers to a protein that is encoded in humans by the AXIN2 gene, or a variant thereof. AXIN2 is a member of β-catenin destruction complex. AXIN2 is known to be a downstream target gene in human colon cancer (Jho et al., *Mol Cell Biol* 2002; 22: 1172-83), controlling Wnt signal through a negative feedback loop. AXIN2 mutation in HCC is reported to be about 2.7% and 37.5%. The term "AXIN2 variant" is intended to include proteins substantially homologous to a native AXIN2, i.e., proteins having one or more naturally or non-naturally occurring amino acid deletions, insertions, or substitutions (e.g., AXIN2 derivatives, homologs, and fragments), as compared to the amino acid sequence of a native AXIN2. The amino acid sequence of a AXIN2 variant is at least about 80% identical, at least about 90% identical, or at least about 95% identical to a native AXIN2.

The term "MMP7" or "matrix metallopeptidase 7" refers to a protein that is encoded in humans by the MMP7 gene, or a variant thereof. MMP7 is known to degrade components of the basement membrane (such as laminin, type IV collagen, and entactin). MMP7 is known to be a downstream target gene in colorectal cancer. (Schmalhofer et al., *Methods Mol Biol* 2008; 468: 111-28). MMP7 may be overexpressed in esophageal cancer, colorectal cancer, gastric cancer, HCC, pancreatic cancer, renal cell carcinoma, and prostate cancer. The term "MMP7 variant" is intended to include proteins substantially homologous to a native MMP7, i.e., proteins having one or more naturally or non-naturally occurring amino acid deletions, insertions, or substitutions (e.g., MMP7 derivatives, homologs, and fragments), as compared to the amino acid sequence of a native MMP7. The amino acid sequence of a MMP7 variant is at least about 80% identical, at least about 90% identical, or at least about 95% identical to a native MMP7.

The term "CADM1" or "cell adhesion molecule 1" refers to a protein that is encoded in humans by the CADM1 gene, or a variant thereof. CADM1 is known to be a tumor suppressor in lung cancer 1. It was reported that CADM1 mediates intracellular adhesion. CADM1 functions as a tumor-suppressor gene, and may be downregulated in lung cancer, HCC, and pancreatic cancer. (Kuramochi et al., *Nat Genet* 2001; 27:427-30). The term "CADM1 variant" is intended to include proteins substantially homologous to a native CADM1, i.e., proteins having one or more naturally or non-naturally occurring amino acid deletions, insertions, or substitutions (e.g., CADM1 derivatives, homologs, and fragments), as compared to the amino acid sequence of a native CADM1. The amino acid sequence of a CADM1 variant is at least about 80% identical, at least about 90% identical, or at least about 95% identical to a native CADM1.

The term "ANXA1" or "annexin A1" refers to a protein that is encoded in humans by the ANXA1 gene, or a variant thereof. A member of Ca-dependent phospholipid-binding proteins, ANXA1 overexpression is known to enhance metastasis through NF-κB activation in breast cancer cells. It is also reported that ANXA1 regulates cell proliferation by inhibition of cyclin D1 through ERK1/2 MAPK signaling in non-cancer cells. (Alldridge et al., *Exp Cell Res* 2003; 290: 93-107). The term "ANXA1 variant" is intended to include proteins substantially homologous to a native ANXA1, i.e., proteins having one or more naturally or non-naturally occurring amino acid deletions, insertions, or substitutions (e.g., ANXA1 derivatives, homologs, and fragments), as compared to the amino acid sequence of a native ANXA1. The amino acid sequence of a ANXA1 variant is at least about 80% identical, at least about 90% identical, or at least about 95% identical to a native ANXA1.

The term "CAMK2N1" or "calcium/calmodulin-dependent protein kinase inhibitor 1" refers to a protein that is encoded in humans by the CAMK2N1 gene, or a variant thereof. CAMK2N1 is a member of CAMK2N family and potentially may be a biomarker for prostate cancer. The term "CAMK2N1 variant" is intended to include proteins substantially homologous to a native CAMK2N1, i.e., proteins having one or more naturally or non-naturally occurring amino acid deletions, insertions, or substitutions (e.g., CAMK2N1 derivatives, homologs, and fragments), as compared to the amino acid sequence of a native CAMK2N1. The amino acid sequence of a CAMK2N1 variant is at least about 80% identical, at least about 90% identical, or at least about 95% identical to a native CAMK2N1.

The term "PLCD4" or "phospholipase C, delat 4" refers to a protein that is encoded in humans by the PLCD4 gene, or a variant thereof. It was reported that PLCD4 overexpression upregulates ErbB1/2 expression, ERK signaling pathway, and proliferation in breast cancer cells. (Leung et al., *Mol Cancer* 2004; 3: 15). PCLD4 is known to be overexpressed in regenerating liver than in normal resting liver and in tumor cells such as hepatoma. (Liu et al., *J Biol Chem* 1996; 271: 355-60). The term "PLCD4 variant" is intended to include proteins substantially homologous to a native PLCD4, i.e., proteins having one or more naturally or non-naturally occurring amino acid deletions, insertions, or substitutions (e.g., PLCD4 derivatives, homologs, and fragments), as compared to the amino acid sequence of a native PLCD4. The amino acid sequence of a PLCD4 variant is at least about 80% identical, at least about 90% identical, or at least about 95% identical to a native PLCD4.

The term "GPR56" or "G protein-coupled receptor 56" refers to a protein that is encoded in humans by the GPR56 gene, or a variant thereof. GPR56 belongs to orphan G-protein coupled receptor (GPR) family. GPR56 is known to inhibit melanoma tumor growth and metastasis. (Xu, *Adv Exp Med Biol* 2010; 706: 98-108). It was reported that GPR56 is upregulated in tumor tissue compared to normal tissue, and significantly correlates with nodal metastasis and tumor invasion in esophageal carcinoma. The term "GPR56 variant" is intended to include proteins substantially homologous to a native GPR56, i.e., proteins having one or more naturally or non-naturally occurring amino acid deletions, insertions, or substitutions (e.g., GPR56 derivatives, homologs, and fragments), as compared to the amino acid sequence of a native GPR56. The amino acid sequence of a GPR56 variant is at least about 80% identical, at least about 90% identical, or at least about 95% identical to a native GPR56.

The term "CD24" refers to a glycoprotein expressed at the surface of most B lymphocytes and differentiating neuroblasts. CD24 is a downstream target gene in breast cancer. (Shulewitz et al., *Oncogene* 2006; 25: 4361-9). CD24 is known to be associated with anti-apoptosis, tumor growth and metastasis, and is upregulated in B-cell lymphoma, renal cell carcinoma, lung cancer, HCC, pancreatic cancer, and colorectal cancer. The term "CD24 variant" is intended to include proteins substantially homologous to a native CD24, i.e., proteins having one or more naturally or non-naturally occurring amino acid deletions, insertions, or substitutions (e.g., CD24 derivatives, homologs, and fragments), as compared to the amino acid sequence of a native CD24. The amino acid sequence of a CD24 variant is at least about 80% identical, at least about 90% identical, or at least about 95% identical to a native CD24.

The practice of the embodiments provided herein will employ, unless otherwise indicated, conventional techniques of molecular biology, microbiology, and immunology, which are within the skill of those working in the art. Such techniques are explained fully in the literature. Examples of particularly suitable texts for consultation include the following: Sambrook et al., *Molecular Cloning; A Laboratory Manual* (2d ed.), 1989; Glover, ed. *DNA Cloning*, Volumes I and II, 1985; Gait, ed., *Oligonucleotide Synthesis*, 1984; Hames & Higgins, eds. *Nucleic Acid Hybridization*, 1984; Hames &. Higgins, eds., *Transcription and Translation*, 1984; Freshney, ed., *Animal Cell Culture*, 1986; *Immobilized Cells and Enzymes*, IRL Press, 1986; *Immunochemical Methods in Cell and Molecular Biology* (Academic Press, London); Scopes, *Protein Purification: Principles and Practice* (2d ed.; Springer Verlag, N.Y.), 1987; and Weir and Blackwell, eds. *Handbook of Experimental Immunology*, Volumes I-IV, 1986.

4.3 BIOMARKERS

A biological marker or "biomarker" is a substance, the change and/or the detection of which indicates a particular biological state, such as, for example, the responsiveness of a disease, e.g., hepatocellular carcinoma, to a given treatment, e.g., a treatment by a treatment compound, e.g., thalidomide, lenalidomide, pomalidomide, or 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

In certain embodiments, the biomarker is a T-cell factor (TCF) or a variant thereof. In certain embodiments, the biomarker is TCF-1, LEF-1, TCF-3, TCF-4, or a variant thereof. In certain embodiments, the biomarker is TCF-1 or a variant thereof. In certain embodiments, the biomarker is LEF-1 or a variant thereof. In certain embodiments, the biomarker is TCF-3 or a variant thereof. In certain embodiments, the biomarker is TCF-4 or a variant thereof.

In certain embodiments, the biomarker is an isoform of TCF-4. In certain embodiments, the biomarker is TCF-4A, TCF-4B, TCF-4C, TCF-4D, TCF-4E, TCF-4F, TCF-4G, TCF-4H, TCF-4I, TCF-4J, TCF-4K, TCF-4L, TCF-4M, TCF-4X, or a variant thereof. In certain embodiments, the biomarker is TCF-4A or a variant. In certain embodiments, the biomarker is TCF-4B or a variant. In certain embodiments, the biomarker is TCF-4C or a variant. In certain embodiments, the biomarker is TCF-4D or a variant. In certain embodiments, the biomarker is TCF-4E or a variant. In certain embodiments, the biomarker is TCF-4F or a variant. In certain embodiments, the biomarker is TCF-4G or a variant. In certain embodiments, the biomarker is TCF-4H or a variant. In certain embodiments, the biomarker is TCF-4I or a variant. In certain embodiments, the biomarker is TCF-4J or a variant. In certain embodiments, the biomarker is TCF-4K or a variant. In certain embodiments, the biomarker is TCF-4L or a variant. In certain embodiments, the biomarker is TCF-4M or a variant. In certain embodiments, the biomarker is TCF-4X or a variant. In certain embodiments, the one or more biomarkers employed herein are TCF-4C, TCF-4J, and TCF-4L.

TCF-4 isoforms are the basis for the transcriptional regulation of genes activated by WnVB-catenin signaling in combination with β-catenin and other proteins. These transcription factors also regulate insulin/IGF-1 growth factor as well as Notch signaling pathways all of which are highly active in over 95% of hepatitis B virus (HBV) and hepatitis C virus (HCV) related hepatocellular carcinoma. It is disclosed herein that certain TCF-4 isoforms regulate genes that are involved in cell proliferation, cell migration, and invasion as well as cellular transformation as measured by colony formation in soft agar and tumor growth in immune deficient nude mice.

In certain embodiments, the biomarker is a human T-cell factor (hTCF) or a variant thereof. In certain embodiments, the biomarker is hTCF-1, hLEF-1, hTCF-3, hTCF-4, or a variant thereof. In certain embodiments, the biomarker is hTCF-1 or a variant thereof. In certain embodiments, the biomarker is hLEF-1 or a variant thereof. In certain embodiments, the biomarker is hTCF-3 or a variant thereof. In certain embodiments, the biomarker is hTCF-4 or a variant thereof.

In certain embodiments, the biomarker is an isoform of hTCF-4. In certain embodiments, the biomarker is hTCF-4A, hTCF-4B, hTCF-4C, hTCF-4D, hTCF-4E, hTCF-4F, hTCF-4G, hTCF-4H, hTCF-4I, hTCF-4J, hTCF-4K, hTCF-4L, hTCF-4M, hTCF-4X, or a variant thereof. In certain embodiments, the biomarker is hTCF-4A or a variant. In certain embodiments, the biomarker is hTCF-4B or a variant. In certain embodiments, the biomarker is hTCF-4C or a variant. In certain embodiments, the biomarker is hTCF-4D or a variant. In certain embodiments, the biomarker is hTCF-4E or a variant. In certain embodiments, the biomarker is hTCF-4F or a variant. In certain embodiments, the biomarker is hTCF-4G or a variant. In certain embodiments, the biomarker is hTCF-4H or a variant. In certain embodiments, the biomarker is hTCF-4I or a variant. In certain embodiments, the biomarker is hTCF-4J or a variant. In certain embodiments, the biomarker is hTCF-4K or a variant. In certain embodiments, the biomarker is hTCF-4L or a variant. In certain embodiments, the biomarker is hTCF-4M or a variant. In certain embodiments, the biomarker is hTCF-4X or a variant. In certain embodiments, the one or more biomarkers employed herein are hTCF-4C, hTCF-4J, and hTCF-4L.

In certain embodiments, the biomarker is an mRNA of TCF or a variant thereof. In certain embodiments, the biomarker is an mRNA of TCF-1, LEF-1, TCF-3, TCF-4, or a variant thereof. In certain embodiments, the biomarker is an mRNA of TCF-1 or a variant thereof. In certain embodiments, the biomarker is an mRNA of LEF-1 or a variant thereof. In certain embodiments, the biomarker is an mRNA of TCF-3 or a variant thereof. In certain embodiments, the biomarker is an mRNA of TCF-4 or a variant thereof.

In certain embodiments, the biomarker is an mRNA of an isoform of TCF-4. In certain embodiments, the biomarker is an mRNA of TCF-4A, TCF-4B, TCF-4C, TCF-4D, TCF-4E, TCF-4F, TCF-4G, TCF-4H, TCF-4I, TCF-4J, TCF-4K, TCF-4L, TCF-4M, TCF-4X, or a variant thereof. In certain embodiments, the biomarker is an mRNA of TCF-4A or a variant. In certain embodiments, the biomarker is an mRNA of TCF-4B or a variant. In certain embodiments, the biomarker is an mRNA of TCF-4C or a variant. In certain embodiments, the biomarker is an mRNA of TCF-4D or a variant. In certain embodiments, the biomarker is an mRNA of TCF-4E or a variant. In certain embodiments, the biomarker is an mRNA of TCF-4F or a variant. In certain embodiments, the biomarker is an mRNA of TCF-4G or a variant. In certain embodiments, the biomarker is an mRNA of TCF-4H or a variant. In certain embodiments, the biomarker is an mRNA of TCF-4I or a variant. In certain embodiments, the biomarker is an mRNA of TCF-4J or a variant. In certain embodiments, the biomarker is an mRNA of TCF-4K or a variant. In certain embodiments, the biomarker is an mRNA of TCF-4L or a variant. In certain embodiments, the biomarker is an mRNA of TCF-4M or a variant. In certain embodiments, the biomarker is an mRNA of TCF-4X or a variant. In certain embodiments, the one or more biomarkers employed herein are mRNAs of TCF-4C, TCF-4J, and TCF-4L.

In certain embodiments, the biomarker is an mRNA of a human T-cell factor (hTCF) or a variant thereof. In certain embodiments, the biomarker is an mRNA of hTCF-1, hLEF-1, hTCF-3, hTCF-4, or a variant thereof. In certain embodiments, the biomarker is hTCF-1 or a variant thereof. In certain embodiments, the biomarker is an mRNA of hLEF-1 or a variant thereof. In certain embodiments, the biomarker is an mRNA of hTCF-3 or a variant thereof. In certain embodiments, the biomarker is an mRNA of hTCF-4 or a variant thereof.

In certain embodiments, the biomarker is an mRNA of an isoform of hTCF-4. In certain embodiments, the biomarker is an mRNA of hTCF-4A, hTCF-4B, hTCF-4C, hTCF-4D, hTCF-4E, hTCF-4F, hTCF-4G, hTCF-4H, hTCF-4I, hTCF-4J, hTCF-4K, hTCF-4L, hTCF-4M, hTCF-4X, or a variant thereof. In certain embodiments, the biomarker is an mRNA of hTCF-4A or a variant. In certain embodiments, the biomarker is an mRNA of hTCF-4B or a variant. In certain embodiments, the biomarker is an mRNA of hTCF-4C or a variant. In certain embodiments, the biomarker is an mRNA of hTCF-4D or a variant. In certain embodiments, the biomarker is hTCF-4E or a variant. In certain embodiments, the biomarker is an mRNA of hTCF-4F or a variant. In certain embodiments, the biomarker is an mRNA of hTCF-4G or a variant. In certain embodiments, the biomarker is an mRNA of hTCF-4H or a variant. In certain embodiments, the biomarker is an mRNA of hTCF-4I or a variant. In certain embodiments, the biomarker is an mRNA of hTCF-4J or a variant. In certain embodiments, the biomarker is an mRNA of hTCF-4K or a variant. In certain embodiments, the biomarker is an mRNA of hTCF-4L or a variant. In certain embodiments, the biomarker is an mRNA of hTCF-4M or a variant. In certain embodiments, the biomarker is an mRNA of hTCF-4X or a variant. In certain embodiments, the one or more biomarkers employed herein are mRNAs of hTCF-4C, hTCF-4J, and hTCF-4L.

In certain embodiments, the biomarker is a cDNA of TCF or a variant thereof. In certain embodiments, the biomarker is a cDNA of TCF-1, LEF-1, TCF-3, TCF-4, or a variant thereof. In certain embodiments, the biomarker is a cDNA of TCF-1 or a variant thereof. In certain embodiments, the biomarker is a cDNA of LEF-1 or a variant thereof. In certain embodiments, the biomarker is a cDNA of TCF-3 or a variant thereof. In certain embodiments, the biomarker is a cDNA of TCF-4 or a variant thereof.

In certain embodiments, the biomarker is a cDNA of an isoform of TCF-4. In certain embodiments, the biomarker is a cDNA of TCF-4A, TCF-4B, TCF-4C, TCF-4D, TCF-4E, TCF-4F, TCF-4G, TCF-4H, TCF-4I, TCF-4J, TCF-4K, TCF-4L, TCF-4M, TCF-4X, or a variant thereof. In certain embodiments, the biomarker is a cDNA of TCF-4A or a variant. In certain embodiments, the biomarker is a cDNA of TCF-4B or a variant. In certain embodiments, the biomarker is a cDNA of TCF-4C or a variant. In certain embodiments, the biomarker is a cDNA of TCF-4D or a variant. In certain embodiments, the biomarker is a cDNA of TCF-4E or a variant. In certain embodiments, the biomarker is a cDNA of TCF-4F or a variant. In certain embodiments, the biomarker is a cDNA of TCF-4G or a variant. In certain embodiments, the biomarker is a cDNA of TCF-4H or a variant. In certain embodiments, the biomarker is a cDNA of TCF-4I or a variant. In certain embodiments, the biomarker is a cDNA of TCF-4J or a variant. In certain embodiments, the biomarker is a cDNA of TCF-4K or a variant. In certain embodiments, the biomarker is a cDNA of TCF-4L or a variant. In certain embodiments, the biomarker is a cDNA of TCF-4M or a variant. In certain embodiments, the biomarker is a cDNA of TCF-4X or a variant. In certain embodiments, the one or more biomarkers employed herein are cDNAs of TCF-4C, TCF-4J, and TCF-4L.

In certain embodiments, the biomarker is a cDNA of a human T-cell factor (hTCF) or a variant thereof. In certain embodiments, the biomarker is a cDNA of hTCF-1, hLEF-1, hTCF-3, hTCF-4, or a variant thereof. In certain embodiments, the biomarker is hTCF-1 or a variant thereof. In certain embodiments, the biomarker is a cDNA of hLEF-1 or a variant thereof. In certain embodiments, the biomarker is a cDNA of hTCF-3 or a variant thereof. In certain embodiments, the biomarker is a cDNA of hTCF-4 or a variant thereof.

In certain embodiments, the biomarker is a cDNA of an isoform of hTCF-4. In certain embodiments, the biomarker is a cDNA of hTCF-4A, hTCF-4B, hTCF-4C, hTCF-4D, hTCF-4E, hTCF-4F, hTCF-4G, hTCF-4H, hTCF-4I, hTCF-4J, hTCF-4K, hTCF-4L, hTCF-4M, hTCF-4X, or a variant thereof. In certain embodiments, the biomarker is a cDNA of hTCF-4A or a variant. In certain embodiments, the biomarker is a cDNA of hTCF-4B or a variant. In certain embodiments, the biomarker is a cDNA of hTCF-4C or a variant. In certain embodiments, the biomarker is a cDNA of hTCF-4D or a variant. In certain embodiments, the biomarker is hTCF-4E or a variant. In certain embodiments, the biomarker is a cDNA of hTCF-4F or a variant. In certain embodiments, the biomarker is a cDNA of hTCF-4G or a variant. In certain embodiments, the biomarker is a cDNA of hTCF-4H or a variant. In certain embodiments, the biomarker is a cDNA of hTCF-4I or a variant. In certain embodiments, the biomarker is a cDNA of hTCF-4J or a variant. In certain embodiments, the biomarker is a cDNA of hTCF-4K or a variant. In certain embodiments, the biomarker is a cDNA of hTCF-4L or a variant. In certain embodiments, the biomarker is a cDNA of hTCF-4M or a variant. In certain embodiments, the biomarker is a cDNA of hTCF-4X or a variant. In certain embodiments, the one or more biomarkers employed herein are cDNAs of hTCF-4C, hTCF-4J, and hTCF-4L.

In certain embodiments, the biomarker is TCF-4J dependent target gene or the product thereof. TCF-4J dependent target genes include, but are not limited to, genes encoding WISP2, ASPH, IRS1, MAPK12, CLDN2, JAG1, GPR56, ANXA1, CAMK2N1, STK17B, SPP1, AXIN2, MMP7, CADM1, PLCD4 and CD24. Combinations of one or more of these TCF-4J target genes can also be used as a biomarker. One or more of these TCF-4J target genes can also optionally combined with any of the isoforms of TCF-4 and used as a biomarker.

In certain embodiments, the one or more biomarkers employed herein are TCF-4C, TCF-4J, TCF-4L, WISP2, ASPH, IRS1, MAPK12, CLDN2, JAG1, GPR56, ANXA1, CAMK2N1, STK17B, SPP1, AXIN2, MMP7, CADM1, PLCD4, CD24, or a combination thereof. In certain embodiments, the one or more biomarkers employed herein are hTCF-4C, hTCF-4J, hTCF-4L, WISP2, ASPH, IRS1, MAPK12, CLDN2, JAG1, GPR56, ANXA1, CAMK2N1, STK17B, SPP1, AXIN2, MMP7, CADM1, PLCD4, CD24, or a combination thereof. In certain embodiments, the one or more biomarkers employed herein are mRNAs of TCF-4C, TCF-4J, TCF-4L, WISP2, ASPH, IRS1, MAPK12, CLDN2, JAG1, GPR56, ANXA1, CAMK2N1, STK17B, SPP1, AXIN2, MMP7, CADM1, PLCD4, CD24, or a combination thereof. In certain embodiments, the one or more biomarkers employed herein are mRNAs of hTCF-4C, hTCF-4J, hTCF-4L, WISP2, ASPH, IRS1, MAPK12, CLDN2, JAG1, GPR56, ANXA1, CAMK2N1, STK17B, SPP1, AXIN2, MMP7, CADM1, PLCD4, CD24, or a combination thereof. In certain embodiments, the one or more biomarkers employed herein are cDNAs of TCF-4C, TCF-4J, TCF-4L, WISP2, ASPH, IRS1, MAPK12, CLDN2, JAG1, GPR56, ANXA1, CAMK2N1, STK17B, SPP1, AXIN2, MMP7, CADM1, PLCD4, CD24, or a combination thereof. In certain embodiments, the one or more biomarkers employed herein are cDNAs of hTCF-4C, hTCF-4J, hTCF-4L, WISP2, ASPH, IRS1, MAPK12, CLDN2, JAG1, GPR56, ANXA1, CAMK2N1, STK17B, SPP1, AXIN2, MMP1, CADM1, PLCD4, CD24, or a combination thereof.

In certain embodiments, the one or more biomarkers employed herein are TCF-4, WISP2, ASPH, IRS1, MAPK12, JAG1, or a combination thereof. In certain embodiments, the one or more biomarkers employed herein are mRNAs of TCF-4, WISP2, ASPH, IRS1, MAPK12, JAG1, or a combination thereof. In certain embodiments, the one or more biomarkers employed herein are cDNAs of TCF-4, WISP2, ASPH, IRS1, MAPK12, JAG1, or a combination thereof.

In certain embodiments, the one or more biomarkers employed herein are CLDN2, ASPH, JAG1, GPR56, ANXA1, CAMK2N1, or a combination thereof. In certain embodiments, the one or more biomarkers employed herein are mRNAs of CLDN2, ASPH, JAG1, GPR56, ANXA1, CAMK2N1, or a combination thereof. In certain embodiments, the one or more biomarkers employed herein are cDNAs of CLDN2, ASPH, JAG1, GPR56, ANXA1, CAMK2N1, or a combination thereof.

In certain embodiments, the level of the biomarker provided herein correlates with or is indicative of the responsiveness of a disease (e.g., hepatocellular carcinoma) to a treatment, e.g., a treatment by a treatment compound, e.g., thalidomide, lenalidomide, pomalidomide, or 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

In certain embodiments, the biomarker is an mRNA. In certain embodiments, the biomarker is a cDNA. The level of the biomarker can be determined using the methods provided herein.

In certain embodiments, the biomarker is a protein. When a biomarker is a polypeptide, protein, or peptide, the level of the biomarker can be measured by determining the protein level, the mRNA level, or the enzymatic activity of the biomarker. The level of the biomarker can be determined using the methods provided herein.

The reference level can be determined by a plurality of methods. In certain embodiments, the reference level is one that a treatment decision is made based on whether a subject having or suspected of having hepatocellular carcinoma has the level of the biomarker above the reference level. Subjects who have a level of the biomarker higher than the reference level have a different probability of responsiveness to the treatment than subjects who have a level of the biomarker lower than the reference level. In certain embodiments, the reference level is measured simultaneously with the biological sample from the subject. In certain embodiments, the reference level is predetermined.

In certain embodiments, the reference level is determined from a sample from the same subject that contains no hepatocellular carcinoma cells. In certain embodiments, the reference level is determined from a sample from a group of subjects that contains no hepatocellular carcinoma cells. In certain embodiments, the reference level is determined from a sample from a group of subjects who do not have hepatocellular carcinoma. An increased level of the biomarker correlates positively with increased responsiveness of the subject to a treatment by a treatment compound, e.g., thalidomide, lenalidomide, pomalidomide, or 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

In certain embodiments, the control sample is a sample containing no hepatocellular carcinoma cells from the same subject. In certain embodiments, the control sample is a sample of liver cells containing no hepatocellular carcinoma cells from the same subject. In certain embodiments, the control sample is a sample containing no hepatocellular carcinoma cells from a group of subjects. In certain embodiments, the control sample is a sample of liver cells containing no hepatocellular carcinoma cells from a group of subjects. In certain embodiments, the control sample is a sample from a subject having no hepatocellular carcinoma. In certain embodiments, the control sample is a sample of liver cells from a subject having no hepatocellular carcinoma. In certain embodiments, the control sample is a sample from a group of subjects having no hepatocellular carcinoma. In certain embodiments, the control sample is a sample of liver cells from a group of subjects having no hepatocellular carcinoma. An increased level of the one or more biomarkers as compared with the level of the control sample correlates positively with increased responsiveness of the subject to a treatment by a treatment compound, e.g., thalidomide, lenalidomide, pomalidomide, or 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

In certain embodiments, the biomarkers provided herein are determined individually. In certain embodiments, two or more of the biomarkers provided herein are determined simultaneously.

In certain embodiments, the level of a biomarker nucleic acid or polypeptide provided herein is measured in a biological sample from a subject, e.g., a hepatocellular carcinoma cell containing-sample from the subject. In certain embodiments, an affinity binding assay is used to measure the level of the biomarker polypeptide. The affinity binding assays that are applicable for use in the methods provided herein include both soluble and solid phase assays.

An example of a soluble phase affinity binding assay is immunoprecipitation using a biomarker binding agent, e.g., an antibody reactive with the biomarker polypeptide. Examples of solid phase affinity binding assays include immunohistochemical binding assays and immunoaffinity binding assays. Examples of immunoaffinity binding assays include, but are not limited to, immunohistochemistry methods, immunoblot methods, ELISA and radioimmunoassay (RIA).

An antibody useful in the methods provided herein includes a polyclonal and monoclonal antibodies. An antibody useful in the methods provided herein includes naturally occurring antibodies as well as non-naturally occurring antibodies, e.g., single chain antibodies, chimeric antibodies, bifunctional antibodies, humanized antibodies, and antigen-binding fragments thereof.

The biological sample can be liver tissue or a fluid such as blood, serum, or urine. In certain embodiments, the sample of cells from a subject is obtained via biopsy. Once a level of a biomarker is determined, this value can be correlated with clinical data on the patient from whom the sample is derived, e.g., the responsiveness of a patient to a given treatment.

In certain embodiments, the sample of cells from a subject is obtained via biopsy.

In certain embodiments, the level of only one of the biomarkers is monitored. In certain embodiments, the levels of two or more of the biomarkers are monitored simultaneously.

4.3.1 Use of Biomarkers for Identifying a Subject for Treatment

Based, in part, on the finding that detectable increase or decrease in certain biomarkers are observed in subjects with hepatocellular carcinoma who are responsive to a given treatment (e.g., a treatment by a treatment compound, e.g., thalidomide, lenalidomide, pomalidomide, or 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof), the levels of these biomarkers may be used for identifying a subject having hepatocellular carcinoma (e.g., poorly differentiated HCC) for the treatment by a treatment compound provided herein.

In one embodiment, provided herein is a method of identifying a subject having hepatocellular carcinoma who is likely to be responsive to a treatment compound, comprising:
a) determining the level of a biomarker in a hepatocellular carcinoma cell-containing sample from the subject; and
b) comparing the level of the biomarker in the sample to a reference level of the biomarker; wherein the subject is likely to be responsive to the treatment if the level of the biomarker in the sample of the subject is higher than the reference level of the biomarker.

In another embodiment, provided herein is a method of identifying a subject having poorly differentiated hepatocellular carcinoma who is likely to be responsive to a treatment compound, comprising:
a) determining the level of a biomarker in a hepatocellular carcinoma cell-containing sample from the subject; and
b) comparing the level of the biomarker in the sample to a reference level of the biomarker; wherein the subject is likely to be responsive to the treatment if the level of the biomarker in the sample of the subject is higher than the reference level of the biomarker.

In yet another embodiment, provided herein is a method of identifying a subject having hepatocellular carcinoma who is likely to be responsive to a treatment compound, comprising:
a) obtaining a biological sample from the subject;
b) determining the level of a biomarker in the sample; and
c) comparing the level of the biomarker in the sample to a reference level of the biomarker; wherein the subject is likely to be responsive to the treatment if the level of the biomarker in the sample of the subject is higher than the reference level of the biomarker.

In yet another embodiment, provided herein is a method of identifying a subject having poorly differentiated hepatocellular carcinoma who is likely to be responsive to a treatment compound, comprising:
a) obtaining a biological sample from the subject;
b) determining the level of a biomarker in the sample; and
c) comparing the level of the biomarker in the sample to a reference level of the biomarker; wherein the subject is likely to be responsive to the treatment if the level of the biomarker in the sample of the subject is higher than the reference level of the biomarker.

In certain embodiments, the reference level is determined from a non-hepatocellular carcinoma cell-containing sample from the same subject. In certain embodiments, the reference level is determined from a non-hepatocellular carcinoma cell-containing sample from a group of subjects.

In certain embodiments, the reference level is determined simultaneously with the hepatocellular carcinoma cell-containing sample. In certain embodiments, the reference level is determined independently from the hepatocellular carcinoma cell-containing sample.

In one embodiment, provided herein is a method of identifying a subject having hepatocellular carcinoma who is likely to be responsive to a treatment compound, comprising:
a) determining the level of a biomarker in a hepatocellular carcinoma cell-containing sample from the subject; and
b) determining the level of the biomarker in a control sample; wherein the subject is likely to be responsive to the treatment if the level of the biomarker in the sample of the subject is higher than the level of the biomarker in the control sample.

In another embodiment, provided herein is a method of identifying a subject having poorly differentiated hepatocellular carcinoma who is likely to be responsive to a treatment compound, comprising:
a) determining the level of a biomarker in a hepatocellular carcinoma cell-containing sample from the subject; and
b) determining the level of the biomarker in a control sample; wherein the subject is likely to be responsive to the treatment if the level of the biomarker in the sample of the subject is higher than the level of the biomarker in the control sample In yet another embodiment, provided herein is a method of identifying a subject having hepatocellular carcinoma who is likely to be responsive to a treatment compound, comprising:
a) obtaining a biological sample from the subject;
b) determining the level of a biomarker in the sample; and
c) determining the level of the biomarker in a control sample; wherein the subject is likely to be responsive to the treatment if the level of the biomarker in the sample of the subject is higher than the level of the biomarker in the control sample.

In yet another embodiment, provided herein is a method of identifying a subject having poorly differentiated hepatocellular carcinoma who is likely to be responsive to a treatment compound, comprising:
a) obtaining a biological sample from the subject;
b) determining the level of a biomarker in the sample; and
c) determining the level of the biomarker in a control sample; wherein the subject is likely to be responsive to the treatment if the level of the biomarker in the sample of the subject is higher than the level of the biomarker in the control sample.

In certain embodiments, the control sample is a non-hepatocellular carcinoma cell-containing sample from the same subject. In certain embodiments, the control sample is a non-hepatocellular carcinoma cell-containing sample from a group of subjects.

Thus, in one embodiment, provided herein is a method of identifying a subject having hepatocellular carcinoma who is likely to be responsive to a treatment compound, comprising:
   a) determining the level of a biomarker in a hepatocellular carcinoma cell-containing sample from the subject; and
   b) determining the level of the biomarker in a control sample from the subject; wherein the subject is likely to be responsive to the treatment if the level of the biomarker in the sample of the subject is higher than the level of the biomarker in the control sample.

In another embodiment, provided herein is a method of identifying a subject having poorly differentiated hepatocellular carcinoma who is likely to be responsive to a treatment compound, comprising:
   a) determining the level of a biomarker in a hepatocellular carcinoma cell-containing sample from the subject; and
   b) determining the level of the biomarker in a control sample from the subject; wherein the subject is likely to be responsive to the treatment if the level of the biomarker in the sample of the subject is higher than the level of the biomarker in the control sample In yet another embodiment, provided herein is a method of identifying a subject having hepatocellular carcinoma who is likely to be responsive to a treatment compound, comprising:
   a) obtaining a biological sample from the subject;
   b) determining the level of a biomarker in the sample; and
   c) determining the level of the biomarker in a control sample from the subject; wherein the subject is likely to be responsive to the treatment if the level of the biomarker in the sample of the subject is higher than the level of the biomarker in the control sample.

In yet another embodiment, provided herein is a method of identifying a subject having poorly differentiated hepatocellular carcinoma who is likely to be responsive to a treatment compound, comprising:
   a) obtaining a biological sample from the subject;
   b) determining the level of a biomarker in the sample; and
   c) determining the level of the biomarker in a control sample from the subject; wherein the subject is likely to be responsive to the treatment if the level of the biomarker in the sample of the subject is higher than the level of the biomarker in the control sample.

In certain embodiments, the level of the biomarker in a control sample is determined simultaneously with the hepatocellular carcinoma cell-containing sample. In certain embodiments, the level of the biomarker in a control sample is determined independently from the hepatocellular carcinoma cell-containing sample.

In certain embodiments, the methods provided herein are coupled with a treatment by a treatment compound provided herein, e.g., thalidomide, lenalidomide, pomalidomide, or 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

Thus, in one embodiment, provided herein is a method of treating hepatocellular carcinoma, comprising:
   (i) identifying a subject having hepatocellular carcinoma who is likely to be responsive to a treatment compound, comprising:
      a) determining the level of a biomarker in a hepatocellular carcinoma cell-containing sample from the subject; and
      b) comparing the level of the biomarker in the sample to a reference level of the biomarker; wherein the subject is likely to be responsive to the treatment if the level of the biomarker in the sample of the subject is higher than the reference level of the biomarker; and
   (ii) administering a therapeutically effective amount of the compound to the subject identified to be likely to be responsive to the treatment.

In another embodiment, provided herein is a method of treating poorly differentiated hepatocellular carcinoma, comprising:
   (i) identifying a subject having hepatocellular carcinoma who is likely to be responsive to a treatment compound, comprising:
      a) determining the level of a biomarker in a hepatocellular carcinoma cell-containing sample from the subject; and
      b) comparing the level of the biomarker in the sample to a reference level of the biomarker; wherein the subject is likely to be responsive to the treatment if the level of the biomarker in the sample of the subject is higher than the reference level of the biomarker; and
   (ii) administering a therapeutically effective amount of the compound to the subject identified to be likely to be responsive to the treatment.

In yet another embodiment, provided herein is a method of treating hepatocellular carcinoma, comprising:
   (i) identifying a subject having hepatocellular carcinoma who is likely to be responsive to a treatment compound, comprising:
      a) obtaining a biological sample from the subject;
      b) determining the level of a biomarker in the sample; and
      c) comparing the level of the biomarker in the sample to a reference level of the biomarker; wherein the subject is likely to be responsive to the treatment if the level of the biomarker in the sample of the subject is higher than the reference level of the biomarker; and
   (ii) administering a therapeutically effective amount of the compound to the subject identified to be likely to be responsive to the treatment.

In yet another embodiment, provided herein is a method of treating poorly differentiated hepatocellular carcinoma, comprising:
   (i) identifying a subject having hepatocellular carcinoma who is likely to be responsive to a treatment compound, comprising:
      a) obtaining a biological sample from the subject;
      b) determining the level of a biomarker in the sample; and
      c) comparing the level of the biomarker in the sample to a reference level of the biomarker; wherein the subject is likely to be responsive to the treatment if the level of the biomarker in the sample of the subject is higher than the reference level of the biomarker; and
   (ii) administering a therapeutically effective amount of the compound to the subject identified to be likely to be responsive to the treatment.

In yet another embodiment, provided herein is a method of treating hepatocellular carcinoma, comprising:
(i) identifying a subject having hepatocellular carcinoma who is likely to be responsive to a treatment compound, comprising:
a) determining the level of a biomarker in a hepatocellular carcinoma cell-containing sample from the subject; and
b) determining the level of the biomarker in a control sample; wherein the subject is likely to be responsive to the treatment if the level of the biomarker in the sample of the subject is higher than the level of the biomarker in the control sample; and
(ii) administering a therapeutically effective amount of the compound to the subject identified to be likely to be responsive to the treatment.

In yet another embodiment, provided herein is a method of treating poorly differentiated hepatocellular carcinoma, comprising:
(i) identifying a subject having hepatocellular carcinoma who is likely to be responsive to a treatment compound, comprising:
a) determining the level of a biomarker in a hepatocellular carcinoma cell-containing sample from the subject; and
b) determining the level of the biomarker in a control sample; wherein the subject is likely to be responsive to the treatment if the level of the biomarker in the sample of the subject is higher than the level of the biomarker in the control sample; and
(ii) administering a therapeutically effective amount of the compound to the subject identified to be likely to be responsive to the treatment.

In yet another embodiment, provided herein is a method of treating hepatocellular carcinoma, comprising:
(i) identifying a subject having hepatocellular carcinoma who is likely to be responsive to a treatment compound, comprising:
a) obtaining a biological sample from the subject;
b) determining the level of a biomarker in the sample; and
c) determining the level of the biomarker in a control sample; wherein the subject is likely to be responsive to the treatment if the level of the biomarker in the sample of the subject is higher than the level of the biomarker in the control sample; and
(ii) administering a therapeutically effective amount of the compound to the subject identified to be likely to be responsive to the treatment.

In yet another embodiment, provided herein is a method of treating poorly differentiated hepatocellular carcinoma, comprising:
(i) identifying a subject having hepatocellular carcinoma who is likely to be responsive to a treatment compound, comprising:
a) obtaining a biological sample from the subject;
b) determining the level of a biomarker in the sample; and
c) determining the level of the biomarker in a control sample; wherein the subject is likely to be responsive to the treatment if the level of the biomarker in the sample of the subject is higher than the level of the biomarker in the control sample; and
(ii) administering a therapeutically effective amount of the compound to the subject identified to be likely to be responsive to the treatment.

In certain embodiments, the biomarker is TCF, WISP2, ASPH, IRS1, MAPK12, JAG1, or a combination thereof. In certain embodiments, the biomarker is hTCF, WISP2, ASPH, IRS1, MAPK12, JAG1, or a combination thereof. In certain embodiments, the biomarker is TCF-4, WISP2, ASPH, IRS1, MAPK12, JAG1, or a combination thereof. In certain embodiments, the biomarker is hTCF-4, WISP2, ASPH, IRS1, MAPK12, JAG1, or a combination thereof.

In certain embodiments, the biomarker is TCF-4-A, TCF-4B, TCF-4C, TCF-4D, TCF-4E, TCF-4F, TCF-4G, TCF-4H, TCF-4I, TCF-4J, TCF-4K, TCF-4L, TCF-4M, TCF-4X, WISP2, ASPH, IRS1, MAPK12, JAG1, or a combination thereof. In certain embodiments, the biomarker is hTCF-4-A, hTCF-4B, hTCF-4C, hTCF-4D, hTCF-4E, hTCF-4F, hTCF-4G, hTCF-4H, hTCF-4I, hTCF-4J, hTCF-4K, hTCF-4L, hTCF-4M, hTCF-4X, WISP2, ASPH, IRS1, MAPK12, JAG1, or a combination thereof. In certain embodiments, the biomarker is TCF-4C, TCF-4J, TCF-4L, WISP2, ASPH, IRS1, MAPK12, JAG1, or a combination thereof. In certain embodiments, the biomarker is hTCF-4C, hTCF-4J, hTCF-4L, WISP2, ASPH, IRS1, MAPK12, JAG1, or a combination thereof. In certain embodiments, the biomarker is TCF-4C, TCF-4J, TCF-4L, or a combination thereof. In certain embodiments, the biomarker is hTCF-4C, hTCF-4J, hTCF-4L, or a combination thereof. In certain embodiments, the biomarker is a combination of TCF-4C, TCF-4J, and TCF-4L. In certain embodiments, the biomarker is a combination of hTCF-4C, hTCF-4J, hTCF-4L.

In certain embodiments, the biomarkers are used to identify a subject having hepatocellular carcinoma who is likely to be responsive to treatment by thalidomide, lenalidomide, pomalidomide, or 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

In certain embodiments, the biomarkers are used to identify a subject having poorly differentiated hepatocellular carcinoma who is likely to be responsive to treatment by thalidomide, lenalidomide, pomalidomide, or 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

In certain embodiments, the biomarkers are used to identify a subject having hepatocellular carcinoma who is likely to be responsive to treatment by thalidomide. In certain embodiments, the biomarkers are used to identify a subject having poorly differentiated hepatocellular carcinoma who is likely to be responsive to treatment by thalidomide.

In certain embodiments, the biomarkers are used to identify a subject having hepatocellular carcinoma who is likely to be responsive to treatment by lenalidomide. In certain embodiments, the biomarkers are used to identify a subject having poorly differentiated hepatocellular carcinoma who is likely to be responsive to treatment by lenalidomide.

In certain embodiments, the biomarkers are used to identify a subject having hepatocellular carcinoma who is likely to be responsive to treatment by pomalidomide. In certain embodiments, the biomarkers are used to identify a subject having poorly differentiated hepatocellular carcinoma who is likely to be responsive to treatment by pomalidomide.

In certain embodiments, the biomarkers are used to identify a subject having hepatocellular carcinoma who is likely to be responsive to treatment by 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof. In certain embodiments, the biomarkers are used to identify a subject having poorly differentiated hepatocellular carcinoma who is likely to be responsive to treatment by 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

4.3.2 Use of Biomarkers for Predicting the Efficacy

Based, in part, on the finding that detectable increase or decrease in certain biomarkers are observed in subjects with hepatocellular carcinoma who are responsive to a given treatment (e.g., a treatment by a treatment compound, e.g., thalidomide, lenalidomide, pomalidomide, or 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof), the levels of these biomarkers may be used for predicting the responsiveness of the subjects to the treatment.

In one embodiment, provided herein is a method of predicting the responsiveness of a subject having or suspected of having hepatocellular carcinoma to a treatment compound, comprising:
a) determining the level of a biomarker in a hepatocellular carcinoma cell-containing sample from the subject; and
b) comparing the level of the biomarker in the sample to a reference level of the biomarker, wherein an increased level of the biomarker in the sample correlates with an increased responsiveness of the subject to the compound treatment.

In another embodiment, provided herein is a method of predicting the responsiveness of a subject having or suspected of having poorly differentiated hepatocellular carcinoma to a treatment compound, comprising:
a) determining the level of a biomarker in a hepatocellular carcinoma cell-containing sample from the subject; and
b) comparing the level of the biomarker in the sample to a reference level of the biomarker, wherein an increased level of the biomarker in the sample correlates with an increased responsiveness of the subject to the compound treatment.

In yet another embodiment, provided herein is a method of predicting the responsiveness of a subject having or suspected of having hepatocellular carcinoma to a treatment compound, comprising:
a) obtaining a biological sample from the subject;
b) determining the level of a biomarker in the sample; and
c) comparing the level of the biomarker in the sample to a reference level of the biomarker, wherein an increased level of the biomarker in the sample correlates with an increased responsiveness of the subject to the compound treatment.

In yet another embodiment, provided herein is a method of predicting the responsiveness of a subject having or suspected of having poorly differentiated hepatocellular carcinoma to a treatment compound, comprising:
a) obtaining a biological sample from the subject;
b) determining the level of a biomarker in the sample; and
c) comparing the level of the biomarker in the sample to a reference level of the biomarker, wherein an increased level of the biomarker in the sample correlates with an increased responsiveness of the subject to the compound treatment.

In certain embodiments, the reference level is determined from a non-hepatocellular carcinoma cell-containing sample from the same subject. In certain embodiments, the reference level is determined from a non-hepatocellular carcinoma cell-containing sample from a group of subjects.

In certain embodiments, the reference level is determined simultaneously with the hepatocellular carcinoma cell-containing sample. In certain embodiments, the reference level is determined independently from the hepatocellular carcinoma cell-containing sample.

In certain embodiments, an increased level of the biomarker in the hepatocellular carcinoma cell-containing sample as compared to the reference level correlates positively with increased responsiveness of the subject to a treatment compound, e.g., thalidomide, lenalidomide, pomalidomide, or 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

In one embodiment, provided herein is a method of predicting the responsiveness of a subject having or suspected of having hepatocellular carcinoma to a treatment compound, comprising:
a) determining the level of a biomarker in a hepatocellular carcinoma cell-containing sample from the subject;
b) determining the level of the biomarker in a control sample; and
c) comparing the level of the biomarker in the sample from the subject to the level of the biomarker in the control sample, wherein an increased level of the biomarker in the sample correlates with an increased responsiveness of the subject to the compound treatment.

In another embodiment, provided herein is a method of predicting the responsiveness of a subject having or suspected of having poorly differentiated hepatocellular carcinoma to a treatment compound, comprising:
a) determining the level of a biomarker in a hepatocellular carcinoma cell-containing sample from the subject;
b) determining the level of the biomarker in a control sample; and
c) comparing the level of the biomarker in the sample from the subject to the level of the biomarker in the control sample, wherein an increased level of the biomarker in the sample correlates with an increased responsiveness of the subject to the compound treatment.

In yet another embodiment, provided herein is a method of predicting the responsiveness of a subject having or suspected of having hepatocellular carcinoma to a treatment compound, comprising:
a) obtaining a biological sample from the subject;
b) determining the level of a biomarker in the sample;
c) determining the level of the biomarker in a control sample; and
d) comparing the level of the biomarker in the sample from the subject to the level of the biomarker in the control sample, wherein an increased level of the biomarker in the sample correlates with an increased responsiveness of the subject to the compound treatment.

In yet another embodiment, provided herein is a method of predicting the responsiveness of a subject having or suspected of having poorly differentiated hepatocellular carcinoma to a treatment compound, comprising:
a) obtaining a biological sample from the subject;
b) determining the level of a biomarker in the sample;
c) determining the level of the biomarker in a control sample; and
d) comparing the level of the biomarker in the sample from the subject to the level of the biomarker in the control sample, wherein an increased level of the biomarker in the sample correlates with an increased responsiveness of the subject to the compound treatment.

In certain embodiments, the control sample is a non-hepatocellular carcinoma cell-containing sample from the same subject. In certain embodiments, the control sample is a non-hepatocellular carcinoma cell-containing sample from a group of subjects.

In certain embodiments, the level of the biomarker in a control sample is determined simultaneously with the hepatocellular carcinoma cell-containing sample. In certain embodiments, the level of the biomarker in a control sample is determined independently from the hepatocellular carcinoma cell-containing sample.

In certain embodiments, an increased level of the biomarker in the hepatocellular carcinoma cell-containing sample in comparison as compared with the control sample correlates positively with increased responsiveness of the subject to a treatment compound, e.g., thalidomide, lenalidomide, pomalidomide, or 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

In certain embodiments, the biomarker is TCF, WISP2, ASPH, IRS1, MAPK12, CLDN2, JAG1, GPR56, ANXA1, CAMK2N1, STK17B, SPP1, AXIN2, MMP1, CADM1, PLCD4, CD24, or a combination thereof. In certain embodiments, the biomarker is hTCF, WISP2, ASPH, IRS1, MAPK12, CLDN2, JAG1, GPR56, ANXA1, CAMK2N1, STK17B, SPP1, AXIN2, MMP7, CADM1, PLCD4, CD24, or a combination thereof. In certain embodiments, the biomarker is TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, or a combination thereof. In certain embodiments, the biomarker is hTCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, or a combination thereof.

In certain embodiments, the biomarker is TCF, CLDN2, ASPH, JAG1, GPR56, ANXA1, CAMK2N1, or a combination thereof. In certain embodiments, the biomarker is hTCF, CLDN2, ASPH, JAG1, GPR56, ANXA1, CAMK2N1, or a combination thereof. In certain embodiments, the biomarker is TCF-4, CLDN2, ASPH, JAG1, GPR56, ANXA1, CAMK2N1, or a combination thereof. In certain embodiments, the biomarker is hTCF-4, CLDN2, ASPH, JAG1, GPR56, ANXA1, CAMK2N1, or a combination thereof.

In certain embodiments, the biomarker is TCF, WISP2, ASPH, IRS1, MAPK12, JAG1, or a combination thereof. In certain embodiments, the biomarker is hTCF, WISP2, ASPH, IRS1, MAPK12, JAG1, or a combination thereof. In certain embodiments, the biomarker is TCF-4, WISP2, ASPH, IRS1, MAPK12, JAG1, or a combination thereof. In certain embodiments, the biomarker is hTCF-4, WISP2, ASPH, IRS1, MAPK12, JAG1, or a combination thereof.

In certain embodiments, the biomarker is TCF-4-A, TCF-4B, TCF-4C, TCF-4D, TCF-4E, TCF-4F, TCF-4G, TCF-4H, TCF-4I, TCF-4J, TCF-4K, TCF-4L, TCF-4M, TCF-4X, WISP2, ASPH, IRS1, MAPK12, CLDN2, JAG1, GPR56, ANXA1, CAMK2N1, STK17B, SPP1, AXIN2, MMP7, CADM1, PLCD4, CD24, or a combination thereof. In certain embodiments, the biomarker is hTCF-4-A, hTCF-4B, hTCF-4C, hTCF-4D, hTCF-4E, hTCF-4F, hTCF-4G, hTCF-4H, hTCF-4I, hTCF-4J, hTCF-4K, hTCF-4L, hTCF-4M, hTCF-4X, WISP2, ASPH, IRS1, MAPK12, CLDN2, JAG1, GPR56, ANXA1, CAMK2N1, STK17B, SPP1, AXIN2, MMP7, CADM1, PLCD4, CD24, or a combination thereof. In certain embodiments, the biomarker is TCF-4C, TCF-4J, TCF-4L, WISP2, ASPH, IRS1, MAPK12, CLDN2, JAG1, GPR56, ANXA1, CAMK2N1, STK17B, SPP1, AXIN2, MMP7, CADM1, PLCD4, CD24, or a combination thereof. In certain embodiments, the biomarker is hTCF-4C, hTCF-4J, hTCF-4L, WISP2, ASPH, IRS1, MAPK12, CLDN2, JAG1, GPR56, ANXA1, CAMK2N1, STK17B, SPP1, AXIN2, MMP1, CADM1, PLCD4, CD24, or a combination thereof. In certain embodiments, the biomarker is TCF-4C, TCF-4J, TCF-4L, or a combination thereof. In certain embodiments, the biomarker is hTCF-4C, hTCF-4J, hTCF-4L, or a combination thereof. In certain embodiments, the biomarker is a combination of TCF-4C, TCF-4J, and TCF-4L. In certain embodiments, the biomarker is a combination of hTCF-4C, hTCF-4J, hTCF-4L.

In certain embodiments, the biomarkers are used to predict the responsiveness of a subject having or suspected of having hepatocellular carcinoma to a treatment by thalidomide, lenalidomide, pomalidomide, or 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

In certain embodiments, the biomarkers are used to predict the responsiveness of a subject having or suspected of having poorly differentiated hepatocellular carcinoma to a treatment by thalidomide, lenalidomide, pomalidomide, or 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

In certain embodiments, the biomarkers are used to predict the responsiveness of a subject having or suspected of having hepatocellular carcinoma to a treatment by thalidomide. In certain embodiments, the biomarkers are used to predict the responsiveness of a subject having or suspected of having poorly differentiated hepatocellular carcinoma to a treatment by thalidomide.

In certain embodiments, the biomarkers are used to predict the responsiveness of a subject having or suspected of having hepatocellular carcinoma to a treatment by lenalidomide. In certain embodiments, the biomarkers are used to predict the responsiveness of a subject having or suspected of having poorly differentiated hepatocellular carcinoma to a treatment by lenalidomide.

In certain embodiments, the biomarkers are used to predict the responsiveness of a subject having or suspected of having hepatocellular carcinoma to a treatment by pomalidomide. In certain embodiments, the biomarkers are used to predict the responsiveness of a subject having or suspected of having poorly differentiated hepatocellular carcinoma to a treatment by pomalidomide.

In certain embodiments, the biomarkers are used to predict the responsiveness of a subject having or suspected of having hepatocellular carcinoma to a treatment by 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof. In certain embodiments, the biomarkers are used to predict the responsiveness of a subject having or suspected of having poorly differentiated hepatocellular carcinoma to a treatment by 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

In certain embodiments, the level of the biomarker is measured in an in vitro assay to predict the responsiveness of a subject to a treatment of hepatocellular carcinoma (e.g., a treatment by a treatment compound provided herein), comprising obtaining a sample of cells from the subject, culturing the cells in the presence or absence of a treatment compound, and testing the cells for the levels of the biomarkers, wherein a decreased level of the biomarker in the presence of the treatment compound indicates the likelihood of responsiveness of the subject to the treatment compound.

4.3.3 Use of mRNAs as biomarkers for identifying a subject for Treatment

Based, in part, on the finding that detectable increase or decrease in certain mRNAs are observed in subjects with hepatocellular carcinoma who are responsive to a given treatment (e.g., a treatment by a treatment compound, e.g., thalidomide, lenalidomide, pomalidomide, or 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof), the levels of the mRNA biomarkers may be used for identifying a subject having hepatocellular carcinoma (e.g., poorly differentiated HCC) for the treatment by a treatment compound provided herein.

In one embodiment, provided herein is a method of identifying a subject having hepatocellular carcinoma who is likely to be responsive to a treatment compound, comprising:

a) determining the level of an mRNA biomarker in a hepatocellular carcinoma cell-containing sample from the subject; and b) comparing the level of the mRNA biomarker in the sample to a reference level of the mRNA biomarker; wherein the subject is likely to be responsive to the treatment if the level of the mRNA biomarker in the sample of the subject is higher than the reference level of the mRNA biomarker.

In another embodiment, provided herein is a method of identifying a subject having poorly differentiated hepatocellular carcinoma who is likely to be responsive to a treatment compound, comprising:

a) determining the level of an mRNA biomarker in a hepatocellular carcinoma cell-containing sample from the subject; and b) comparing the level of the mRNA biomarker in the sample to a reference level of the mRNA biomarker; wherein the subject is likely to be responsive to the treatment if the level of the mRNA biomarker in the sample of the subject is higher than the reference level of the mRNA biomarker.

In yet another embodiment, provided herein is a method of identifying a subject having hepatocellular carcinoma who is likely to be responsive to a treatment compound, comprising:

a) obtaining a biological sample from the subject;

b) determining the level of an mRNA biomarker in the sample; and c) comparing the level of the mRNA biomarker in the sample to a reference level of the mRNA biomarker; wherein the subject is likely to be responsive to the treatment if the level of the mRNA biomarker in the sample of the subject is higher than the reference level of the mRNA biomarker.

In yet another embodiment, provided herein is a method of identifying a subject having poorly differentiated hepatocellular carcinoma who is likely to be responsive to a treatment compound, comprising:

a) obtaining a biological sample from the subject;

b) determining the level of an mRNA biomarker in the sample; and c) comparing the level of the mRNA biomarker in the sample to a reference level of the mRNA biomarker; wherein the subject is likely to be responsive to the treatment if the level of the mRNA biomarker in the sample of the subject is higher than the reference level of the mRNA biomarker.

In certain embodiments, the reference level is determined from a non-hepatocellular carcinoma cell-containing sample from the same subject. In certain embodiments, the reference level is determined from a non-hepatocellular carcinoma cell-containing sample from a group of subjects.

In certain embodiments, the reference level is determined simultaneously with the hepatocellular carcinoma cell-containing sample. In certain embodiments, the reference level is determined independently from the hepatocellular carcinoma cell-containing sample.

In one embodiment, provided herein is a method of identifying a subject having hepatocellular carcinoma who is likely to be responsive to a treatment compound, comprising:

a) determining the level of an mRNA biomarker in a hepatocellular carcinoma cell-containing sample from the subject; and b) determining the level of the mRNA biomarker in a control sample; wherein the subject is likely to be responsive to the treatment if the level of the mRNA biomarker in the sample of the subject is higher than the level of the mRNA biomarker in the control sample.

In another embodiment, provided herein is a method of identifying a subject having poorly differentiated hepatocellular carcinoma who is likely to be responsive to a treatment compound, comprising:

a) determining the level of an mRNA biomarker in a hepatocellular carcinoma cell-containing sample from the subject; and b) determining the level of the mRNA biomarker in a control sample; wherein the subject is likely to be responsive to the treatment if the level of the mRNA biomarker in the sample of the subject is higher than the level of the mRNA biomarker in the control sample In yet another embodiment, provided herein is a method of identifying a subject having hepatocellular carcinoma who is likely to be responsive to a treatment compound, comprising:

a) obtaining a biological sample from the subject;

b) determining the level of an mRNA biomarker in the sample; and c) determining the level of the mRNA biomarker in a control sample; wherein the subject is likely to be responsive to the treatment if the level of the mRNA biomarker in the sample of the subject is higher than the level of the mRNA biomarker in the control sample.

In yet another embodiment, provided herein is a method of identifying a subject having poorly differentiated hepatocellular carcinoma who is likely to be responsive to a treatment compound, comprising:

a) obtaining a biological sample from the subject;

b) determining the level of an mRNA biomarker in the sample; and c) determining the level of the mRNA biomarker in a control sample; wherein the subject is likely to be responsive to the treatment if the level of the mRNA biomarker in the sample of the subject is higher than the level of the mRNA biomarker in the control sample.

In certain embodiments, the control sample is a non-hepatocellular carcinoma cell-containing sample from the same subject. In certain embodiments, the control sample is a non-hepatocellular carcinoma cell-containing sample from a group of subjects.

Thus, in one embodiment, provided herein is a method of identifying a subject having hepatocellular carcinoma who is likely to be responsive to a treatment compound, comprising:

a) determining the level of an mRNA biomarker in a hepatocellular carcinoma cell-containing sample from the subject; and b) determining the level of the mRNA biomarker in a control sample from the subject; wherein the subject is likely to be responsive to the treatment if the level of the mRNA biomarker in the sample of the subject is higher than the level of the mRNA biomarker in the control sample.

In another embodiment, provided herein is a method of identifying a subject having poorly differentiated hepatocellular carcinoma who is likely to be responsive to a treatment compound, comprising:
- a) determining the level of an mRNA biomarker in a hepatocellular carcinoma cell-containing sample from the subject; and
- b) determining the level of the mRNA biomarker in a control sample from the subject; wherein the subject is likely to be responsive to the treatment if the level of the mRNA biomarker in the sample of the subject is higher than the level of the mRNA biomarker in the control sample In yet another embodiment, provided herein is a method of identifying a subject having hepatocellular carcinoma who is likely to be responsive to a treatment compound, comprising:
- a) obtaining a biological sample from the subject;
- b) determining the level of an mRNA biomarker in the sample; and
- c) determining the level of the mRNA biomarker in a control sample from the subject; wherein the subject is likely to be responsive to the treatment if the level of the mRNA biomarker in the sample of the subject is higher than the level of the mRNA biomarker in the control sample.

In yet another embodiment, provided herein is a method of identifying a subject having poorly differentiated hepatocellular carcinoma who is likely to be responsive to a treatment compound, comprising:
- a) obtaining a biological sample from the subject;
- b) determining the level of an mRNA biomarker in the sample; and
- c) determining the level of the mRNA biomarker in a control sample from the subject; wherein the subject is likely to be responsive to the treatment if the level of the mRNA biomarker in the sample of the subject is higher than the level of the mRNA biomarker in the control sample.

In certain embodiments, the level of the mRNA biomarker in a control sample is determined simultaneously with the hepatocellular carcinoma cell-containing sample. In certain embodiments, the level of the mRNA biomarker in a control sample is determined independently from the hepatocellular carcinoma cell-containing sample.

In certain embodiments, the methods provided herein are coupled with a treatment by a treatment compound provided herein, e.g., thalidomide, lenalidomide, pomalidomide, or 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

Thus, in one embodiment, provided herein is a method of treating hepatocellular carcinoma, comprising:
- (i) identifying a subject having hepatocellular carcinoma who is likely to be responsive to a treatment compound, comprising:
    - a) determining the level of an mRNA biomarker in a hepatocellular carcinoma cell-containing sample from the subject; and
    - b) comparing the level of the mRNA biomarker in the sample to a reference level of the mRNA biomarker; wherein the subject is likely to be responsive to the treatment if the level of the mRNA biomarker in the sample of the subject is higher than the reference level of the mRNA biomarker; and
- (ii) administering a therapeutically effective amount of the compound to the subject identified to be likely to be responsive to the treatment.

In another embodiment, provided herein is a method of treating poorly differentiated hepatocellular carcinoma, comprising:
- (i) identifying a subject having hepatocellular carcinoma who is likely to be responsive to a treatment compound, comprising:
    - a) determining the level of an mRNA biomarker in a hepatocellular carcinoma cell-containing sample from the subject; and
    - b) comparing the level of the mRNA biomarker in the sample to a reference level of the mRNA biomarker; wherein the subject is likely to be responsive to the treatment if the level of the mRNA biomarker in the sample of the subject is higher than the reference level of the mRNA biomarker; and
- (ii) administering a therapeutically effective amount of the compound to the subject identified to be likely to be responsive to the treatment.

In yet another embodiment, provided herein is a method of treating hepatocellular carcinoma, comprising:
- (i) identifying a subject having hepatocellular carcinoma who is likely to be responsive to a treatment compound, comprising:
    - a) obtaining a biological sample from the subject;
    - b) determining the level of an mRNA biomarker in the sample; and
    - c) comparing the level of the mRNA biomarker in the sample to a reference level of the mRNA biomarker; wherein the subject is likely to be responsive to the treatment if the level of the mRNA biomarker in the sample of the subject is higher than the reference level of the mRNA biomarker; and
- (ii) administering a therapeutically effective amount of the compound to the subject identified to be likely to be responsive to the treatment.

In yet another embodiment, provided herein is a method of treating poorly differentiated hepatocellular carcinoma, comprising:
- (i) identifying a subject having hepatocellular carcinoma who is likely to be responsive to a treatment compound, comprising:
    - a) obtaining a biological sample from the subject;
    - b) determining the level of an mRNA biomarker in the sample; and
    - c) comparing the level of the mRNA biomarker in the sample to a reference level of the mRNA biomarker; wherein the subject is likely to be responsive to the treatment if the level of the mRNA biomarker in the sample of the subject is higher than the reference level of the mRNA biomarker; and
- (ii) administering a therapeutically effective amount of the compound to the subject identified to be likely to be responsive to the treatment.

In yet another embodiment, provided herein is a method of treating hepatocellular carcinoma, comprising:
- (i) identifying a subject having hepatocellular carcinoma who is likely to be responsive to a treatment compound, comprising:
    - a) determining the level of an mRNA biomarker in a hepatocellular carcinoma cell-containing sample from the subject; and
    - b) determining the level of the mRNA biomarker in a control sample; wherein the subject is likely to be responsive to the treatment if the level of the mRNA biomarker in the sample of the subject is higher than the level of the mRNA biomarker in the control sample; and (ii) administering a therapeutically effective amount of the compound to the subject identified to be likely to be responsive to the treatment.

In yet another embodiment, provided herein is a method of treating poorly differentiated hepatocellular carcinoma, comprising:
(i) identifying a subject having hepatocellular carcinoma who is likely to be responsive to a treatment compound, comprising:
a) determining the level of an mRNA biomarker in a hepatocellular carcinoma cell-containing sample from the subject; and
b) determining the level of the mRNA biomarker in a control sample; wherein the subject is likely to be responsive to the treatment if the level of the mRNA biomarker in the sample of the subject is higher than the level of the mRNA biomarker in the control sample; and
(ii) administering a therapeutically effective amount of the compound to the subject identified to be likely to be responsive to the treatment.

In yet another embodiment, provided herein is a method of treating hepatocellular carcinoma, comprising:
(i) identifying a subject having hepatocellular carcinoma who is likely to be responsive to a treatment compound, comprising:
a) obtaining a biological sample from the subject;
b) determining the level of an mRNA biomarker in the sample; and
c) determining the level of the mRNA biomarker in a control sample; wherein the subject is likely to be responsive to the treatment if the level of the mRNA biomarker in the sample of the subject is higher than the level of the mRNA biomarker in the control sample; and
(ii) administering a therapeutically effective amount of the compound to the subject identified to be likely to be responsive to the treatment.

In yet another embodiment, provided herein is a method of treating poorly differentiated hepatocellular carcinoma, comprising:
(i) identifying a subject having hepatocellular carcinoma who is likely to be responsive to a treatment compound, comprising:
a) obtaining a biological sample from the subject;
b) determining the level of an mRNA biomarker in the sample; and
c) determining the level of the mRNA biomarker in a control sample; wherein the subject is likely to be responsive to the treatment if the level of the mRNA biomarker in the sample of the subject is higher than the level of the mRNA biomarker in the control sample; and
(ii) administering a therapeutically effective amount of the compound to the subject identified to be likely to be responsive to the treatment.

In certain embodiments, the biomarker is an mRNA of TCF, WISP2, ASPH, IRS1, MAPK12, CLDN2, JAG1, GPR56, ANXA1, CAMK2N1, STK17B, SPP1, AXIN2, MMP7, CADM1, PLCD4, CD24, or a combination thereof. In certain embodiments, the biomarker is an mRNA of hTCF, WISP2, ASPH, IRS1, MAPK12, CLDN2, JAG1, GPR56, ANXA1, CAMK2N1, STK17B, SPP1, AXIN2, MMP7, CADM1, PLCD4, CD24, or a combination thereof. In certain embodiments, the biomarker is an mRNA of TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, or a combination thereof. In certain embodiments, the biomarker is an mRNA of hTCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, or a combination thereof.

In certain embodiments, the biomarker is an mRNA of TCF, CLDN2, ASPH, JAG1, GPR56, ANXA1, CAMK2N1, or a combination thereof. In certain embodiments, the biomarker is an mRNA of hTCF, CLDN2, ASPH, JAG1, GPR56, ANXA1, CAMK2N1, or a combination thereof. In certain embodiments, the biomarker is an mRNA of TCF-4, CLDN2, ASPH, JAG1, GPR56, ANXA1, CAMK2N1, or a combination thereof. In certain embodiments, the biomarker is an mRNA of hTCF-4, CLDN2, ASPH, JAG1, GPR56, ANXA1, CAMK2N1, or a combination thereof.

In certain embodiments, the biomarker is an mRNA of TCF, WISP2, ASPH, IRS1, MAPK12, JAG1, or a combination thereof. In certain embodiments, the biomarker is an mRNA of hTCF, WISP2, ASPH, IRS1, MAPK12, JAG1, or a combination thereof. In certain embodiments, the biomarker is an mRNA of TCF-4, WISP2, ASPH, IRS1, MAPK12, JAG1, or a combination thereof. In certain embodiments, the biomarker is hTCF-4, WISP2, ASPH, IRS1, MAPK12, JAG1, or a combination thereof.

In certain embodiments, the biomarker is an mRNA of TCF-4-A, TCF-4B, TCF-4C, TCF-4D, TCF-4E, TCF-4F, TCF-4G, TCF-4H, TCF-4I, TCF-4J, TCF-4K, TCF-4L, TCF-4M, TCF-4X, WISP2, ASPH, IRS1, MAPK12, CLDN2, JAG1, GPR56, ANXA1, CAMK2N1, STK17B, SPP1, AXIN2, MMP7, CADM1, PLCD4, CD24, or a combination thereof. In certain embodiments, the biomarker is hTCF-4-A, hTCF-4B, hTCF-4C, hTCF-4D, hTCF-4E, hTCF-4F, hTCF-4G, hTCF-4H, hTCF-4I, hTCF-4J, hTCF-4K, hTCF-4L, hTCF-4M, hTCF-4X, WISP2, ASPH, IRS1, MAPK12, CLDN2, JAG1, GPR56, ANXA1, CAMK2N1, STK17B, SPP1, AXIN2, MMP7, CADM1, PLCD4, CD24, or a combination thereof. In certain embodiments, the biomarker is an mRNA of TCF-4C, TCF-4J, TCF-4L, WISP2, ASPH, IRS1, MAPK12, CLDN2, JAG1, GPR56, ANXA1, CAMK2N1, STK17B, SPP1, AXIN2, MMP7, CADM1, PLCD4, CD24, or a combination thereof. In certain embodiments, the biomarker is an mRNA of hTCF-4C, hTCF-4J, hTCF-4L, WISP2, ASPH, IRS1, MAPK12, CLDN2, JAG1, GPR56, ANXA1, CAMK2N1, STK17B, SPP1, AXIN2, MMP7, CADM1, PLCD4, CD24, or a combination thereof. In certain embodiments, the biomarker is an mRNA of TCF-4C, TCF-4J, TCF-4L, or a combination thereof. In certain embodiments, the biomarker is an mRNA of hTCF-4C, hTCF-4J, hTCF-4L, or a combination thereof. In certain embodiments, the biomarker is a combination of an mRNA of TCF-4C, TCF-4J, and TCF-4L. In certain embodiments, the biomarker is a combination of an mRNA of hTCF-4C, hTCF-4J, hTCF-4L.

In certain embodiments, the mRNA biomarkers are used to identify a subject having hepatocellular carcinoma who is likely to be responsive to treatment by thalidomide, lenalidomide, pomalidomide, or 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

In certain embodiments, the mRNA biomarkers are used to identify a subject having poorly differentiated hepatocellular carcinoma who is likely to be responsive to treatment by thalidomide, lenalidomide, pomalidomide, or 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

In certain embodiments, the mRNA biomarkers are used to identify a subject having hepatocellular carcinoma who is likely to be responsive to treatment by thalidomide. In certain embodiments, the mRNA biomarkers are used to identify a subject having poorly differentiated hepatocellular carcinoma who is likely to be responsive to treatment by thalidomide.

In certain embodiments, the mRNA biomarkers are used to identify a subject having hepatocellular carcinoma who is likely to be responsive to treatment by lenalidomide. In certain embodiments, the mRNA biomarkers are used to identify a subject having poorly differentiated hepatocellular carcinoma who is likely to be responsive to treatment by lenalidomide.

In certain embodiments, the mRNA biomarkers are used to identify a subject having hepatocellular carcinoma who is likely to be responsive to treatment by pomalidomide. In certain embodiments, the mRNA biomarkers are used to identify a subject having poorly differentiated hepatocellular carcinoma who is likely to be responsive to treatment by pomalidomide.

In certain embodiments, the mRNA biomarkers are used to identify a subject having hepatocellular carcinoma who is likely to be responsive to treatment by 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof. In certain embodiments, the mRNA biomarkers are used to identify a subject having poorly differentiated hepatocellular carcinoma who is likely to be responsive to treatment by 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

In certain embodiments, the level of the mRNA biomarker is measured in a biological sample obtained from the subject.

In certain embodiments, the level of the mRNA biomarker is measured in an in vitro assay to predict the responsiveness of a subject to a treatment of hepatocellular carcinoma, comprising obtaining a sample of cells from the subject, culturing the cells in the presence or absence of a treatment compound, and testing the cells for the levels of the biomarkers, wherein a decreased level of the biomarker in the presence of the treatment compound indicates the likelihood of responsiveness of the subject to the treatment compound.

In certain embodiments, the level of only one of the mRNA biomarkers is monitored. In certain embodiments, the levels of two or more of the mRNA biomarkers are monitored simultaneously.

4.3.4 Use of mRNA as Biomarkers for Predicting the Efficacy

Based, in part, on the finding that detectable increase or decrease in certain mRNA biomarkers are observed in subjects with hepatocellular carcinoma who are responsive to a given treatment (e.g., a treatment by a treatment compound provided herein, e.g., thalidomide, lenalidomide, pomalidomide, or 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof), the levels of these mRNA biomarkers may be used for predicting the responsiveness of the subjects to the treatment.

In one embodiment, provided herein is a method of predicting the responsiveness of a subject having or suspected of having hepatocellular carcinoma to a treatment compound, comprising:

a) determining the level of an mRNA biomarker in a hepatocellular carcinoma cell-containing sample from the subject; and b) comparing the level of the mRNA biomarker in the sample to a reference level of the mRNA biomarker, wherein an increased level of the mRNA biomarker in the sample correlates with an increased responsiveness of the subject to the compound treatment.

In another embodiment, provided herein is a method of predicting the responsiveness of a subject having or suspected of having poorly differentiated hepatocellular carcinoma to a treatment compound, comprising:

a) determining the level of an mRNA biomarker in a hepatocellular carcinoma cell-containing sample from the subject; and b) comparing the level of the mRNA biomarker in the sample to a reference level of the mRNA biomarker, wherein an increased level of the mRNA biomarker in the sample correlates with an increased responsiveness of the subject to the compound treatment.

In yet another embodiment, provided herein is a method of predicting the responsiveness of a subject having or suspected of having hepatocellular carcinoma to a treatment compound, comprising:

a) obtaining a biological sample from the subject;

b) determining the level of an mRNA biomarker in the sample; and c) comparing the level of the mRNA biomarker in the sample to a reference level of the mRNA biomarker, wherein an increased level of the mRNA biomarker in the sample correlates with an increased responsiveness of the subject to the compound treatment.

In yet another embodiment, provided herein is a method of predicting the responsiveness of a subject having or suspected of having poorly differentiated hepatocellular carcinoma to a treatment compound, comprising:

a) obtaining a biological sample from the subject;

b) determining the level of an mRNA biomarker in the sample; and c) comparing the level of the mRNA biomarker in the sample to a reference level of the mRNA biomarker, wherein an increased level of the mRNA biomarker in the sample correlates with an increased responsiveness of the subject to the compound treatment.

In certain embodiments, the reference level is determined from a non-hepatocellular carcinoma cell-containing sample from the same subject. In certain embodiments, the reference level is determined from a non-hepatocellular carcinoma cell-containing sample from a group of subjects.

In certain embodiments, the reference level is determined simultaneously with the hepatocellular carcinoma cell-containing sample. In certain embodiments, the reference level is determined independently from the hepatocellular carcinoma cell-containing sample.

In certain embodiments, an increased level of the mRNA biomarker in the hepatocellular carcinoma cell-containing sample as compared to the reference level correlates positively with increased responsiveness of the subject to a treatment compound provided herein, e.g., thalidomide, lenalidomide, pomalidomide, or 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

In one embodiment, provided herein is a method of predicting the responsiveness of a subject having or suspected of having hepatocellular carcinoma to a treatment compound, comprising:

a) determining the level of an mRNA biomarker in a hepatocellular carcinoma cell-containing sample from the subject;

b) determining the level of the mRNA biomarker in a control sample; and c) comparing the level of the mRNA biomarker in the sample from the subject to the level of the mRNA biomarker in the control sample, wherein an increased level of the mRNA biomarker in the sample correlates with an increased responsiveness of the subject to the compound treatment.

In another embodiment, provided herein is a method of predicting the responsiveness of a subject having or suspected of having poorly differentiated hepatocellular carcinoma to a treatment compound, comprising:

a) determining the level of an mRNA biomarker in a hepatocellular carcinoma cell-containing sample from the subject;

b) determining the level of the mRNA biomarker in a control sample; and c) comparing the level of the mRNA biomarker in the sample from the subject to the level of the mRNA biomarker in the control sample, wherein an increased level of the mRNA biomarker in the sample correlates with an increased responsiveness of the subject to the compound treatment.

In yet another embodiment, provided herein is a method of predicting the responsiveness of a subject having or suspected of having hepatocellular carcinoma to a treatment compound, comprising:

a) obtaining a biological sample from the subject;

b) determining the level of an mRNA biomarker in the sample;

c) determining the level of the mRNA biomarker in a control sample; and d) comparing the level of the mRNA biomarker in the sample from the subject to the level of the mRNA biomarker in the control sample, wherein an increased level of the mRNA biomarker in the sample correlates with an increased responsiveness of the subject to the compound treatment.

In yet another embodiment, provided herein is a method of predicting the responsiveness of a subject having or suspected of having poorly differentiated hepatocellular carcinoma to a treatment compound, comprising:

a) obtaining a biological sample from the subject;

b) determining the level of an mRNA biomarker in the sample;

c) determining the level of the mRNA biomarker in a control sample; and d) comparing the level of the mRNA biomarker in the sample from the subject to the level of the mRNA biomarker in the control sample, wherein an increased level of the mRNA biomarker in the sample correlates with an increased responsiveness of the subject to the compound treatment.

In certain embodiments, the control sample is a non-hepatocellular carcinoma cell-containing sample from the same subject. In certain embodiments, the control sample is a non-hepatocellular carcinoma cell-containing sample from a group of subjects.

In certain embodiments, the level of the mRNA biomarker in a control sample is determined simultaneously with the hepatocellular carcinoma cell-containing sample. In certain embodiments, the level of the mRNA biomarker in a control sample is determined independently from the hepatocellular carcinoma cell-containing sample.

In certain embodiments, an increased level of the mRNA biomarker in the hepatocellular carcinoma cell-containing sample in comparison as compared with the control sample correlates positively with increased responsiveness of the subject to a treatment compound provided herein, e.g., thalidomide, lenalidomide, pomalidomide, or 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

In certain embodiments, the biomarker is an mRNA of TCF, WISP2, ASPH, IRS1, MAPK12, CLDN2, JAG1, GPR56, ANXA1, CAMK2N1, STK17B, SPP1, AXIN2, MMP7, CADM1, PLCD4, CD24, or a combination thereof. In certain embodiments, the biomarker is an mRNA of hTCF, WISP2, ASPH, IRS1, MAPK12, CLDN2, JAG1, GPR56, ANXA1, CAMK2N1, STK17B, SPP1, AXIN2, MMP7, CADM1, PLCD4, CD24, or a combination thereof. In certain embodiments, the biomarker is an mRNA of TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, or a combination thereof. In certain embodiments, the biomarker is an mRNA of hTCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, or a combination thereof.

In certain embodiments, the biomarker is an mRNA of TCF, CLDN2, ASPH, JAG1, GPR56, ANXA1, CAMK2N1, or a combination thereof. In certain embodiments, the biomarker is an mRNA of hTCF, CLDN2, ASPH, JAG1, GPR56, ANXA1, CAMK2N1, or a combination thereof. In certain embodiments, the biomarker is an mRNA of TCF-4, CLDN2, ASPH, JAG1, GPR56, ANXA1, CAMK2N1, or a combination thereof. In certain embodiments, the biomarker is an mRNA of hTCF-4, CLDN2, ASPH, JAG1, GPR56, ANXA1, CAMK2N1, or a combination thereof.

In certain embodiments, the biomarker is an mRNA of TCF, WISP2, ASPH, IRS1, MAPK12, JAG1, or a combination thereof. In certain embodiments, the biomarker is an mRNA of hTCF, WISP2, ASPH, IRS1, MAPK12, JAG1, or a combination thereof. In certain embodiments, the biomarker is an mRNA of TCF-4, WISP2, ASPH, IRS1, MAPK12, JAG1, or a combination thereof. In certain embodiments, the biomarker is an mRNA of hTCF-4, WISP2, ASPH, IRS1, MAPK12, JAG1, or a combination thereof.

In certain embodiments, the biomarker is an mRNA of TCF-4-A, TCF-4B, TCF-4C, TCF-4D, TCF-4E, TCF-4F, TCF-4G, TCF-4H, TCF-4I, TCF-4J, TCF-4K, TCF-4L, TCF-4M, TCF-4X, WISP2, ASPH, IRS1, MAPK12, CLDN2, JAG1, GPR56, ANXA1, CAMK2N1, STK17B, SPP1, AXIN2, MMP7, CADM1, PLCD4, CD24, or a combination thereof. In certain embodiments, the biomarker is an mRNA of hTCF-4-A, hTCF-4B, hTCF-4C, hTCF-4D, hTCF-4E, hTCF-4F, hTCF-4G, hTCF-4H, hTCF-4I, hTCF-4J, hTCF-4K, hTCF-4L, hTCF-4M, hTCF-4X, WISP2, ASPH, IRS1, MAPK12, CLDN2, JAG1, GPR56, ANXA1, CAMK2N1, STK17B, SPP1, AXIN2, MMP7, CADM1, PLCD4, CD24, or a combination thereof. In certain embodiments, the biomarker is an mRNA of TCF-4C, TCF-4J, TCF-4L, WISP2, ASPH, IRS1, MAPK12, CLDN2, JAG1, GPR56, ANXA1, CAMK2N1, STK17B, SPP1, AXIN2, MMP7, CADM1, PLCD4, CD24, or a combination thereof. In certain embodiments, the biomarker is an mRNA of hTCF-4C, hTCF-4J, hTCF-4L, WISP2, ASPH, IRS1, MAPK12, CLDN2, JAG1, GPR56, ANXA1, CAMK2N1, STK17B, SPP1, AXIN2, MMP7, CADM1, PLCD4, CD24, or a combination thereof. In certain embodiments, the biomarker is an mRNA of TCF-4C, TCF-4J, TCF-4L, or a combination thereof. In certain embodiments, the biomarker is hTCF-4C, hTCF-4J, hTCF-4L, or a combination thereof. In certain embodiments, the biomarker is a combination of an mRNA of TCF-4C, TCF-4J, and TCF-4L. In certain embodiments, the biomarker is a combination of an mRNA of hTCF-4C, hTCF-4J, hTCF-4L.

In certain embodiments, the mRNA biomarkers are used to predict the responsiveness of a subject having or suspected of having hepatocellular carcinoma to a treatment by thalidomide, lenalidomide, pomalidomide, or 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

In certain embodiments, the mRNA biomarkers are used to predict the responsiveness of a subject having or suspected of having poorly differentiated hepatocellular carcinoma to a treatment by thalidomide, lenalidomide, pomalidomide, or 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

In certain embodiments, the mRNA biomarkers are used to predict the responsiveness of a subject having or suspected of having hepatocellular carcinoma to a treatment by thalidomide. In certain embodiments, the mRNA biomarkers are used to predict the responsiveness of a subject having or suspected of having poorly differentiated hepatocellular carcinoma to a treatment by thalidomide.

In certain embodiments, the mRNA biomarkers are used to predict the responsiveness of a subject having or suspected of having hepatocellular carcinoma to a treatment by lenalidomide. In certain embodiments, the mRNA biomarkers are used to predict the responsiveness of a subject having or suspected of having poorly differentiated hepatocellular carcinoma to a treatment by lenalidomide.

In certain embodiments, the mRNA biomarkers are used to predict the responsiveness of a subject having or suspected of having hepatocellular carcinoma to a treatment by pomalidomide. In certain embodiments, the mRNA biomarkers are used to predict the responsiveness of a subject having or suspected of having poorly differentiated hepatocellular carcinoma to a treatment by pomalidomide.

In certain embodiments, the mRNA biomarkers are used to predict the responsiveness of a subject having or suspected of having hepatocellular carcinoma to a treatment by 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof. In certain embodiments, the mRNA biomarkers are used to predict the responsiveness of a subject having or suspected of having poorly differentiated hepatocellular carcinoma to a treatment by 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

In certain embodiments, the level of the mRNA biomarker is measured in an in vitro assay to predict the responsiveness of a subject to a treatment of hepatocellular carcinoma by a treatment compound, comprising obtaining a sample of cells from the subject, culturing the cells in the presence or absence of a treatment compound, and testing the cells for the levels of the mRNA biomarkers, wherein a decreased level of the mRNA biomarker in the presence of the treatment compound indicates the likelihood of responsiveness of the subject to the treatment compound.

In certain embodiments, the mRNA biomarkers are used to predict the responsiveness of a subject having or suspected of having hepatocellular carcinoma to a treatment by thalidomide, lenalidomide, pomalidomide, or 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

In certain embodiments, the mRNA biomarkers are used to predict the responsiveness of a subject having or suspected of having poorly differentiated hepatocellular carcinoma to a treatment by thalidomide, lenalidomide, pomalidomide, or 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

In certain embodiments, the mRNA biomarkers are used to predict the responsiveness of a subject having or suspected of having hepatocellular carcinoma to a treatment by thalidomide. In certain embodiments, the mRNA biomarkers are used to predict the responsiveness of a subject having or suspected of having poorly differentiated hepatocellular carcinoma to a treatment by thalidomide.

In certain embodiments, the mRNA biomarkers are used to predict the responsiveness of a subject having or suspected of having hepatocellular carcinoma to a treatment by lenalidomide. In certain embodiments, the mRNA biomarkers are used to predict the responsiveness of a subject having or suspected of having poorly differentiated hepatocellular carcinoma to a treatment by lenalidomide.

In certain embodiments, the mRNA biomarkers are used to predict the responsiveness of a subject having or suspected of having hepatocellular carcinoma to a treatment by pomalidomide. In certain embodiments, the mRNA biomarkers are used to predict the responsiveness of a subject having or suspected of having poorly differentiated hepatocellular carcinoma to a treatment by pomalidomide.

In certain embodiments, the mRNA biomarkers are used to predict the responsiveness of a subject having or suspected of having hepatocellular carcinoma to a treatment by 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof. In certain embodiments, the mRNA biomarkers are used to predict the responsiveness of a subject having or suspected of having poorly differentiated hepatocellular carcinoma to a treatment by 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

In certain embodiments, the level of the mRNA biomarker is measured in a biological sample obtained from the subject.

In certain embodiments, the level of the mRNA biomarker is measured in an in vitro assay to predict the responsiveness of a subject to a treatment of hepatocellular carcinoma, comprising obtaining a sample of cells from the subject, culturing the cells in the presence or absence of a treatment compound, and testing the cells for the levels of the biomarkers, wherein a decreased level of the biomarker in the presence of the treatment compound indicates the likelihood of responsiveness of the subject to the treatment compound.

In certain embodiments, the level of only one of the mRNA biomarkers is monitored. In certain embodiments, the levels of two or more of the mRNA biomarkers are monitored simultaneously.

4.4 TREATMENT COMPOUNDS

In some embodiments, the treatment compound is an immunomodulatory compound. In one embodiment, the treatment compounds encompass those immunomodulatory compounds known as IMIDS® from Celgene Corporation.

As used herein and unless otherwise indicated, the term "immunomodulatory compound" encompasses certain small organic molecules that inhibit LPS induced monocyte TNF-α, IL-1β, IL-12, IL-6, MIP-1α, MCP-1, GM-CSF, G-CSF, and COX-2 production. Specific immunomodulatory compounds are provided herein.

TNF-α is an inflammatory cytokine produced by macrophages and monocytes during acute inflammation. TNF-α is responsible for a diverse range of signaling events within cells. Without being limited by a particular theory, one of the biological effects exerted by the immunomodulatory compounds provided herein is the reduction of myeloid cell TNF-α production. In certain embodiments, the immunomodulatory compounds provided herein enhance the degradation of TNF-α mRNA.

Examples of the immunomodulatory compounds provided herein include, but are not limited to, cyano and carboxy derivatives of substituted styrenes, such as those disclosed in U.S. Pat. No. 5,929,117; 1-oxo-2-(2,6-dioxo-3-fluoropiperidin-3-yl)-isoindolines and 1,3-dioxo-2-(2,6-dioxo-3-fluoropiperidine-3-yl)-isoindolines, such as those described in U.S. Pat. Nos. 5,874,448 and 5,955,476; tetra substituted 2-(2,6-dioxopiperidin-3-yl)-1-oxoisoindolines, such as those described in U.S. Pat. No. 5,798,368; 1-oxo- and 1,3-dioxo-2-(2,6-dioxopiperidin-3-yl)-isoindolines (e.g., 4-methyl derivatives of thalidomide), substituted 2-(2,6-dioxopiperidin-3-yl)phthalimides, and substituted 2-(2,6-dioxopiperidin-3-yl)-1-oxoisoindoles, including, but not limited to, those disclosed in U.S. Pat. Nos. 5,635,517, 6,281,230, 6,316,471, 6,403,613, 6,476,052, and 6,555,554; 1-oxo- and 1,3-dioxoisoindolines substituted in the 4- or 5-position of the indoline ring (e.g., 4-(4-amino-1,3-dioxoisoindoline-2-yl)-4-carbamoylbutanoic acid) described in U.S. Pat. No. 6,380,239; isoindoline-1-one and isoindoline-1,3-dione substituted in the 2-position with 2,6-dioxo-3-hydroxypiperidin-5-yl (e.g., 2-(2,6-dioxo-3-hydroxy-5-fluoropiperidin-5-yl)-4-aminoisoindolin-1-one) described in U.S. Pat. No. 6,458,810; a class of non-polypeptide cyclic amides disclosed in U.S. Pat. Nos. 5,698,579 and 5,877,200; and isoindole-imide compounds, such as those described in U.S. Pat. App. Pub. Nos. 2003/0045552 and 2003/0096841, and International Pub. No. WO 02/059106. The disclosure of each of the patents and patent application publications identified herein is incorporated herein by reference in its entirety.

Various immunomodulatory compounds provided herein contain one or more chiral centers, and can exist as mixtures of enantiomers (e.g., racemic mixtures) or mixtures of diastereomers. The methods provided herein encompass the use of stereomerically pure forms of such compounds as well as mixtures of those forms. For example, mixtures comprising equal or unequal amounts of the enantiomers of a particular immunomodulatory compound may be used in methods provided herein. These isomers may be asymmetrically synthesized or resolved using standard techniques, such as chiral columns or chiral resolving agents. See, Jacques et al., *Enantiomers, Racemates and Resolutions* (Wiley-Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (Eliel, Ed., Univ. of Notre Dame Press, Notre Dame, Ind., 1972).

In certain embodiments, the immunomodulatory compound is an 1-oxo- or 1,3-dioxo-2-(2,6-dioxopiperidin-3-yl)-isoindoline substituted with amino in the benzo ring, including those described in U.S. Pat. No. 5,635,517, the disclosure of which is incorporated herein by reference in its entirety.

In certain embodiments, the immunomodulatory compound has the structure of Formula I:

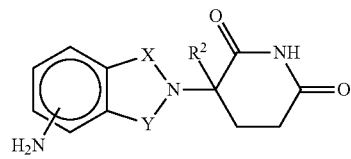

wherein one of X and Y is C=O, the other of X and Y is C=O or $CH_2$, and $R^2$ is hydrogen or lower alkyl, in one embodiment, methyl.

In certain embodiments, the immunomodulatory compound is:

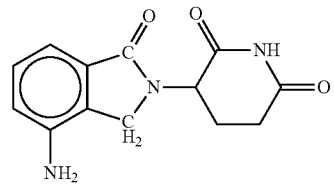

1-oxo-2-(2,6-dioxopiperidin-3-yl)-4-aminoisoindoline (lenalidomide);

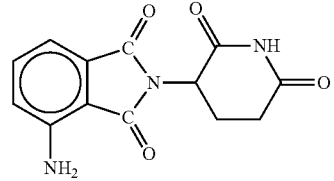

1,3-dioxo-2-(2,6-dioxopiperidin-3-yl)-4-aminoisoindoline (pomalidomide); or

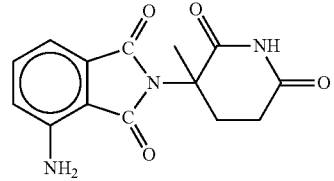

1,3-dioxo-2-(3-methyl-2,6-dioxopiperidin-3-yl)-4-aminoisoindole, or a optically pure isomer thereof. The immunomodulatory compounds can be obtained via standard, synthetic methods. See U.S. Pat. No. 5,635,517, the disclosure of which is incorporated herein by reference in its entirety. The immunomodulatory compounds are also available from Celgene Corporation, Warren, N.J.

In certain embodiments, the immunomodulatory compound is lenalidomide. In certain embodiments, the immunomodulatory compound is pomalidomide.

In certain embodiments, the immunomodulatory compound is a substituted 2-(2,6-dioxopiperidin-3-yl)-phthalimide or substituted 2-(2,6-dioxopiperidin-3-yl)-1-oxoisoindole, including those described in U.S. Pat. Nos. 6,281,230; 6,316,471; 6,335,349; and 6,476,052, and International Pub.

No. WO 98/03502, the disclosure of each of which is incorporated herein by reference in its entirety.

In certain embodiments, the immunomodulatory compound is of formula:

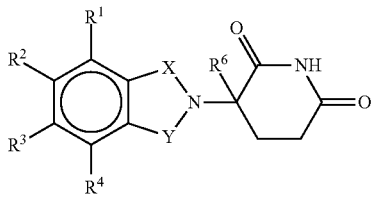

wherein:
one of X and Y is C=O and the other of X and Y is C=O or $CH_2$;
(i) each of $R^1$, $R^2$, $R^3$, and $R^4$, independently of the others, is halo, $C_{1-4}$ alkyl, or $C_{1-4}$ alkoxy; or (ii) one of $R^1$, $R^2$, $R^3$, and $R^4$ is —$NHR^5$ and the remaining of $R^1$, $R^2$, $R^3$, and $R^4$ are hydrogen;
$R^5$ is hydrogen or $C_{1-8}$ alkyl;
$R^6$ is hydrogen, $C_{1-8}$ alkyl, benzyl, or halo;
provided that $R^6$ is other than hydrogen if X and Y are C=O and (i) each of $R^1$, $R^2$, $R^3$, and $R^4$ is fluoro or (ii) one of $R^1$, $R^2$, $R^3$, or $R^4$ is amino.

In certain embodiments, the immunomodulatory compound is of formula

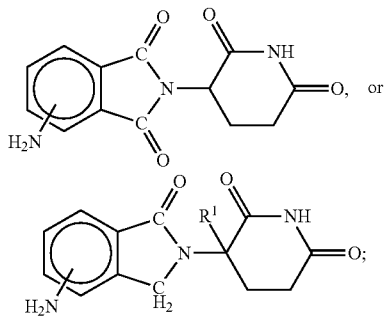

wherein $R^1$ is hydrogen or methyl.

In certain embodiments, the immunomodulatory compound used in the methods provided herein is enantiomerically pure (e.g. optically pure (R)- or (S)-enantiomers).

In another embodiment, the treatment compound is thalidomide, i.e., 2-(2,6-dioxopiperidin-3-yl)-1H-isoindole-1,3 (2H)-dione.

In other embodiments, the treatment compound is a 5-substituted quinazolinone, including those described in U.S. Pat. No. 7,635,700, the disclosure of which is incorporated herein by reference in its entirety.

In certain embodiments, the treatment compound is a compound having the structure of Formula IV:

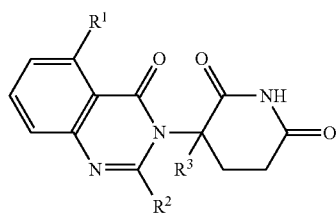

or a pharmaceutically acceptable salt, solvate, or stereoisomer thereof, wherein:
$R^1$ is:
hydrogen;
halo;
—$(CH_2)_n OH$;
$C_{1-6}$ alkyl, optionally substituted with one or more halo;
$C_{1-6}$ alkoxy, optionally substituted with one or more halo; or
—$(CH_2)_n NHR^a$, wherein $R^a$ is:
hydrogen;
$C_{1-6}$ alkyl, optionally substituted with one or more halo;
—$(CH_2)_n$-(6 to 10 membered aryl);
—$C(O)$—$(CH_2)_n$-(6 to 10 membered aryl) or —$C(O)$—$(CH_2)_n$-(5 to 10 membered heteroaryl), wherein the aryl or heteroaryl is optionally substituted with one or more of: halo; —$SCF_3$; $C_{1-6}$ alkyl, itself optionally substituted with one or more halo; or $C_{1-6}$ alkoxy, itself optionally substituted with one or more halo;
—$C(O)$—$C_{1-8}$ alkyl, wherein the alkyl is optionally substituted with one or more halo;
—$C(O)$—$(CH_2)_n$—$(C_3-C_{10}$-cycloalkyl);
—$C(O)$—$(CH_2)_n$—$NR^b R^c$, wherein $R^b$ and $R^c$ are each independently:
hydrogen;
$C_{1-6}$ alkyl, optionally substituted with one or more halo;
$C_{1-6}$ alkoxy, optionally substituted with one or more halo;
or
6 to 10 membered aryl, optionally substituted with one or more of: halo; $C_{1-6}$ alkyl, itself optionally substituted with one or more halo; or $C_{1-6}$ alkoxy, itself optionally substituted with one or more halo;
—$C(O)$—$(CH_2)_n$—O—$C_{1-6}$ alkyl; or
—$C(O)$—$(CH_2)_n$—O—$(CH_2)_n$-(6 to 10 membered aryl);
$R^2$ is: hydrogen; —$(CH_2)_n OH$; phenyl; —O—$C_{1-6}$ alkyl; or $C_{1-6}$ alkyl, optionally substituted with one or more halo;
$R^3$ is: hydrogen; or $C_{1-6}$ alkyl, optionally substituted with one or more halo; and
n is 0, 1, or 2.

In certain embodiments, the treatment compound is a compound having the structure of Formula V:

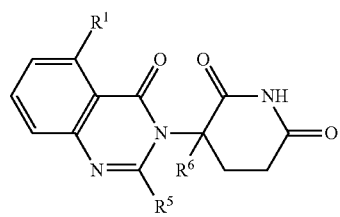

or a pharmaceutically acceptable salt, solvate, or stereoisomer thereof, wherein:
$R^4$ is: hydrogen; halo; —$(CH_2)_n OH$; $C_{1-6}$ alkyl, optionally substituted with one or more halo; or $C_{1-6}$ alkoxy, optionally substituted with one or more halo $R^5$ is: hydrogen; —$(CH_2)_n$OH; phenyl; —O—$C_{1-6}$ alkyl; or $C_{1-6}$ alkyl, optionally substituted with one or more halo;
$R^6$ is: hydrogen; or $C_{1-6}$ alkyl, optionally substituted with one or more halo; and
n is 0, 1, or 2.
In certain embodiments, the treatment compound is:
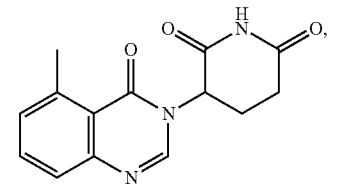
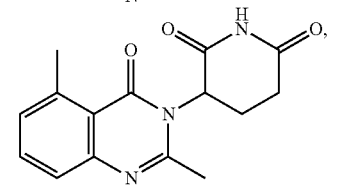
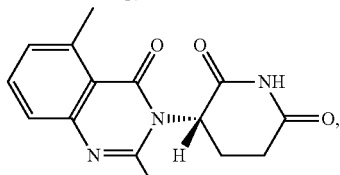
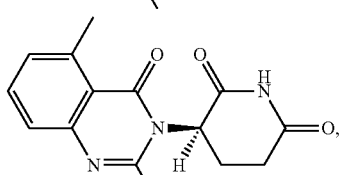
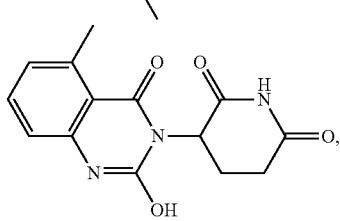
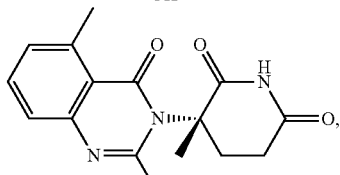
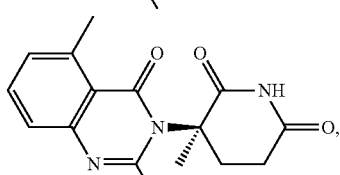
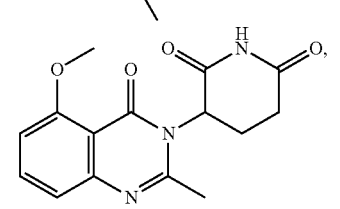
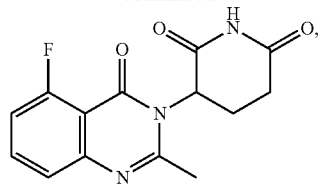
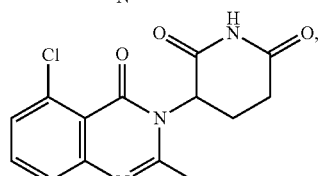
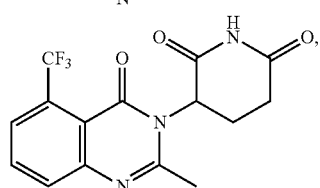
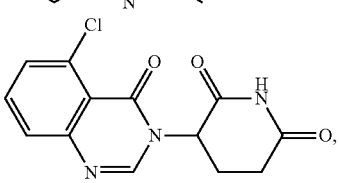
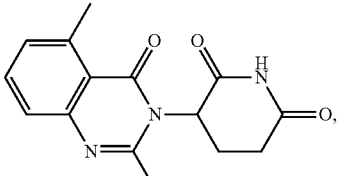
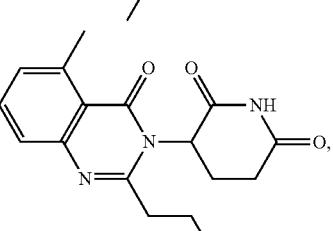
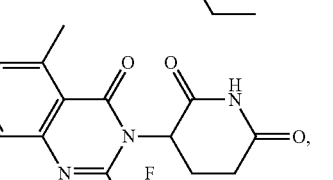
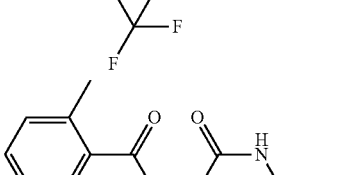 or
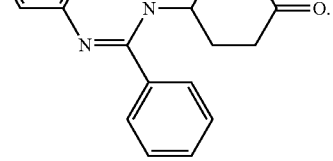

In certain embodiments, the treatment compound is a compound of Formula VI:

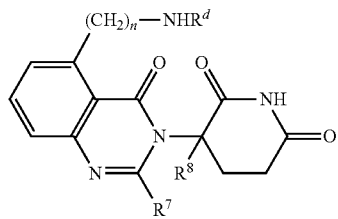

or a pharmaceutically acceptable salt, solvate, or stereoisomer thereof, wherein:

$R^d$ is: hydrogen;
  $C_{1-6}$ alkyl, optionally substituted with one or more halo;
  —C(O)—$C_{1-8}$ alkyl, wherein the alkyl is optionally substituted with one or more halo;
  —C(O)—$(CH_2)_n$—$C_{3-10}$ cycloalkyl;
  —C(O)—$(CH_2)_n$—$NR^eR^f$, wherein $R^e$ and $R^f$ are each independently:
    hydrogen;
    $C_{1-6}$ alkyl, optionally substituted with one or more halo; or
    $C_{1-6}$ alkoxy, optionally substituted with one or more halo; or
  —C(O)—$(CH_2)_n$—O—$C_{1-6}$ alkyl.
$R^7$ is: hydrogen; —$(CH_2)_n$OH; phenyl; —O—$C_{1-6}$ alkyl; or $C_{1-6}$ alkyl, optionally substituted with one or more halo;
$R^8$ is: hydrogen; or $C_{1-6}$ alkyl, optionally substituted with one or more halo; and
n is 0, 1, or 2.

In certain embodiments, the treatment compound is:

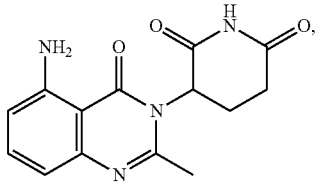

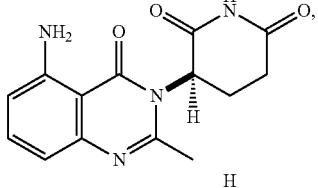

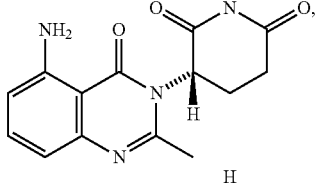

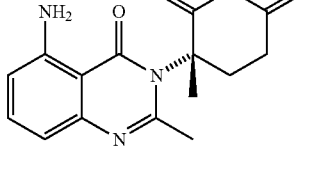

-continued

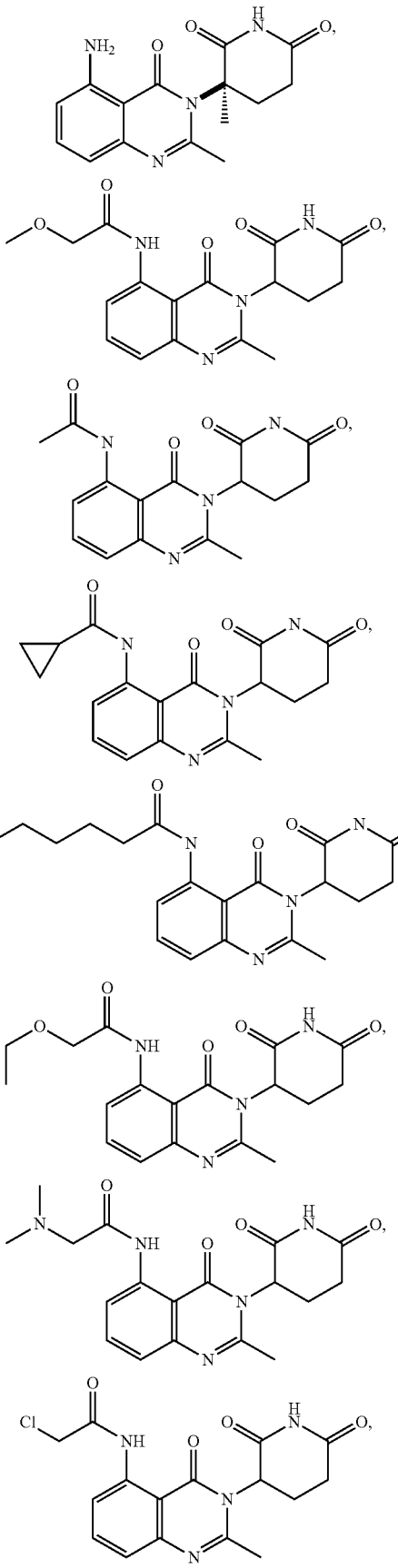

-continued

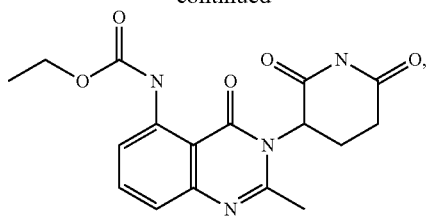

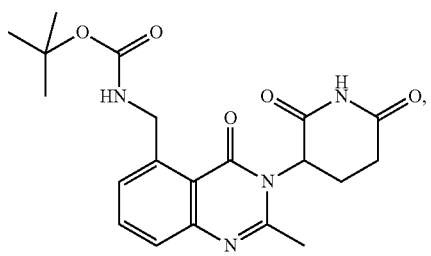

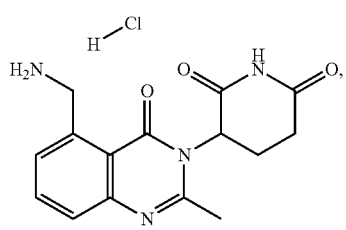

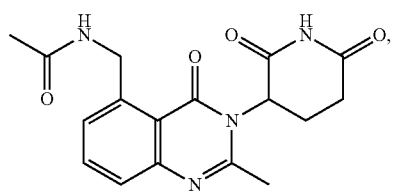

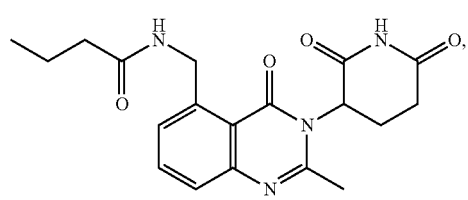

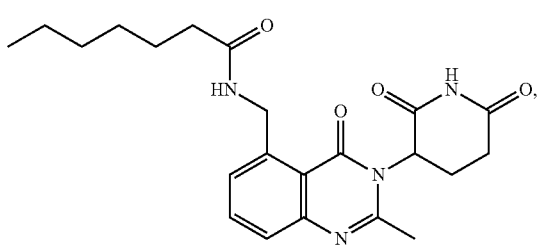

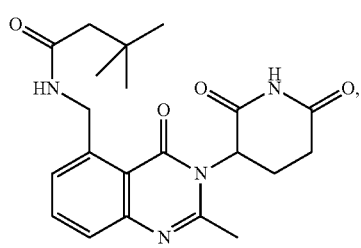

-continued

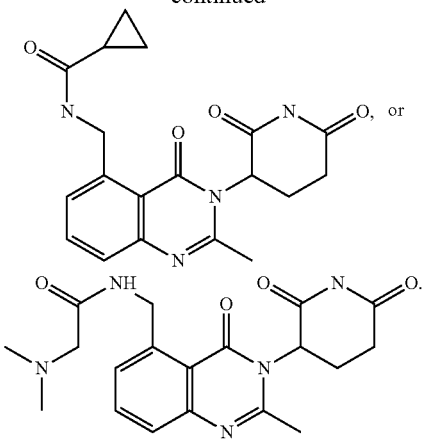

In certain embodiments, the treatment compound is 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

In certain embodiments, the treatment compound is a compound of Formula VII:

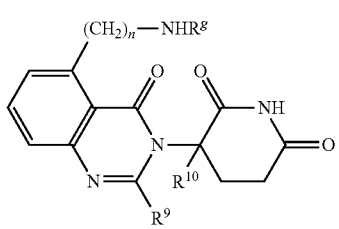

VII or a pharmaceutically acceptable salt, solvate, or stereoisomers thereof, wherein:

$R^8$ is: —$(CH_2)_n$-(6 to 10 membered aryl);

—C(O)—$(CH_2)_n$-(6 to 10 membered aryl) or —C(O)—$(CH_2)_n$-(5 to 10 membered heteroaryl), wherein the aryl or heteroaryl is optionally substituted with one or more of: halo; —$SCF_3$; $(C_1$-$C_6)$alkyl, itself optionally substituted with one or more halo; or $C_{1-6}$ alkoxy, itself optionally substituted with one or more halo;

—C(O)—$(CH_2)_n$—NHR$^h$, wherein R$^h$ is: 6 to 10 membered aryl, optionally substituted with one or more of: halo; $C_{1-6}$ alkyl, itself optionally substituted with one or more halo; or $C_{1-6}$ alkoxy, itself optionally substituted with one or more halo; or —C(O)—$(CH_2)_n$—O—$(CH_2)_n$-(6 to 10 membered aryl);

$R^9$ is: hydrogen; —$(CH_2)_n$OH; phenyl; —O—$C_{1-6}$ alkyl; or $C_{1-6}$ alkyl, optionally substituted with one or more halo;

$R^{10}$ is: hydrogen; or $C_{1-6}$ alkyl, optionally substituted with one or more halo; and n is 0, 1, or 2.

In certain embodiments, the treatment compound is:
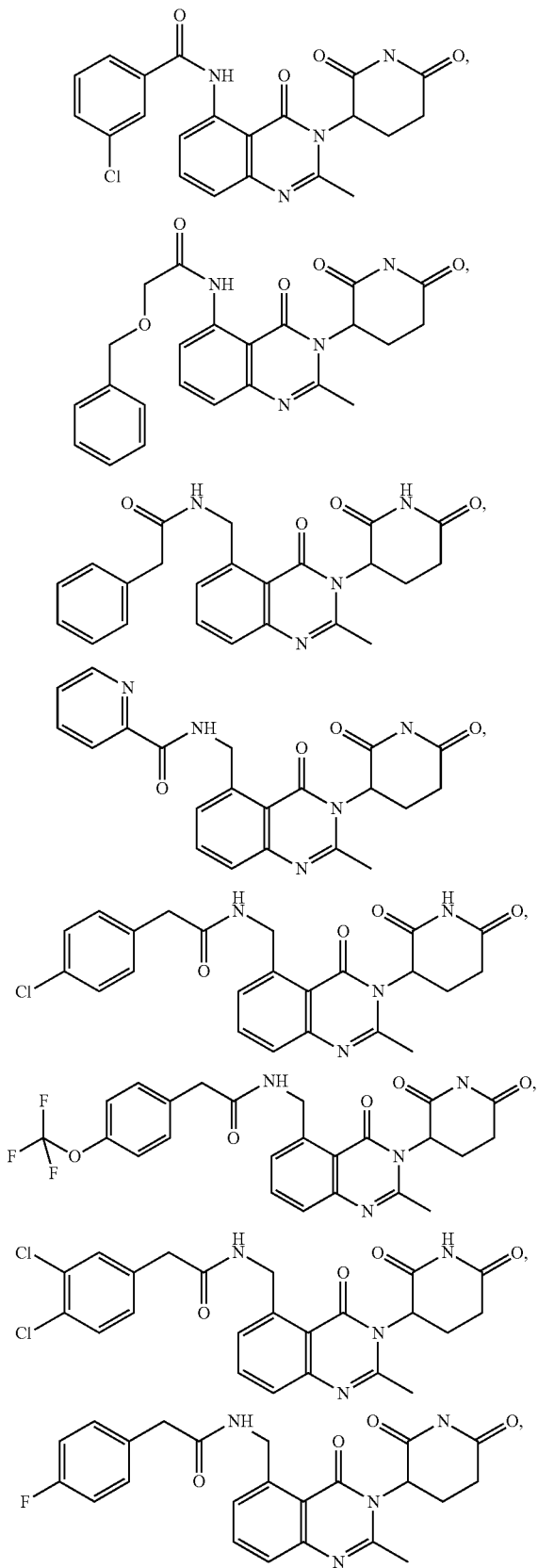
-continued
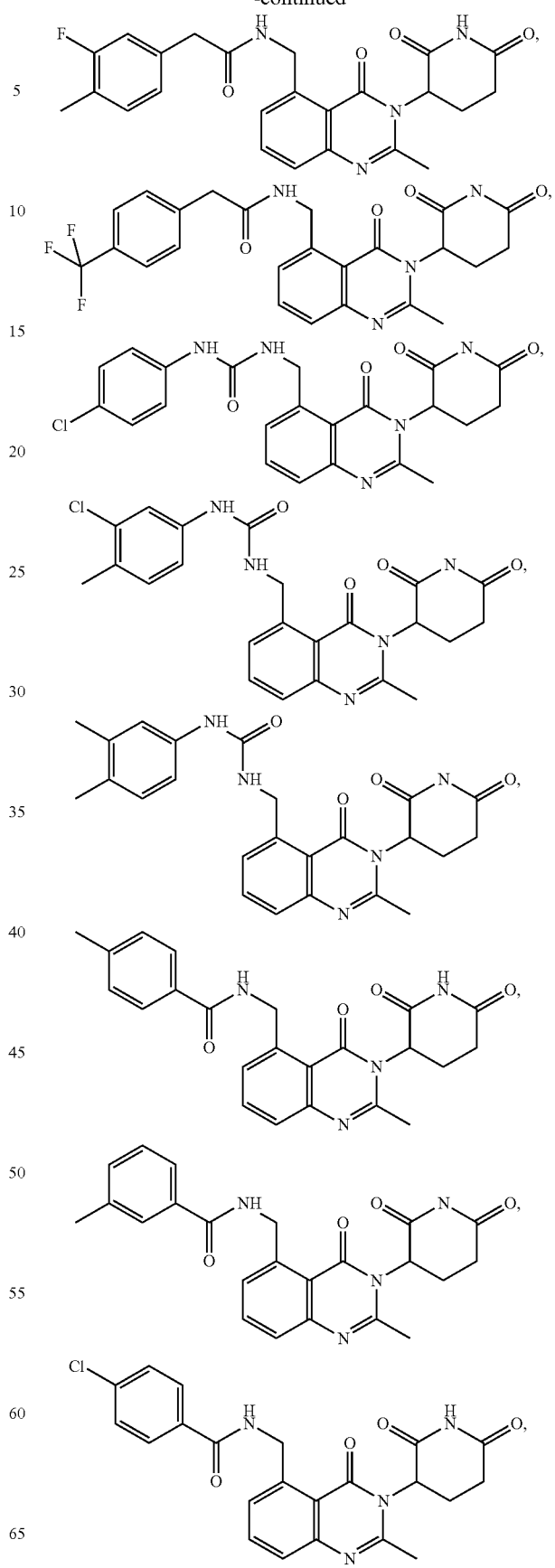

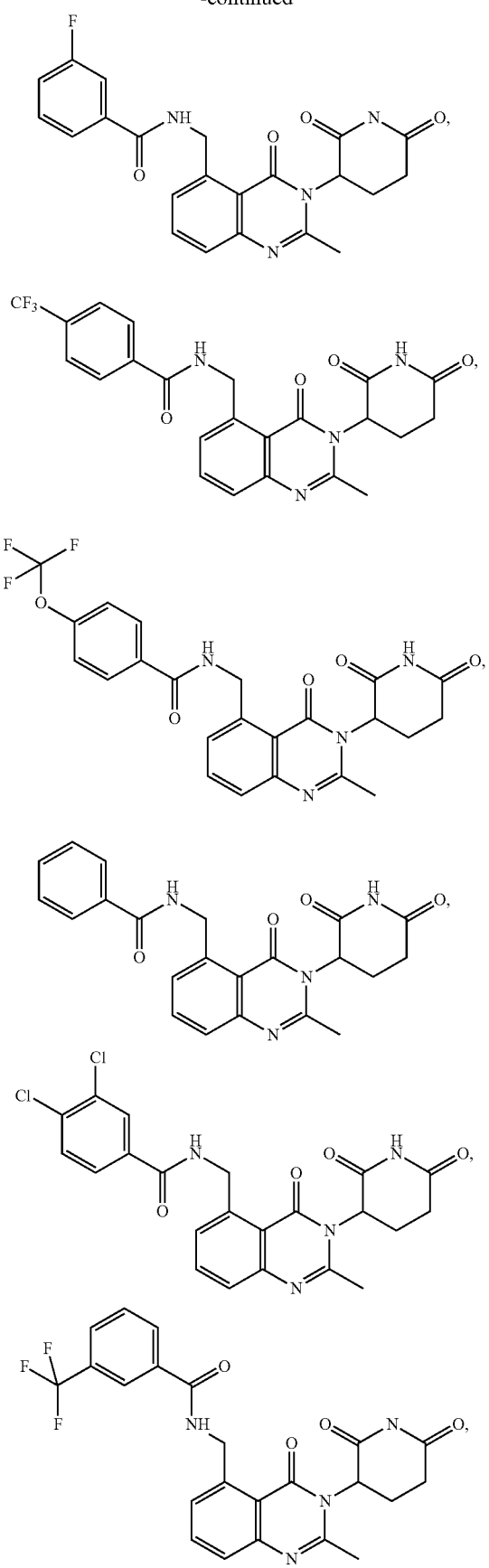

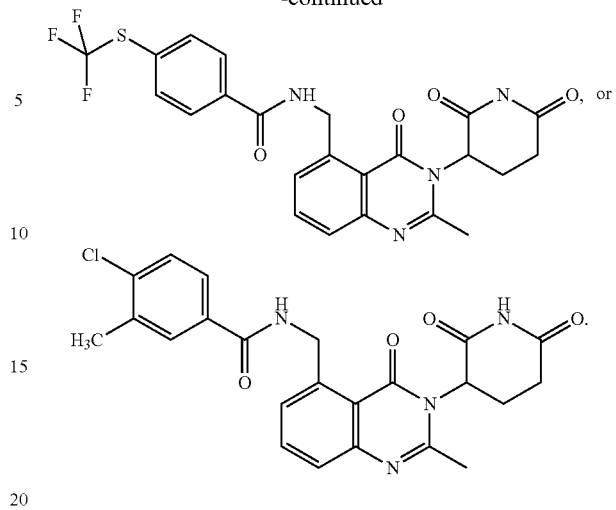

All of the compounds described herein can either be commercially purchased or prepared according to the methods described in the patents or patent publications disclosed herein. Further, optically pure compounds can be asymmetrically synthesized or resolved using known resolving agents or chiral columns as well as other standard synthetic organic chemistry techniques.

Compounds provided herein may be small organic molecules having a molecular weight less than about 1,000 g/mol, and are not proteins, peptides, oligonucleotides, oligosaccharides or other macromolecules.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

4.5 METHODS OF DETECTING BIOMARKER LEVELS

4.5.1 Methods of Detecting mRNA Levels in a Sample

Several methods of detecting or quantitating mRNA levels are known in the art and are suitable for use in the methods provided herein for measuring the level of the biomarker. Exemplary methods include, but are not limited to, northern blots, ribonuclease protection assays, and PCR-based methods. When the biomarker is an mRNA molecule, the mRNA sequence, or a fragment thereof, can be used to prepare a probe that is at least partially complementary. The probe can then be used to detect the mRNA sequence in a sample, using any suitable assay, such as PCR-based methods, Northern blotting, or a dipstick assay.

The assay method can be varied depending on the type of mRNA information desired. Exemplary methods include, but are not limited to, Northern blots and PCR-based methods (e.g., qRT-PCR). Methods such as qRT-PCR can also accurately quantitate the amount of the mRNA in a sample.

Any suitable assay platform can be used to determine the presence of the mRNA in a sample. For example, an assay may be in the form of a dipstick, a membrane, a chip, a disk, a test strip, a filter, a microsphere, a slide, a multiwell plate, or an optical fiber. An assay system may have a solid support on which a nucleic acid corresponding to the mRNA is attached. The solid support may comprise, for example, a plastic, silicon, a metal, a resin, glass, a membrane, a particle, a precipitate, a gel, a polymer, a sheet, a sphere, a polysaccharide, a capillary, a film a plate, or a slide. The assay components can be prepared and packaged together as a kit for detecting an mRNA.

The nucleic acid can be labeled, if desired, to make a population of labeled mRNAs. In general, a sample can be labeled using methods that are well known in the art (e.g., using DNA ligase, terminal transferase, or by labeling the RNA backbone, etc.; see, e.g., Ausubel, et al., *Short Protocols in Molecular Biology*, 3rd ed., Wiley & Sons 1995 and Sambrook et al., *Molecular Cloning: A Laboratory Manual*, Third Edition, 2001 Cold Spring Harbor, N.Y.). In certain embodiments, the sample is labeled with fluorescent label. Exemplary fluorescent dyes include, but are not limited to, xanthene dyes, fluorescein dyes, rhodamine dyes, fluorescein isothiocyanate (FITC), 6-carboxyfluorescein (FAM), 6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine 6G (R6G5 or G5), 6-carboxyrhodamine 6G (R6G6 or G6), and rhodamine 110; cyanine dyes, e.g. Cy3, Cy5 and Cy7 dyes; Alexa dyes, e.g. Alexa-fluor-555; coumarin, diethylaminocoumarin, umbelliferone; benzimide dyes, e.g. Hoechst 33258; phenanthridine dyes, e.g., Texas red; ethidium dyes; acridine dyes; carbazole dyes; phenoxazine dyes; porphyrin dyes; polymethine dyes, BODIPY dyes, quinoline dyes, pyrene, fluorescein chlorotriazinyl, R110, Eosin, JOE, R6G, tetramethylrhodamine, lissamine, ROX, and napthofluorescein.

The nucleic acids may be present in specific, addressable locations on a solid support; each corresponding to at least a portion of mRNA sequences of a biomarker.

In certain embodiments, an mRNA assay comprises the steps of 1) obtaining surface-bound probes for one or more biomarkers; 2) hybridizing a population of mRNAs to the surface-bound probes under conditions sufficient to provide for specific binding; (3) removing unbound nucleic acids in the hybridization step; and (4) detecting the hybridized mRNAs.

Hybridization can be carried out under suitable hybridization conditions, which may vary in stringency as desired. Typical conditions are sufficient to produce probe/target complexes on a solid surface between complementary binding members, i.e., between surface-bound probes and complementary mRNAs in a sample.

In certain embodiments, stringent hybridization conditions are used. Standard hybridization techniques (e.g., under conditions sufficient to provide for specific binding of target mRNAs in the sample to the probes) are described in Kallioniemi et al., *Science* 258:818-821 (1992) and WO 93/18186, the disclosure of each which is incorporated herein by reference in its entirety. Several guides to general techniques are available, e.g., Tijssen, *Hybridization with Nucleic Acid Probes*, Parts I and II (Elsevier, Amsterdam 1993). For descriptions of techniques suitable for in situ hybridizations, see Gall et al. *Meth. Enzymol.*, 21:470-480 (1981); and Angerer et al. in *Genetic Engineering Principles and Methods* (Setlow and Hollaender, Eds.) Vol 7, pages 43-65 (Plenum Press, New York 1985). Selection of appropriate conditions, including temperature, salt concentration, polynucleotide concentration, hybridization time, and stringency of washing conditions, depends on experimental design, including the source of a sample, the identity of capture agents, the degree of complementarity expected, etc., and may be determined as a matter of routine experimentation for those of ordinary skill in the art.

After the mRNA hybridization procedure, the surface bound polynucleotides are washed to remove unbound nucleic acids. Washing may be performed using any convenient washing protocol. In certain embodiments, the washing conditions are stringent. The hybridization of the target mRNAs to the probes is then detected using standard techniques.

4.5.2 PCR-Based Methods of Detecting mRNA Levels in a Sample

In certain embodiments, the mRNA level of a biomarker is determined using a PCR-based method. Examples of PCR assays can be found in U.S. Pat. No. 6,927,024, the disclosure of which is incorporated by reference herein in its entirety. Examples of RT-PCR methods can be found in U.S. Pat. No. 7,122,799, the disclosure of which is incorporated by reference herein in its entirety. Examples of fluorescent in situ PCR methods can be found in U.S. Pat. No. 7,186,507, the disclosure of which is incorporated by reference herein in its entirety.

In certain embodiments, real-time reverse transcription-PCR (qRT-PCR) is used for both the detection and quantification of mRNAs (Bustin, et al., *Clin. Sci.*, 2005, 109, 365-379). Quantitative results obtained by qRT-PCR are generally more informative than qualitative data. Examples of qRT-PCR-based methods can be found in U.S. Pat. No. 7,101,663, the disclosure of which is incorporated by reference herein in its entirety.

In contrast to regular reverse transcriptase-PCR and analysis by agarose gels, real-time PCR gives quantitative results. An additional advantage of real-time PCR is the relative ease and convenience of use. Instruments for real-time PCR, such as Applied Biosystems 7500, are available commercially. The reagents for real-time PCR, such as TaqMan Sequence Detection chemistry, are also commercially available.

To determine the cycle number at which the fluorescence signal associated with a particular amplicon accumulation crosses the threshold (referred to as CT), the data can be analyzed, for example, using a 7500 Real-Time PCR System Sequence Detection software v1.3, using the comparative CT relative quantification calculation method. Using this method, the output is expressed as a fold-change in expression levels. In some embodiments, the threshold level can be selected to be automatically determined by the software. In some embodiments, the threshold level is set to be above the baseline, but sufficiently low to be within the exponential growth region of an amplification curve.

4.5.3 Methods of Detecting Polypeptide or Protein Biomarkers

When the biomarker is a protein, polypeptide, or peptide, several protein detection and quantitation methods can be used to measure the level of the biomarker. Any suitable protein quantitation method can be used in the methods provided herein. In certain embodiments, antibody-based methods are used. Exemplary methods that can be used include, but are not limited to, immunoblotting (western blot), enzyme-linked immunosorbent assay (ELISA), immunohistochemistry, flow cytometry, cytometric bead array, and mass spectroscopy. Several types of ELISA are commonly used, including direct ELISA, indirect ELISA, and sandwich ELISA.

4.6 KITS FOR DETECTING BIOMARKER LEVELS

In certain embodiments, provided herein is a kit for detecting the mRNA level of one or more biomarkers. In certain embodiments, the kit comprises one or more probes that bind specifically to the mRNAs of the one or more biomarkers. In certain embodiments, the kit further comprises a washing solution. In certain embodiments, the kit further comprises reagents for performing a hybridization assay, mRNA isolation or purification means, detection means, as well as positive and negative controls. In certain embodiments, the kit further comprises an instruction for using the kit. The kit can be tailored for in-home use, clinical use, or research use.

In certain embodiments, provided herein is a kit for detecting the protein level of one or more biomarkers. In certain embodiments, the kits comprises a dipstick coated with an antibody that recognizes the protein biomarker, washing solutions, reagents for performing the assay, protein isolation or purification means, detection means, as well as positive and negative controls. In certain embodiments, the kit further comprises an instruction for using the kit. The kit can be tailored for in-home use, clinical use, or research use.

Such a kit can employ, for example, a dipstick, a membrane, a chip, a disk, a test strip, a filter, a microsphere, a slide, a multiwell plate, or an optical fiber. The solid support of the kit can be, for example, a plastic, silicon, a metal, a resin, glass, a membrane, a particle, a precipitate, a gel, a polymer, a sheet, a sphere, a polysaccharide, a capillary, a film, a plate, or a slide. The biological sample can be, for example, a cell culture, a cell line, a tissue, an oral tissue, gastrointestinal tissue, an organ, an organelle, a biological fluid, a blood sample, a urine sample, or a skin sample.

5. EXAMPLES

The examples below are carried out using standard techniques, which are well known and routine to those of skill in the art, except where otherwise described in detail. The examples are intended to be merely illustrative.

5.1 Effect of Lenalidomide on TCF-4 Transcription Factor in HCC Cell Lines

Focus and Hub7 cells were treated with 10 µM of lenalidomide ("LM") in DMSO or DMSO as a control for 24 hrs. Nuclear and cytosolic proteins were separately extracted and the expression of TCF-4 was analyzed by western blot. Nuclear expression of both long and short isoforms of TCF-4 was qualified using ImageJ (NIH) and normalized by expression of lamin. As shown in FIG. 1, upon LM treatment, TCF-4 expression, short and long forms, was decreased in poorly-differentiated cells (Focus).

Figure 2:
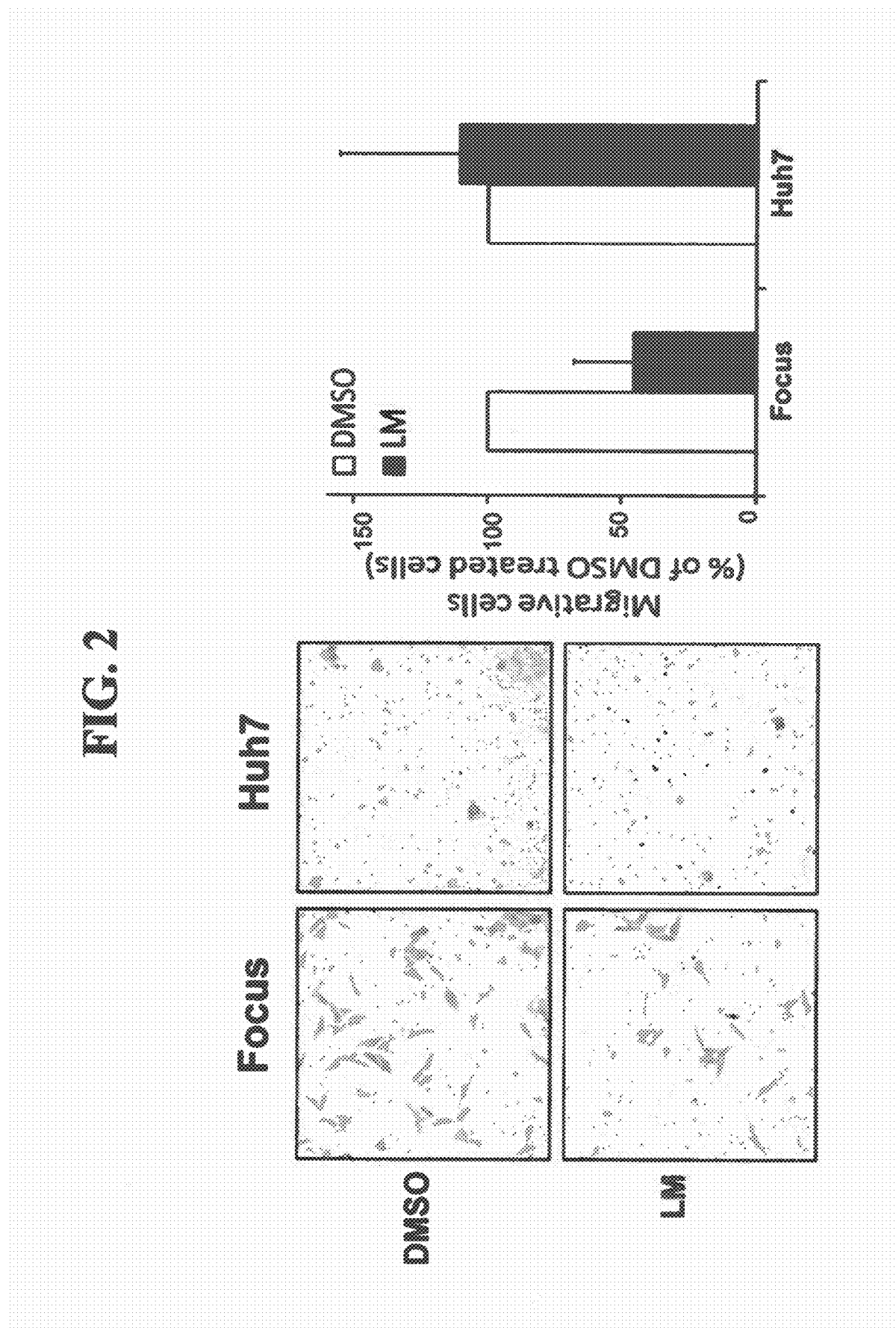
FIG. 2 shows the change in cell migration in HCC cell lines, Focus and Hub7, upon treatment with LM.

5.2 Effect of Lenalidomide and 3-(5-amino-2-methyl-4-oxo-4H-quinazolin-3-yl)-piperidine-2,6-dione on Cell Migration and Invasion Cell Migration Assay:

Focus and Hub7 cells were treated with 10 µM of LM in DMSO or DMSO as a control for 24 hrs. The cells were transferred in a migration chamber (BD Biosciences). The lower chamber was filled with 10% FBS-containing medium as a chemoattractant and was separated from the upper chamber by a 8 µm pore membrane. After 16 hrs, the remaining cells in the upper chamber (non-migrated cells) were removed and the cell attached to the bottom of the membrane (migrated cells) were stained with crystal violet and counted using Stereologer (SRC) in 10 different fields of the membrane. As shown in FIG. 2, LM treatment inhibited cell migration in a poorly differentiated HCC cell line (Focus).

Cell Invasion Assay:

Focus and Hub7 cells were treated with 10 µM of LM in DMSO or DMSO as a control for 24 hrs. The cells were transferred in a migration chamber coated with Matrigel (BD Biosciences). After 16 hrs, invasive cells attached to the bottom of the membrane were stained/counted and normalized by the number of migrative cells in a corresponding non-coated migration chamber. FIG. 2 also shows that LM treatment inhibited cell invasion in a poorly differentiated HCC cell line (Focus).

Figure 3:
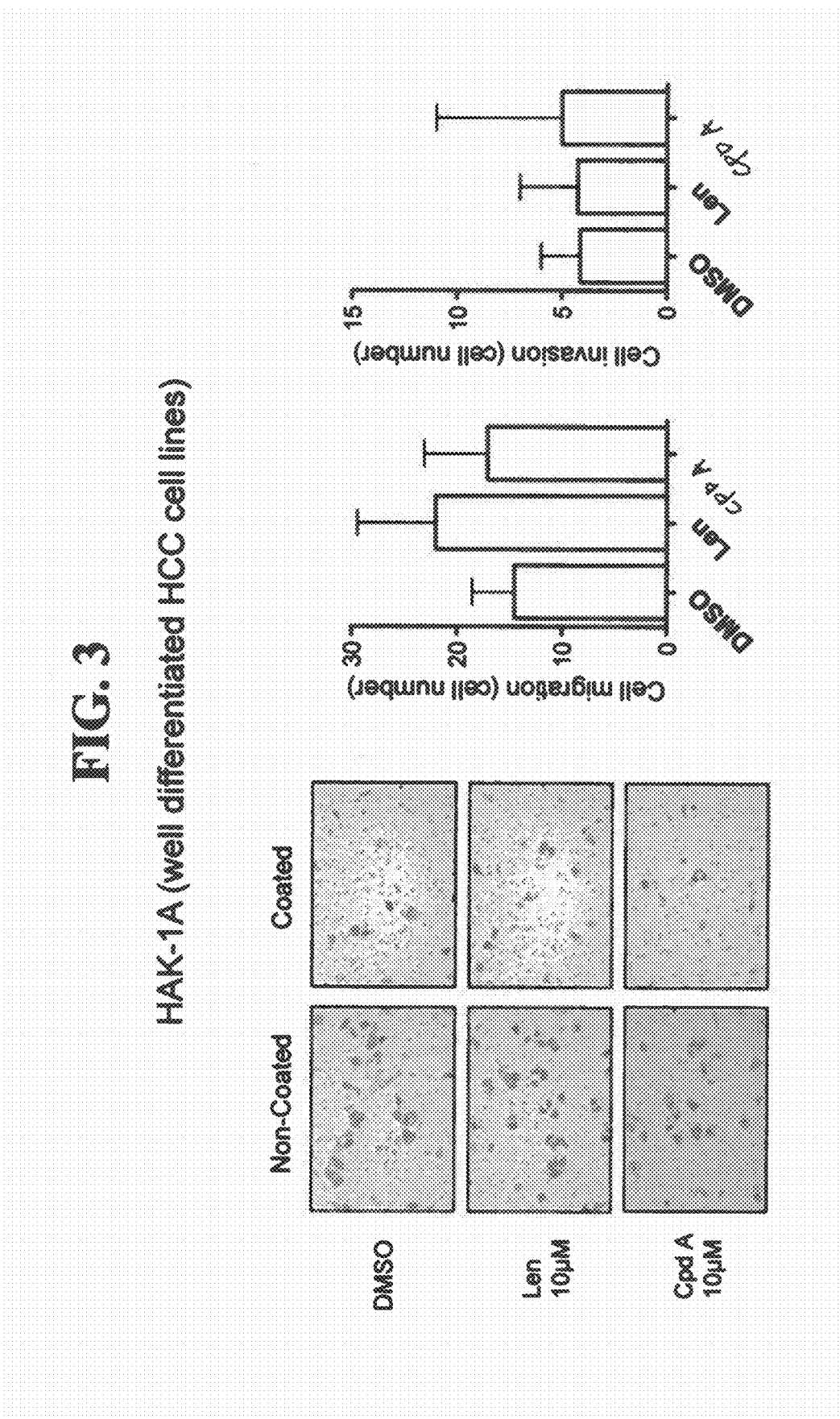
FIG. 3 shows the effect of LM and 3-(5-amino-2-methyl-4-oxo-4H-quinazolin-3-yl)-piperidine-2,6-dione ("Compound A") on HCC cell migration and invasion in well differentiated HAK-1A cell line.

In another set of experiments, the effects of LM and 3-(5-amino-2-methyl-4-oxo-4H-quinazolin-3-yl)-piperidine-2,6-dione ("Compound A") on HCC cell migration were assessed using procedures similar to those described above, except that HAK-1A cell line (well differentiated HCC cell line) was employed. As shown in FIG. 3, it was found that LM and Compound A did not affect the cell migration in HAK-1A cell line.

Figure 4:
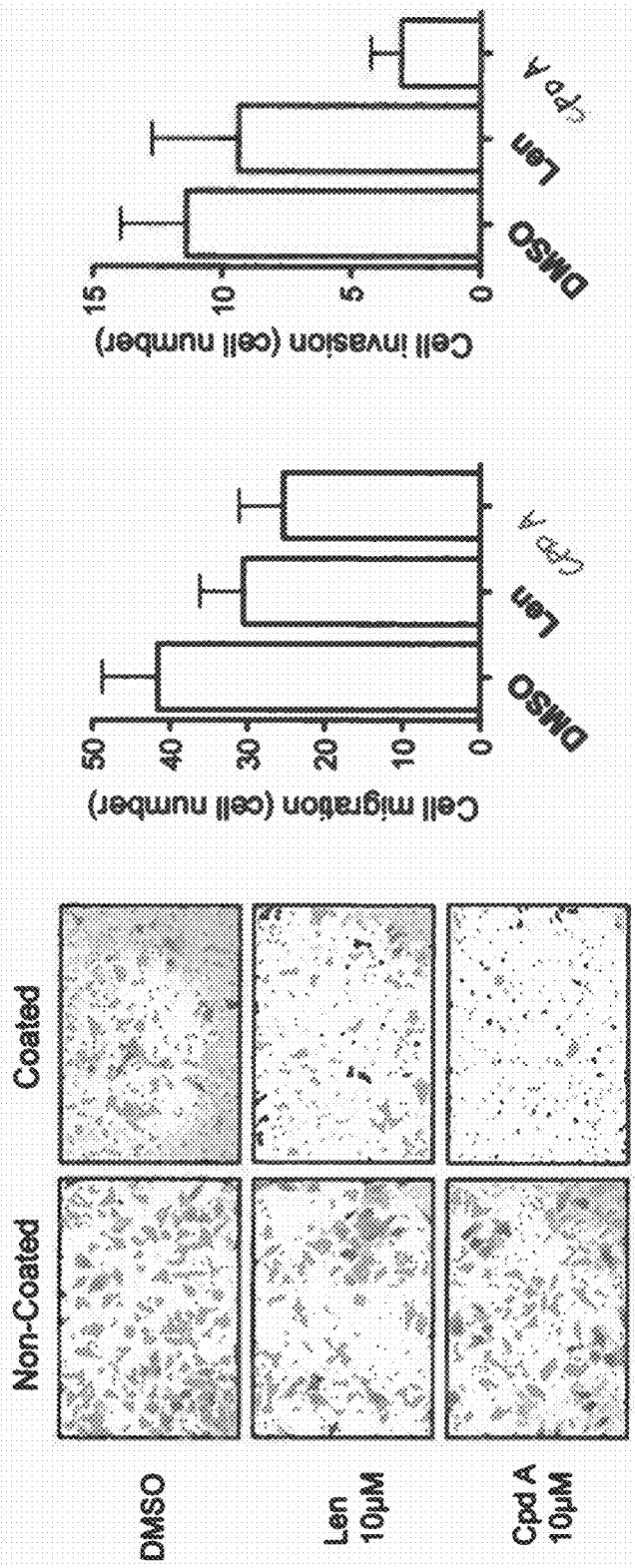
FIG. 4 shows the effect of LM and Compound A on HCC cell migration and invasion in poorly differentiated HAK-1B cell line.

In another set of experiments, the effects of LM and Compound A on HCC cell migration and invasion were assessed using procedures similar to those described above, except that HAK-1B cell line (poorly differentiated HCC cell line) was employed. As shown in FIG. 4, it was found that LM and Compound A inhibited cell migration in poorly differentiated HAK-1B HCC cell line. In addition, it was found that Compound A (and LM to a much lower degree) inhibited cell invasion in poorly differentiated HAK-1AB HCC cell line.

Figure 5:
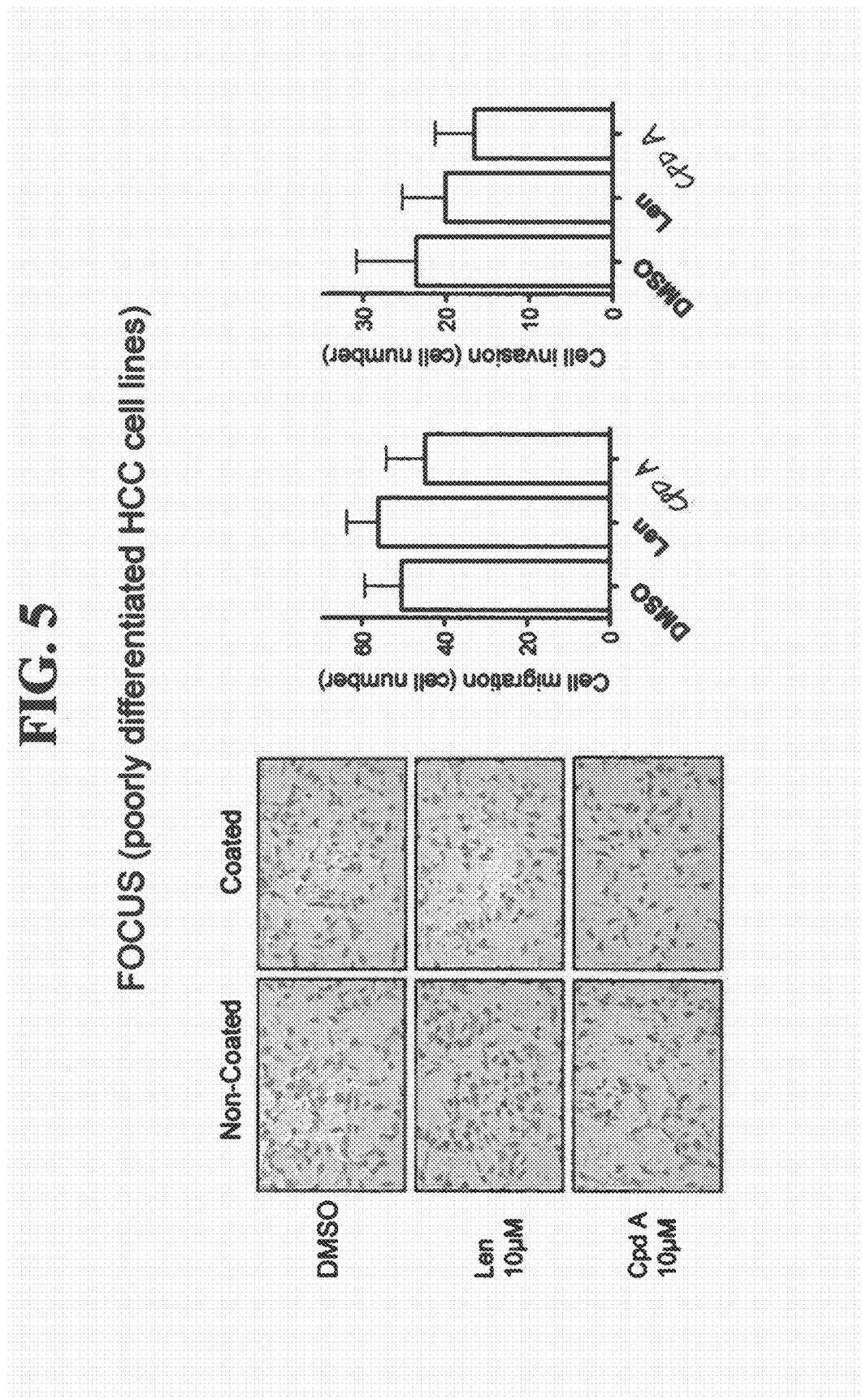
FIG. 5 shows the effect of LM and Compound A on HCC cell migration and invasion in well differentiated FOCUS cell line.

In another set of experiments, the effects of LM and Compound A on HCC cell migration and invasion were assessed using procedures similar to those described above using FOCUS cell line (poorly differentiated HCC cell line). As shown in FIG. 5, it was found that LM and Compound A did not inhibit cell migration of poorly differentiated FOCUS HCC cells. However, it was found that LM and Compound A inhibited cell invasion of poorly differentiated FOCUS HCC cells.

In another set of experiments, the effects of LM and Compound A on HCC cell migration were assessed using wound healing assay in HAK-1A cell line (well differentiated HCC cell line). The following procedures were used.

1. Cell seeding: A grid on the underside of the plate (60 mm) was drawn according to the paper diagram. Cells were seeded on 60 mm dish (aimed for confluent cells).

2. Scratch wound: Using a tip (green), a scratch wound was made. The locations of the wounds were recorded by drawing on a paper. SF DMEM+trypsin aliquot was retrieved from the incubator, and the media/floating cells from the dish was aspirated. Cells were washed with DMEM+Trypsin to remove cells that have not been completely scratched away from the wound. Then the dish was filled with 4 ml of 10% FBS DMEM.

3. Taking photographs: The marker was included on the top of the image frame so the same wound area can be kept track of. Then pictures of those wounds for the indicated time points were taken. Results were expressed as percentage of wound closure, as an index of cell migration, normalized to the initial width.

Figure 6:
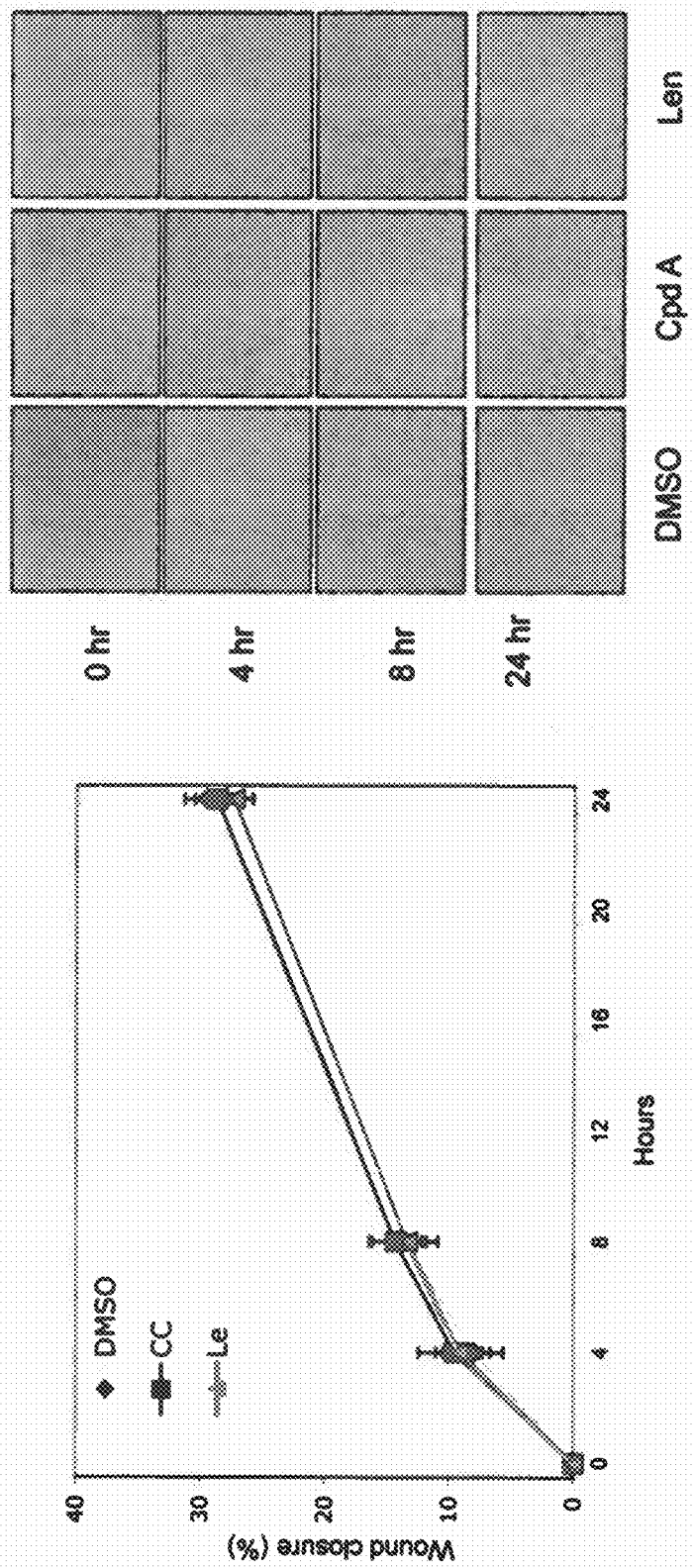
FIG. 6 shows the effect of LM and Compound A on HCC cell migration in well differentiated HAK-1A cell line using wound healing assay.

As shown in FIG. 6, it was found that LM and Compound A did not affect the cell migration in HAK-1A cell line.

Figure 7:
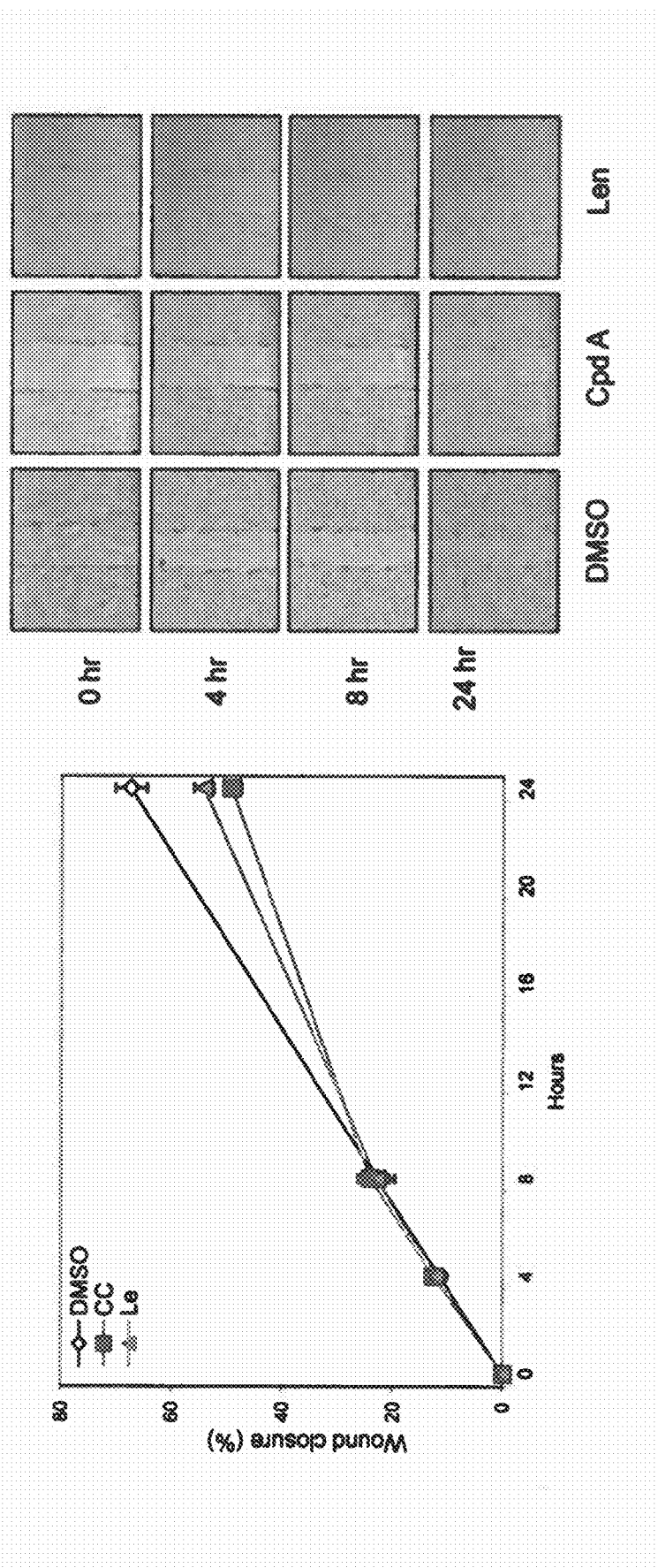
FIG. 7 shows the effect of LM and Compound A on HCC cell migration in poorly differentiated FOCUS cell line using wound healing assay.

In another set of experiments, the effects of LM and Compound A on HCC cell migration were assessed using wound healing assay in FOCUS cell line (poorly differentiated HCC cell line). As shown in FIG. 7, it was found that LM and Compound A reduced cell migration in poorly differentiated FOCUS cell line.

Figure 8:
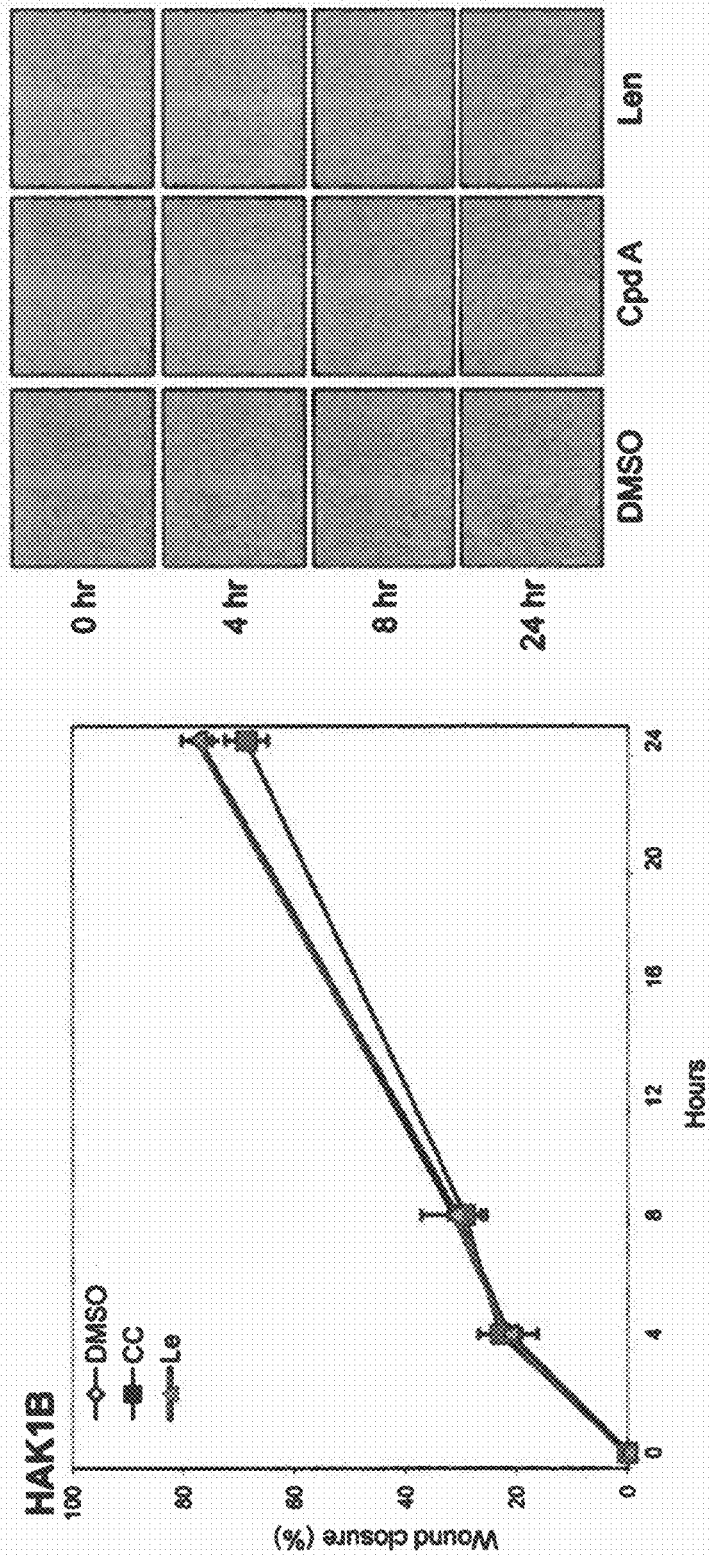
FIG. 8 shows the effect of LM and Compound A on HCC cell migration in poorly differentiated HAK-1B cell line using wound healing assay.

In another set of experiments, the effects of LM and Compound A on HCC cell migration were assessed using wound healing assay in HAK-1B cell line (poorly differentiated HCC cell line). As shown in FIG. 8, it was found that Compound A, but not LM, reduced cell migration in poorly differentiated HAK-1B cell line.

5.3 TCF Transcriptional Activity of TCF-4 Isoforms

Figure 9:
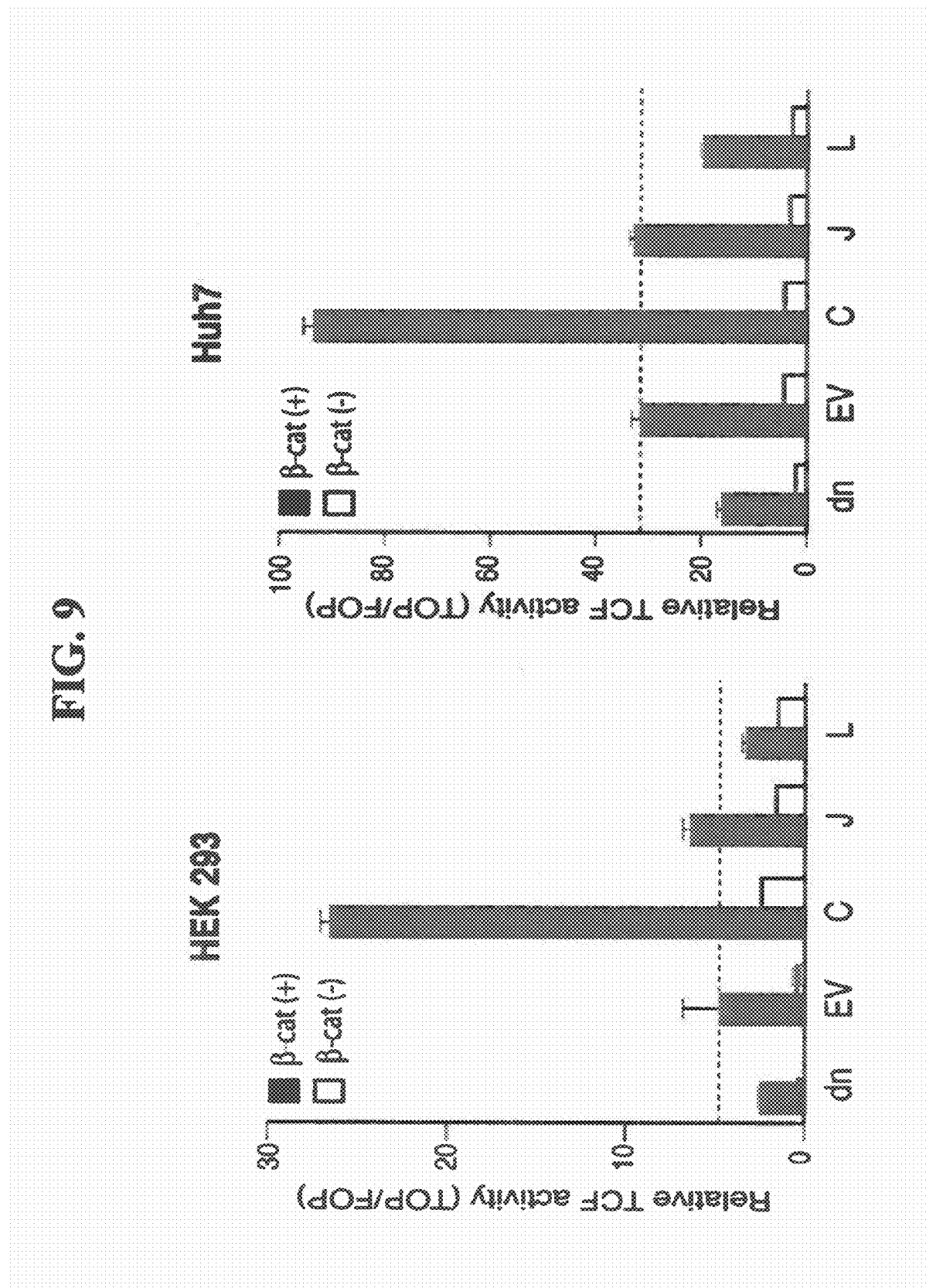
FIG. 9 shows the TCF transcriptional activity of TCF-4 isoforms in a HCC cell line (Huh7) and a non-HCC cell line (HEK 293).

Cells (HEK 293 and Huh7) were co-transfected with the TCF-reporter plasmid TOPFlash and isoforms C, J, or L of TCF-4 and β-catenin as a co-activator. An empty vector (EV) was used as a control for the basal level of TCF activity and a dominant negative form (dn) of TCF-4 for the assessment of repressed TCF transcriptional activity. Twenty-four hours after transfection, cells were lyzed and the expression of the reporter gene (luciferase) was quantified by chemoluminescence using the Luciferase Assay System (Promega). Transcriptional activity of TCF-4 isoforms is shown in FIG. 9.

5.4 Expression Profile of TCF-4 Isoforms in Human HCC Tissues

Figure 10:
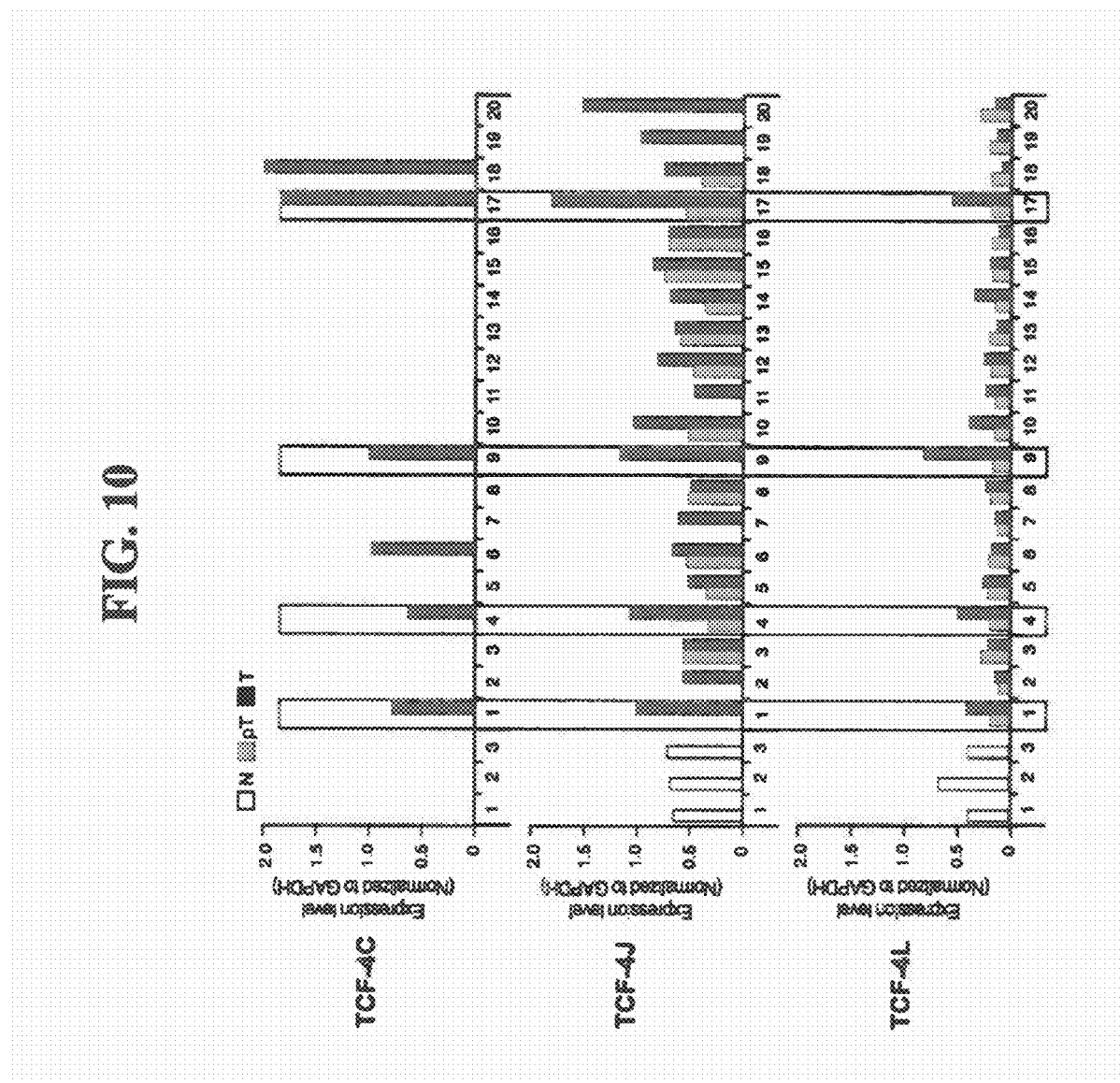
FIG. 10 shows the expression profile of TCF-4C, J, and L isoforms in human HCC tumor tissues.

The relative mRNA levels of TCF-4C, J, and L in 20 pairs of HCC tumors and corresponding adjacent uninvolved liver tissue obtain from individuals where 85% (17/20) of the tumors were related to chronic HCV infection were measured. Comparisons were made to three histologically normal liver specimens by semi-quantitative RT-PCR. Among the 20 paired samples, upregulation of all three isoforms, i.e., TCF-4C, J, and L, was found in 4 tumor tissues (FIG. 10). In FIG. 10, N, pT, and T stand for normal liver specimens, peritumor tissues, and tumor tissues, respectively.

Figure 11:
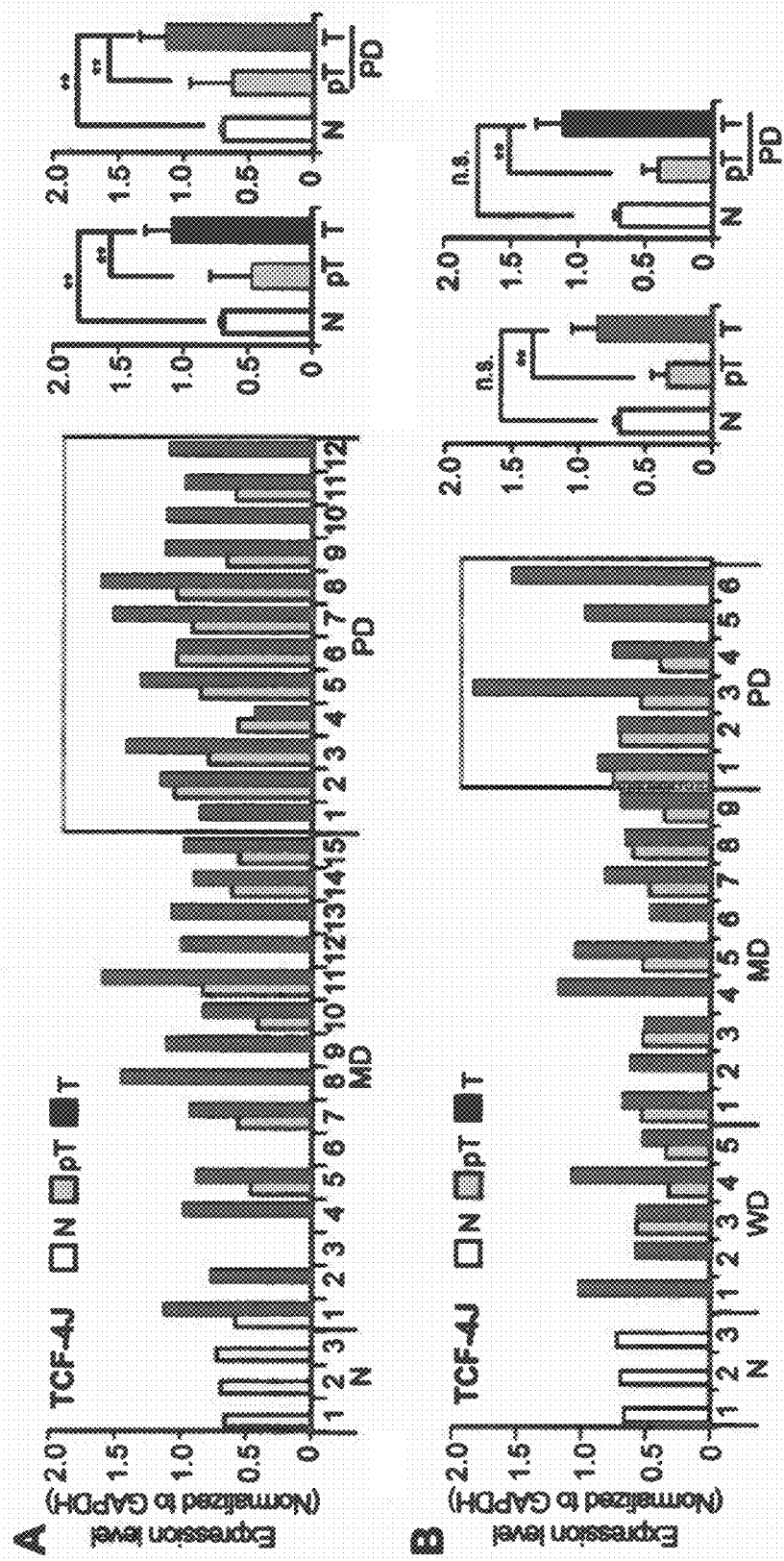
FIG. 11A shows the upregulation of TCF-4J expression in human HCC cells (HBV-related tumor and adjacent peritumor).
FIG. 11B shows the upregulation of TCF-4J expression in human HCC cells (HCV-related tumor).

In another set of experiments, the level of TCF-4J mRNA was measured by RT-PCR in 27 paired HBV-related HCC tumor and corresponding adjacent peritumor (FIG. 11A) and in 20 paired HCV-related HCC tumor (FIG. 11B). Right panels on FIGS. 11A and 11B show average of the TCF-4J mRNA expression level. As shown in these figures, it was found that TCF-4J was significantly upregulated in tumor, especially in poorly differentiated tumor.

5.5 Effect of TCF-4J Expression on the Growth of Xenografted Tumors in Nude Mice HAK-1A-derived stable clones were used for xenograft experiments; parental HAK-1A cells do not form tumors in nude mice. TCF-4J-overexpressing HAK-1A stable clones (J cells) were highly tumorigenic. Although K cells generated small tumors, they appeared later (about 40 days) after tumor cell injection and grew very slowly. Control (EV) cells did not produce tumors. Cells ($1\times10^6$) were s.c. injected into 5-wk old male BALB/c nude mice (n=12). The tumor size was measured in two orthogonal directions using electric calipers twice per week. When the longer diameter reached 10 mm, the mice were sacrificed. As shown in FIG. 12, TCF-4J isoform expression promoted tumorigenesis.

5.6 Upregulation of TCF-4J Dependent Target Genes

Total RNA (50 ng) extracted from HAK-1A-J or -K overexpressing stable cells by using Trizol was labeled with Agilent Low-Input QuickAmp Labeling Kit. Whole genome expression profiling was conducted in Whole Human Genome Microarray Kit, 4×44k, which included five glass slides each formatted with four high-definition 44k arrays (Agilent Technologies). Data analysis was performed by using Feature Extraction software (Agilent) and the result is summarized in Table 1.

TABLE 1

| | Gene Upregulation | | |
|---|---|---|---|
| Gene | Ratio (J/K) | TCF-4J | TCF-4K |
| WISP2 | 9.4 | 1956 | 208 |
| ASPH | 2.4 | 1400 | 585 |
| IRS1 | 3.4 | 286 | 84 |
| MAPK12 | 2.9 | 120 | 41 |
| JAG1 | 2.1 | 466 | 227 |

The list of TCF-4J isoform-dependent upregulated target genes in HAK-1A cell line is provided in FIG. 13. It was found that these genes are related to three pathways, i.e., Wnt/β-catenin, IRS-1, and Notch signaling, which are known to be important in HCC pathogenesis.

Figure 14:
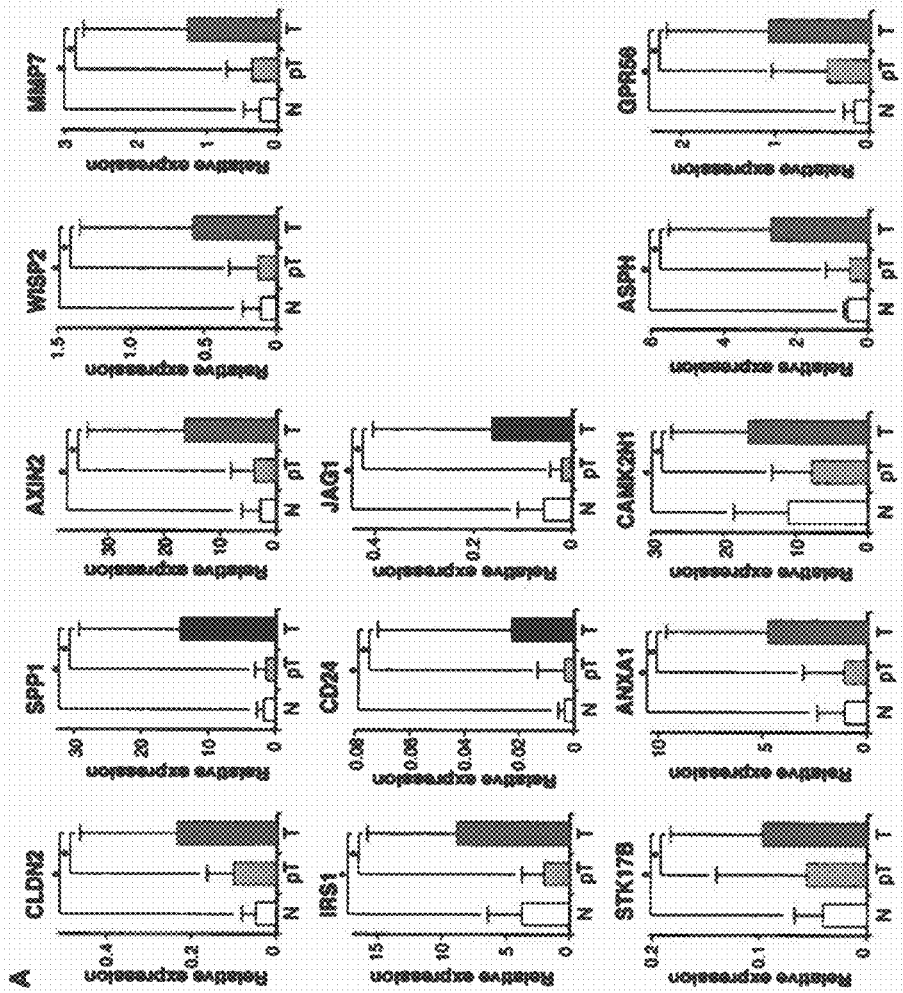
FIG. 14 shows the upregulation of 13 TCF-4J specific target genes in human HCCs.

Expression levels of target genes were measured by qRT-PCR in a 47 paired human HCC tumors (designated "T" in FIG. 14) and corresponding adjacent peritumor (designated "pT") and three normal liver tissues (designated "N"). FIG. 14 illustrates the increased expression levels of TCF-4J specific target genes.

Figure 15:
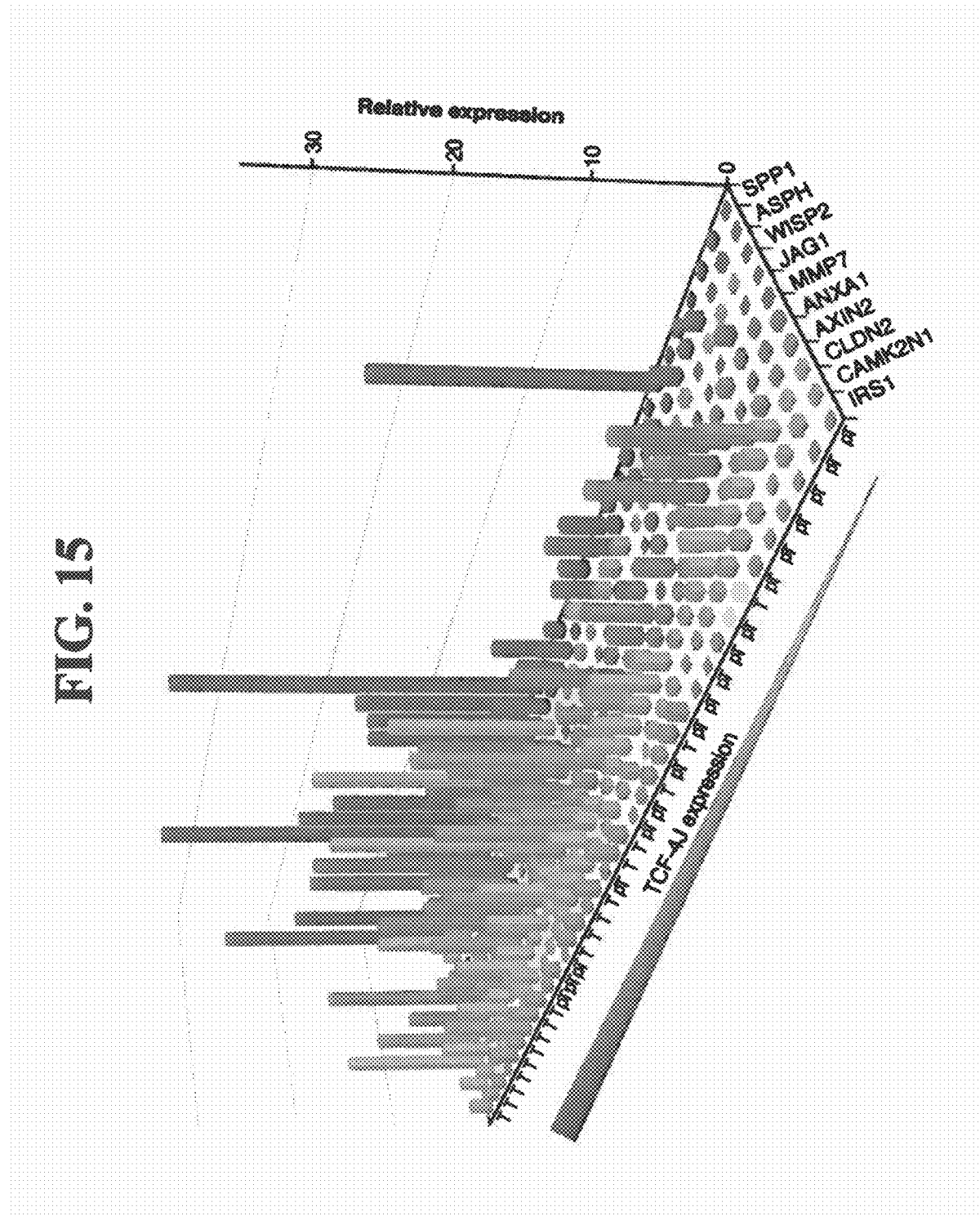
FIG. 15 is a 3-D bar drawing, indicating expression levels of 10 selected genes in tumor samples ordered according to the measured TCF-4J expression level, to show correlation between TCF-4J and target genes expression.

A 3D bar chart indicating expression levels of 10 selected in the tumor samples, ordered according to the measured TCF-4J expression level, is provided in FIG. 15. The expression level of TCF-4J was evaluated by semi-quantitative RT-PCR, and the values were normalized to GAPDH. qRT-PCR was used to evaluate expression levels of the selected genes, and the values were normalized to 18S rRNA. As shown in FIG. 15, tumors with high TCF-4J expression tended to have increased expression of more target genes.

5.7 Effect of Lenalidomide on TCF-4 Isoforms

The HCC cell lines (Focus and Hub7) were treated with 10 μM of LM in DMSO or DMSO as a control for 24 hrs. Total RNA was extracted, reverse transcribed into cDNA and TCF-4 isoforms were amplified by PCR. The expression of TCF-4C, J, and L was analyzed by qualification of the PCR product on gel and normalized by the express of the housekeeping gene GAPDH using ImageJ. The results are shown in FIG. 16.

Figure 17:
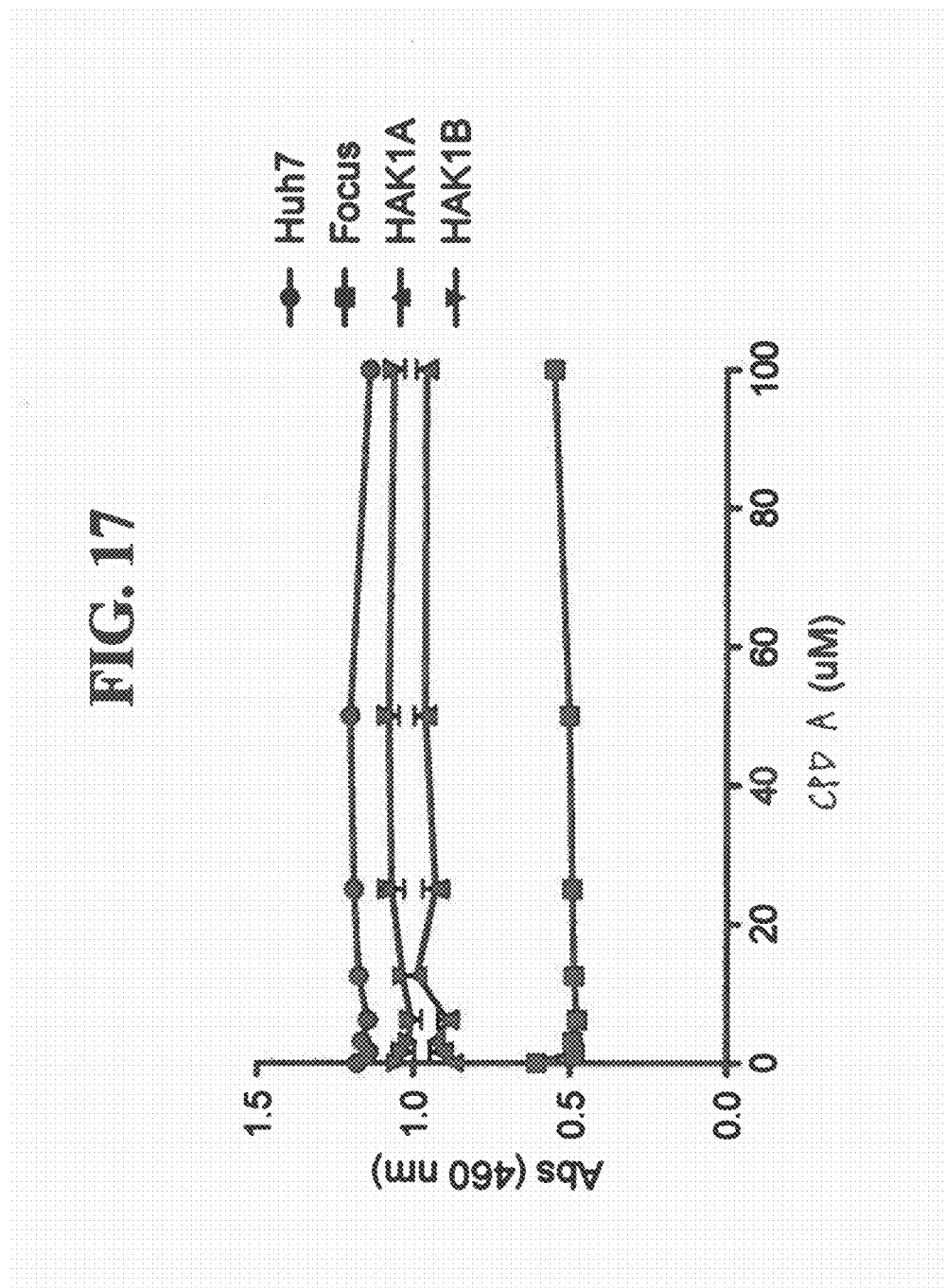
FIG. 17 shows that Compound A has no effect on HCC cell proliferation.

5.8 Cytotoxicity of 3-(5-amino-2-methyl-4-oxo-4H-quinazolin-3-yl)-piperidine-2,6-dione MTS assay was performed to evaluate the toxicity of Compound A for HCC cell lines Huh7, FOCUS, HAK-1A and HAK-1B. Compound A, at various concentrations ranging from 104 to 10004, was incubated with the specified cells for 24 or 72 hours. As shown in FIG. 17, no effect on HCC cell proliferation was observed for Compound A.

5.9 HAK1A-J Xenograft Models—Pilot Study

Figure 18:
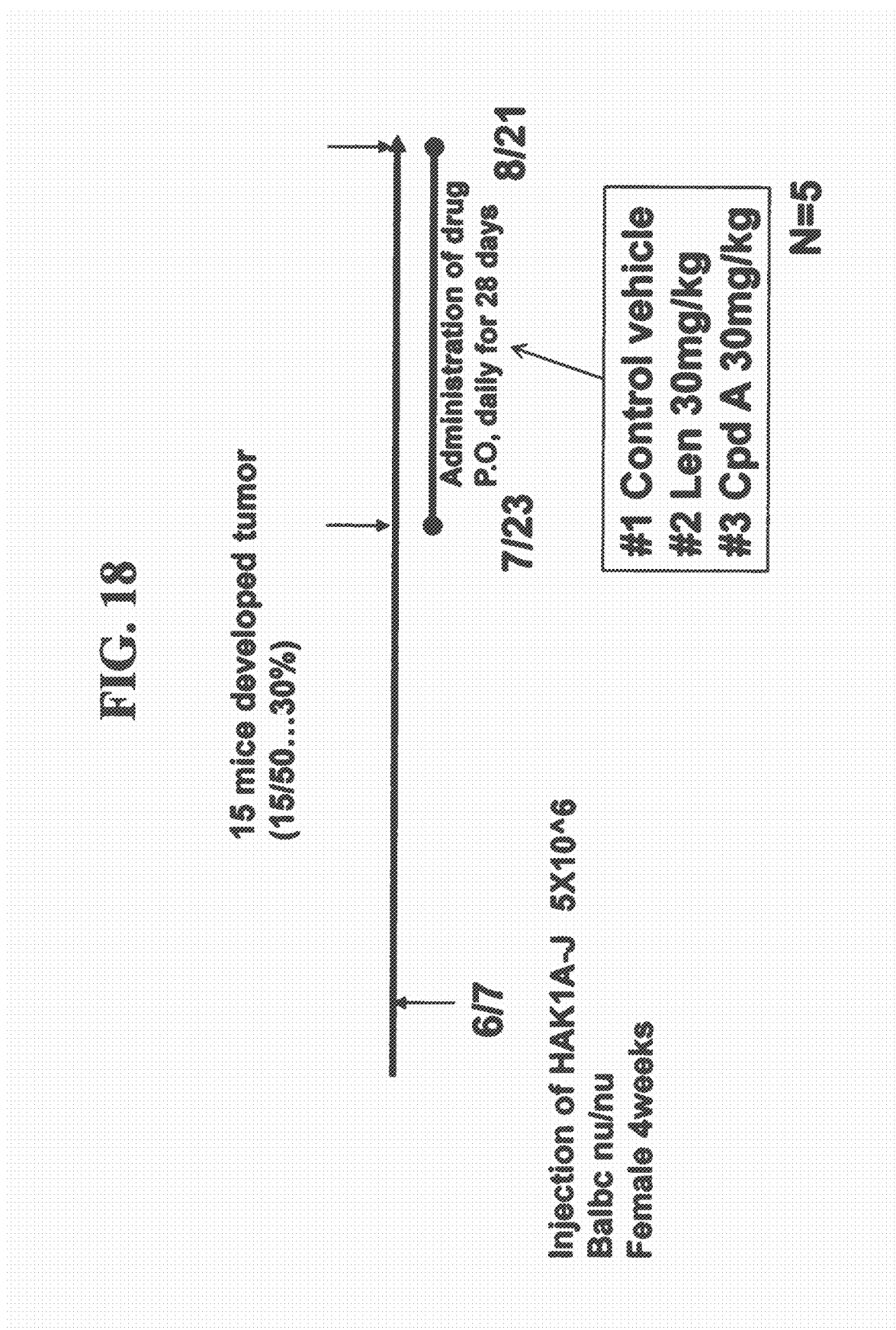
FIG. 18 is a schematic illustration of HAK1A-J xenograft models (pilot study) for studying the effect of administration of LM and Compound A to mice.
Figure 19:
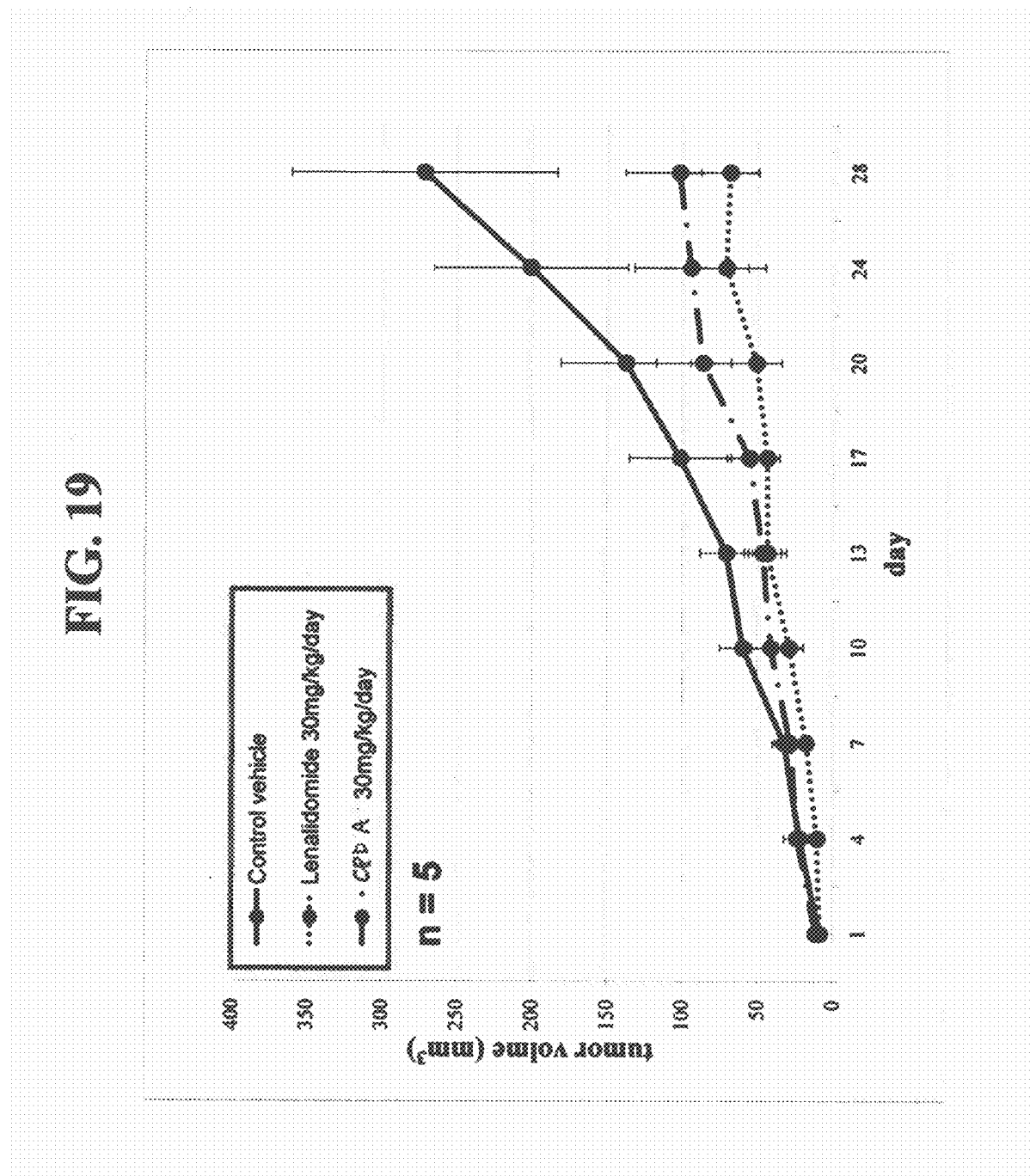
FIG. 19 shows the anti-tumor effects of LM and Compound A in HAK1A-J xenograft models as measured by reduction of tumor volume (pilot study).

Effects of LM and Compound A in HAK1A-J xenograft models were examined in a pilot study using 5 animals (mice). A schematic illustration of study procedure is shown in FIG. 18. Anti-tumor effects of LM and Compound A were assessed following the xenograft by measuring tumor volume after the treatment by the drugs. As shown in FIG. 19, both LM and Compound A significantly reduced the volume of tumors as compared with control.

5.10 HAK1A-J Xenograft Models

Figure 20:
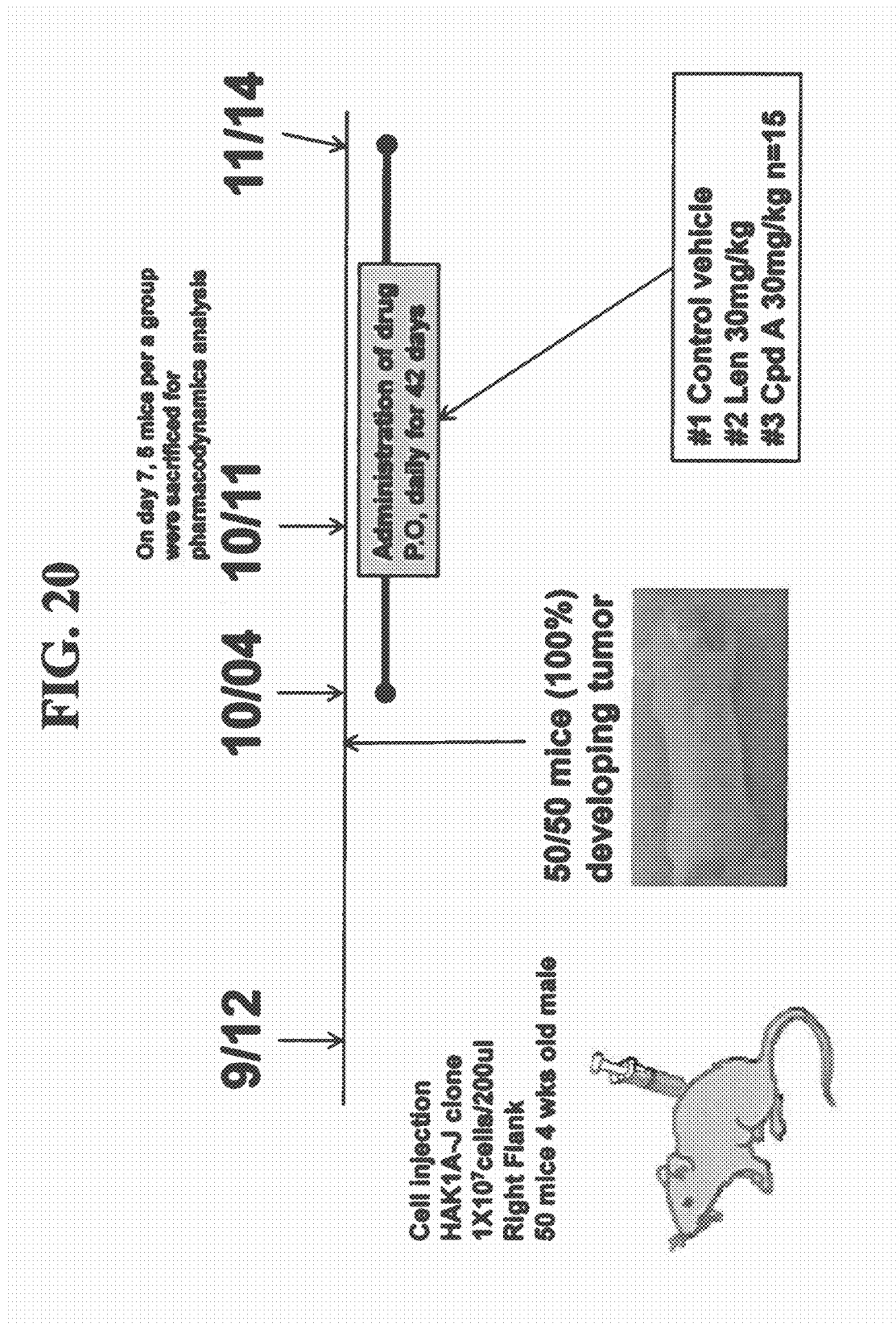
FIG. 20 is a schematic illustration of HAK1A-J xenograft models for studying the effect of administration of LM and Compound A to mice.
Figure 21:
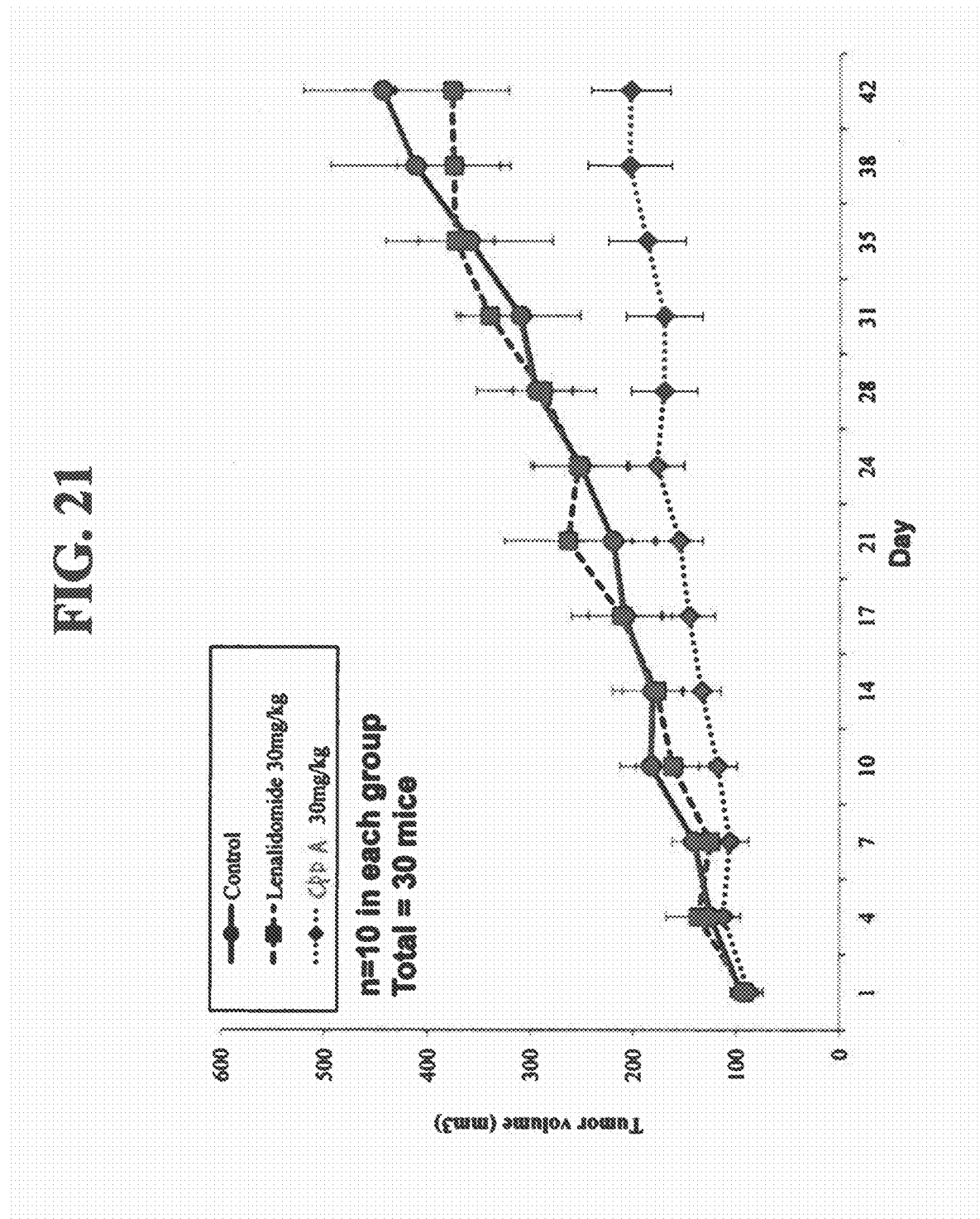
FIG. 21 shows the anti-tumor effects of LM and Compound A in HAK1A-J xenograft models as measured by reduction of tumor volume.

Effects of LM and Compound A in HAK1A-J xenograft models were examined using 50 male mice 4 weeks of age. A schematic illustration of study procedure is shown in FIG. 20. Anti-tumor effects of LM and Compound A were assessed following the xenograft by measuring tumor volume after the treatment by the drugs. As shown in FIG. 21, while reduction of tumor volume was observed in both LM and Compound A treated mice, Compound A much more significantly reduced the volume of tumors as compared with control or LM treated mice.

Figure 22:
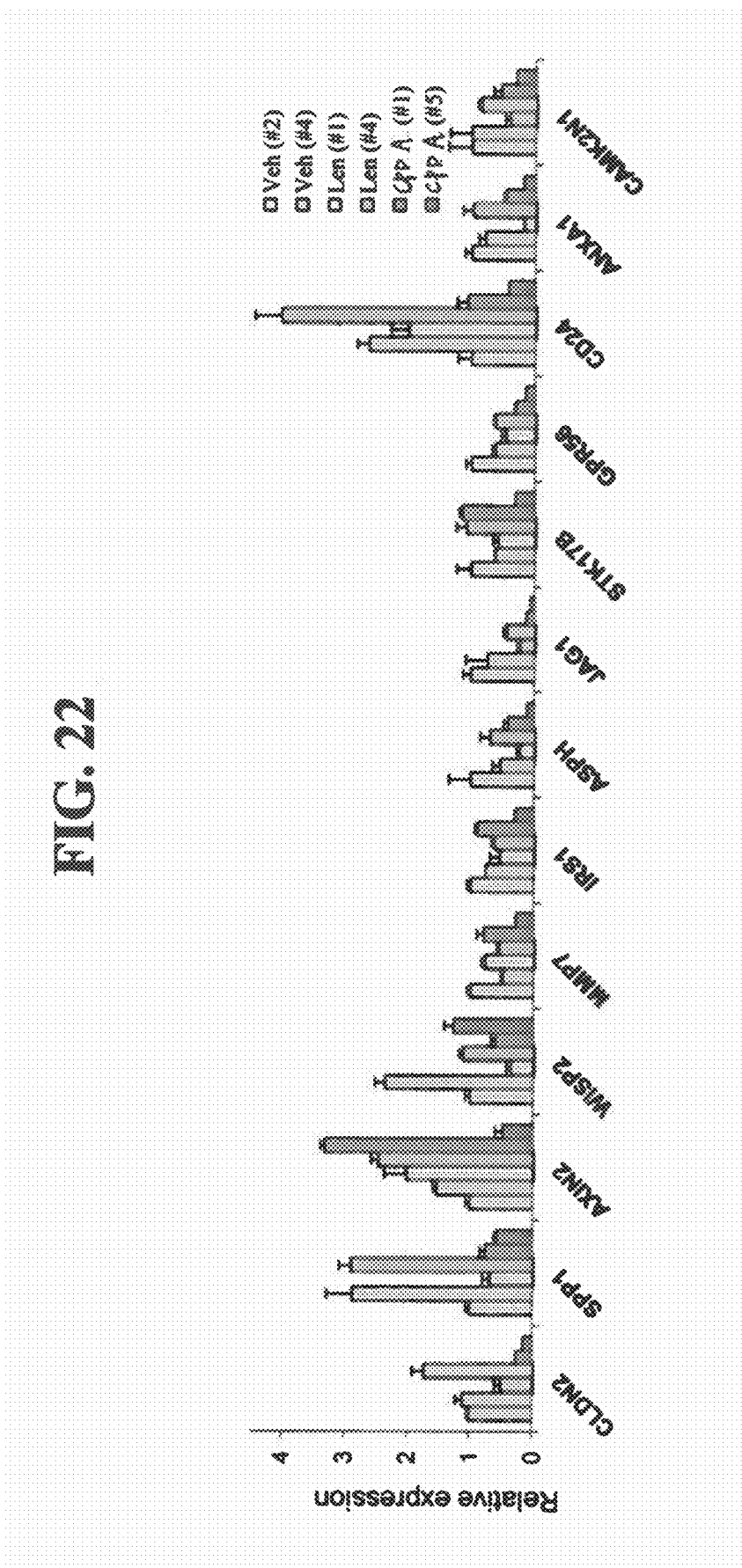
FIG. 22 shows the reduction of mRNA expression by LM and Compound A in HAK1A-J xenograft models.

Effects of LM and Compound A on expression of TCF-4J responsive target genes in HAK-1A xenograft tumors were assessed by measuring mRNA expression levels of TCF-4J isoform dependent target genes in xenograft tumors treated with LM, Compound A and control vehicle. The following procedures were used: Total RNA was extracted from tumors using TRIzol Reagent, and reverse transcription was performed with First Strand cDNA Synthesis Kit for RT-PCR (AMV). Quantitative real-time PCR was carried out on a Mastercycler ep realplex instrument and software, using SYBR Green PCR reagents. Relative quantification was performed using ΔΔCt method, normalizing to 18S rRNA. Dissociation curves were generated to evaluate PCR product specificity and purity. As shown in FIG. 22, it was found that mRNA levels of CLDN2, ASPH, JAG1, GPR56, ANXA1 and CAMK2N1 were reduced following the treatment by Compound A.

From the foregoing, it will be appreciated that, although specific embodiments have been described herein for the purpose of illustration, various modifications may be made without deviating from the spirit and scope of what is provided herein. All of the references referred to above are incorporated herein by reference in their entireties.

What is claimed is:

1. A method of treating hepatocellular carcinoma, comprising:
    identifying a subject having hepatocellular carcinoma who is likely to be responsive to a treatment compound, comprising:
        a) determining the level of a biomarker in a hepatocellular carcinoma cell-containing sample from the subject, wherein the biomarker is selected from the group consisting of TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, and combinations thereof; and
        b) comparing the level of the biomarker in the sample to a reference level of the biomarker; wherein the subject is likely to be responsive to the treatment if the level of the biomarker in the sample of the subject is higher than the reference level of the biomarker, wherein the reference level is a level determined from a sample containing no hepatocellular carcinoma cells;
    and administering a therapeutically effective amount of the treatment compound to the subject identified to be likely to be responsive to the treatment;
    wherein the hepatocellular carcinoma is poorly differentiated hepatocellular carcinoma;
    and wherein the treatment compound is thalidomide, lenalidomide, pomalidomide, or 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

2. A method of treating hepatocellular carcinoma, comprising:
    identifying a subject having hepatocellular carcinoma who is likely to be responsive to a treatment compound, comprising:
        a) determining the level of a biomarker in a hepatocellular carcinoma cell-containing sample from the subject, wherein the biomarker is selected from the group consisting of TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, and combinations thereof; and
        b) determining the level of the biomarker in a control sample; wherein the subject is likely to be responsive to the treatment if the level of the biomarker in the sample of the subject is higher than the level of the biomarker in the control sample, wherein the control sample is a sample containing no hepatocellular carcinoma cells;
    and administering a therapeutically effective amount of the treatment compound to the subject identified to be likely to be responsive to the treatment;
    wherein the hepatocellular carcinoma is poorly differentiated hepatocellular carcinoma;
    and wherein the treatment compound is thalidomide, lenalidomide, pomalidomide, or 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

3. A method of treating hepatocellular carcinoma, comprising:
    identifying a subject having hepatocellular carcinoma who is likely to be responsive to a treatment compound, comprising:
        a) obtaining a biological sample from the subject;
        b) determining the level of a biomarker in the sample, wherein the biomarker is selected from the group consisting of TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, and combinations thereof; and
        c) comparing the level of the biomarker in the sample to a reference level of the biomarker; wherein the subject is likely to be responsive to the treatment if the level of the biomarker in the sample of the subject is higher than the reference level of the biomarker, wherein the reference level is a level determined from a sample containing no hepatocellular carcinoma cells;
    and administering a therapeutically effective amount of the treatment compound to the subject identified to be likely to be responsive to the treatment;
    wherein the hepatocellular carcinoma is poorly differentiated hepatocellular carcinoma;
    and wherein the treatment compound is thalidomide, lenalidomide, pomalidomide, or 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

4. A method of treating hepatocellular carcinoma, comprising:
    identifying a subject having hepatocellular carcinoma who is likely to be responsive to a treatment compound, comprising:
        a) obtaining a biological sample from the subject;
        b) determining the level of a biomarker in the sample, wherein the biomarker is selected from the group consisting of TCF-4, WISP2, ASPH, IRS1, MAPK12, CLDN2, JAG1, GPR56, ANXA1, CAMK2N1, STK17B, SPP1, AXIN2, MMP7, CADM1, PLCD4, CD24, and combinations thereof; and
        c) determining the level of the biomarker in a control sample; wherein the subject is likely to be responsive to the treatment if the level of the biomarker in the sample of the subject is higher than the level of the biomarker in the control sample, wherein the control sample is a sample containing no hepatocellular carcinoma cells;
    and administering a therapeutically effective amount of the treatment compound to the subject identified to be likely to be responsive to the treatment;
    wherein the hepatocellular carcinoma is poorly differentiated hepatocellular carcinoma;
    and wherein the treatment compound is thalidomide, lenalidomide, pomalidomide, or 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

5. The method of claim 1, wherein the level of only one of the biomarkers is measured.

6. The method of claim 5, wherein the biomarker is TCF-4.

7. The method of claim 6, wherein the biomarker is hTCF-4.

8. The method of claim 5, wherein the biomarker is an isoform of TCF-4.

9. The method of claim 8, wherein the biomarker is TCF-4A, TCF-4B, TCF-4C, TCF-4D, TCF-4E, TCF-4F, TCF-4G, TCF-4H, TCF-4I, TCF-4J, TCF-4K, TCF-4L, TCF-4M, or TCF-4X.

10. The method of claim 8, wherein the biomarker is TCF-4C.

11. The method of claim 8, wherein the biomarker is TCF-4J.

12. The method of claim 8, wherein the biomarker is TCF-4L.

13. The method of claim 1, wherein the levels of two or more of the biomarkers are monitored simultaneously.

14. The method of claim 13, wherein the biomarker is WISP2, ASPH, IRS1, MAPK12, JAG1, or a combination thereof.

15. The method of claim 13, wherein the biomarker is CLDN2, ASPH, JAG1, GPR56, ANXA1, CAMK2N1, or a combination thereof.

16. The method of claim 13, wherein two or more of the biomarkers are selected from the groups consisting of TCF-4, TCF-4 isoforms, TCF-4A, TCF-4B, TCF-4C, TCF-4D, TCF-4E, TCF-4F, TCF-4G, TCF-4H, TCF-4I, TCF-4J, TCF-4K, TCF-4L, TCF-4M, TCF-4X, WISP2, ASPH, IRS1, MAPK12, CLDN2, JAG1, GPR56, ANXA1, CAMK2N1, STK17B, SPP1, AXIN2, MMP7, CADM1, PLCD4, CD24.

17. The method of claim 13, wherein two or more of the biomarkers are selected from the groups consisting of TCF-4, TCF-4 isoforms, TCF-4A, TCF-4B, TCF-4C, TCF-4D, TCF-4E, TCF-4F, TCF-4G, TCF-4H, TCF-4I, TCF-4J, TCF-4K, TCF-4L, TCF-4M, TCF-4X, WISP2, ASPH, IRS1, MAPK12, and JAG1.

18. The method of claim 13, wherein two or more of the biomarkers are selected from the groups consisting of TCF-4, TCF-4 isoforms, TCF-4A, TCF-4B, TCF-4C, TCF-4D, TCF-4E, TCF-4F, TCF-4G, TCF-4H, TCF-4I, TCF-4J, TCF-4K, TCF-4L, TCF-4M, TCF-4X, CLDN2, ASPH, JAG1, GPR56, ANXA1, and CAMK2N1.

19. The method of claim 13, wherein two or more of the biomarkers are selected from the groups consisting of TCF-4C, TCF-4J, TCF-4L, WISP2, ASPH, IRS1, MAPK12, and JAG.

20. The method of claim 13, wherein two or more of the biomarkers are TCF-4C, TCF-4J, TCF-4L, CLDN2, ASPH, JAG1, GPR56, ANXA1, and CAMK2N1.

21. The method of claim 1, wherein the levels of one or more of the biomarkers are measured by determining the mRNA levels of the biomarkers.

22. The method of claim 1, wherein the levels of one or more of the biomarkers are measured by determining the cDNA levels of the biomarkers.

23. The method of claim 1, wherein the levels of one or more of the biomarkers are measured by determining the protein levels of the biomarkers.

24. The method of claim 1, wherein the treatment compound is thalidomide.

25. The method of claim 1, wherein the treatment compound is lenalidomide.

26. The method of claim 1, wherein the treatment compound is pomalidomide.

27. The method of claim 1, wherein the treatment compound is 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

* * * * *

UNITED STATES PATENT AND TRADEMARK OFFICE
CERTIFICATE OF CORRECTION

PATENT NO.        : 8,901,110 B2                                          Page 1 of 1
APPLICATION NO.   : 13/740012
DATED             : December 2, 2014
INVENTOR(S)       : Kim et al.

It is certified that error appears in the above-identified patent and that said Letters Patent is hereby corrected as shown below:

In The Claims

In column 67, line 35 (part of claim 16), insert a term --and-- before the term "CD24" to read:
--PLCD4, and CD24.--

In column 68, line 15 (part of claim 20), insert a term --selected from the groups consisting of-- before the term "TCF-4C" to read:
--biomarkers are selected from the groups consisting of TCF-4C--

Signed and Sealed this
Twenty-second Day of March, 2016

Michelle K. Lee
*Director of the United States Patent and Trademark Office*